United States Patent
Dombrowski

(10) Patent No.: US 12,391,722 B2
(45) Date of Patent: *Aug. 19, 2025

(54) STABILIZED NUCLEIC ACIDS ENCODING MESSENGER RIBONUCLEIC ACID (MRNA)

(71) Applicant: Intellia Therapeutics, Inc., Cambridge, MA (US)

(72) Inventor: Christian Dombrowski, Auburndale, MA (US)

(73) Assignee: Intellia Therapeutics, Inc., Cambridge, MA (US)

( * ) Notice: Subject to any disclaimer, the term of this patent is extended or adjusted under 35 U.S.C. 154(b) by 114 days.

This patent is subject to a terminal disclaimer.

(21) Appl. No.: 18/310,298

(22) Filed: May 1, 2023

(65) Prior Publication Data

US 2023/0271997 A1  Aug. 31, 2023

Related U.S. Application Data

(63) Continuation of application No. 16/791,076, filed on Feb. 14, 2020, now Pat. No. 11,673,911, which is a continuation of application No. PCT/US2018/046772, filed on Aug. 14, 2018.

(60) Provisional application No. 62/545,883, filed on Aug. 15, 2017.

(51) Int. Cl.
| | |
|---|---|
| C12N 15/63 | (2006.01) |
| C07H 21/02 | (2006.01) |
| C12N 15/11 | (2006.01) |
| C12N 15/70 | (2006.01) |
| C07K 14/475 | (2006.01) |
| C07K 14/52 | (2006.01) |
| C12N 9/22 | (2006.01) |

(52) U.S. Cl.
CPC ............ *C07H 21/02* (2013.01); *C12N 15/11* (2013.01); *C12N 15/63* (2013.01); *C07K 14/475* (2013.01); *C07K 14/521* (2013.01); *C12N 9/22* (2013.01)

(58) Field of Classification Search
None
See application file for complete search history.

(56) References Cited

U.S. PATENT DOCUMENTS

| | | | |
|---|---|---|---|
| 11,673,911 B2 * | 6/2023 | Dombrowski | C07H 21/02 536/23.2 |
| 2016/0243258 A1 | 8/2016 | Scharenberg et al. | |
| 2017/0166905 A1 | 6/2017 | Eberle et al. | |
| 2018/0119213 A1 | 5/2018 | Kim et al. | |

FOREIGN PATENT DOCUMENTS

| | | |
|---|---|---|
| KR | 101786396 B1 | 11/2017 |
| WO | 2016115355 A1 | 7/2016 |

OTHER PUBLICATIONS

Chang, H. et al., "TAIL-seq: Genome-wide Determination of Poly(A) Tail Length and 3' End Modifications" Cell Press, vol. 53, Mar. 20, 2014 (Mar. 20, 2014) pp. 1044-1052.

International Search and Written Opinion issued for PCT/US2018/046772 on Dec. 4, 2018.

Jalkanen, A. et al., "Determinants and implications of mRNA poly(A) tail size—Does this protein make my tail look big?" Seminars in Cell and Developmental Biology, vol. 34, Oct. 1, 2014 (Oct. 1, 2014), pp. 24-32.

Lim, J. et al., "Mixed tailing by TENT4A and TENT4B shields mRNA from rapid deadenylation" Science, vol. 361, No. 6403, Jul. 19, 2018 (Jul. 19, 2018), pp. 701-704.

Lim, J. et al., "Uridylation by TUT4 and TUT7 Marks mRNA for Degradation" Cell, vol. 159, No. 6, Dec. 4, 2014 (Dec. 4, 2014), pp. 1365-1376.

Sergeeva, O.V. et al., "mRNA-Based Therapeutics—Advances and Perspectives" Biochemistry (Moscow) 81 (7):709-722 (2016).

* cited by examiner

*Primary Examiner* — Weihua Fan

(74) *Attorney, Agent, or Firm* — McNeill PLLC

(57) ABSTRACT

This disclosure relates to the field of poly-adenylated (poly-A) tails. In some embodiments, a DNA encodes a poly-A tail located 3' to nucleotides encoding a protein of interest, wherein the poly-A tail comprises one or more non-adenine nucleotide.

23 Claims, 7 Drawing Sheets

Specification includes a Sequence Listing.

SEQUENCE LISTING

```
Sequence total quantity: 31
SEQ ID NO: 1              moltype = DNA  length = 108
FEATURE                   Location/Qualifiers
misc_feature              1..108
                          note = mRNA sequence of an exemplary poly-A tail comprising
                            non-adenine nucleotides with 30, 30, and 39 consecutive
                            adenosines and ending with non-adenine nucleotides
source                    1..108
                          mol_type = other DNA
                          organism = synthetic construct
SEQUENCE: 1
aaaaaaaaaa aaaaaaaaaa aaaaaaaaaa gcgaaaaaaa aaaaaaaaaa aaaaaaaaa      60
aaaccgaaaa aaaaaaaaaa aaaaaaaaaa aaaaaaaaaa aaaaccc                  108

SEQ ID NO: 2              moltype = DNA  length = 104
FEATURE                   Location/Qualifiers
misc_feature              1..104
                          note = 30PA - sequence of an exemplary poly-A tail
                            comprising non-adenine nucleotides with 30, 30, and 39
                            consecutive adenosines
source                    1..104
                          mol_type = other DNA
                          organism = synthetic construct
SEQUENCE: 2
aaaaaaaaaa aaaaaaaaaa aaaaaaaaaa gcgaaaaaaa aaaaaaaaaa aaaaaaaaa      60
aaaccgaaaa aaaaaaaaaa aaaaaaaaaa aaaaaaaaaa aaaa                     104

SEQ ID NO: 3              moltype = DNA  length = 109
FEATURE                   Location/Qualifiers
misc_feature              1..109
                          note = 25PA - sequence of an exemplary poly-A tail
                            comprising non-adenine nucleotides with four sets of 25
                            consecutive adenosines
source                    1..109
                          mol_type = other DNA
                          organism = synthetic construct
SEQUENCE: 3
aaaaaaaaaa aaaaaaaaaa aaaaagcgaa aaaaaaaaaa aaaaaaaaaa aaaccgaaaa     60
aaaaaaaaaa aaaaaaaaaa agtgaaaaaa aaaaaaaaaa aaaaaaaaa                109

SEQ ID NO: 4              moltype = DNA  length = 101
FEATURE                   Location/Qualifiers
misc_feature              1..101
                          note = 16PA - sequence of an exemplary poly-A tail
                            comprising non-adenine nucleotides with six sets of 16
                            consecutive adenosines
source                    1..101
                          mol_type = other DNA
                          organism = synthetic construct
SEQUENCE: 4
aaaaaaaaaa aaaaagaaa aaaaaaaaaa aaacaaaaaa aaaaaaaaaa taaaaaaaaa      60
aaaaaaataa aaaaaaaaaa aaacaaaaa aaaaaaaaaa a                         101

SEQ ID NO: 5              moltype = DNA  length = 165
FEATURE                   Location/Qualifiers
misc_feature              1..165
                          note = 16PA long - sequence of an exemplary poly-A tail
```

|  |  | comprising non-adenine nucleotides with six sets of 16 consecutive adenosines and 63 consecutive adenosines |
|---|---|---|

```
                    source          1..165
                                    mol_type = other DNA
                                    organism = synthetic construct
SEQUENCE: 5
aaaaaaaaaa aaaaagaaaa aaaaaaaaaa aaacaaaaaa aaaaaaaaaa taaaaaaaaa   60
aaaaaaataa aaaaaaaaaa aaaacaaaaa aaaaaaaaaa acaaaaaaaa aaaaaaaaaa  120
aaaaaaaaaa aaaaaaaaaa aaaaaaaaaa aaaaaaaaaa aaaaa                  165

SEQ ID NO: 6           moltype = DNA   length = 4523
FEATURE                Location/Qualifiers
misc_feature           1..4523
                       note = Cas9 mRNA with a poly-A tail consisting of 97
                        adenosines
source                 1..4523
                       mol_type = other DNA
                       organism = synthetic construct
SEQUENCE: 6
taatacgact cactataggg tcccgcagtc ggcgtccagc ggctctgctt gttcgtgtgt   60
gtgtcgttgc aggccttatt cggatccatg gataagaagt actcaatcgg gctggatatc  120
ggaactaatt ccgtgggttg ggcagtgatc acggatgaat acaaagtgcc gtccaagaag  180
ttcaaggtcc tggggaacac cgatagacac agcatcaaga aaaatctcat cggagccctg  240
ctgtttgact ccgcgaaaac cgcagaagcg acccggctca acgtaccgc gaggcgacgc  300
tacacccggc ggaagaatcg catctgctat ctgcaagaga tcttttcgaa cgaaatggca  360
aaggtcgacg acagcttctt ccaccgcctg gaagaatctt tcctggtgga ggaggacaag  420
aagcatgaac ggcatcctat ctttggaaac atcgtcgacg aagtggcgta ccacgaaaag  480
tacccgacca tctaccatct gcggaagaag ttggttgact caactgacaa ggccgacctc  540
agattgatct acttggccct cgcccatatg atcaaattcc gcggacactt cctgatcgaa  600
ggcgatctga accctgataa ctccgacgtg gataagcttt tcattcaact ggtgcagacc  660
tacaaccaac tgttcgaaga aaacccaatc aatgctagcg gcgtcgatgc caaggccatc  720
ctgtccgccc ggctgtcgaa gtcgcggcgc ctcgaaaacc tgatcgcaca gctgccggga  780
gagaaaaaga acggactttt cggcaacttg atcgctctct cactgggact cactcccaat  840
ttcaagtcca atttttgacct ggccgaggac gcgaagctgc aactctcaaa ggacacctac  900
gacgacgact tggacaattt gctggcacaa attgcgatc agtacgcgga tctgttcctt  960
gccgctaaga acctttcgga cgcaatcttg ctgtccgata tcctgcgcgt gaacaccgaa 1020
ataaccaaag cgccgcttag cgcctcgatg attaagcggt acgacgagca tcaccaggat 1080
ctcacgctgc tcaaagcgct cgtgagacag caactgcctg aaaagtacaa ggagatcttc 1140
ttcgaccagt ccaagaatgg gtacgcaggg tacatcgatg gctag ccaggaagag 1200
ttctataagt tcatcaagcc aatcctggaa aagatggacg gaaccgaaga actgctggtc 1260
aagctgaaca ggaggatct gctccggaaa cagagaacct tgacaacgg atccattccc 1320
caccagatcc atctgggtga gctgcacgcc atcttgcggc gccaggagga cttttaccca 1380
ttcctcaagg acaaccggga aaagatcgag aaaattctga cgttccgcat cccgtattac 1440
gtgggcccac tggcgcgcgg caattcgcgc ttcgcgtgga tgactagaaa atcagaggaa 1500
accatcactc cttggaatttt cgaggaagtt gtggataagg gagcttcggc acaaagcttc 1560
atcgaacgaa tgaccaactt cgacaagaat ctcccaaacg agaaggtgct tcctaagcac 1620
agcctccttt acgaatactt cactgtctac aacgaactga ctaaagtgaa atacgttact 1680
gaaggaatga ggaagccggc cttttctgtcc ggagaacaga agaaaagcaat tgtcgatctg 1740
ctgttcaaga ccaaccgcaa ggtgaccgtc aagcagctta agaggacta cttcaagaag 1800
atcgagtgtt tcgactcagt ggaaatcagc ggggtggagg acagattcaa cgcttcgctg 1860
ggaacctatc atgatctcct gaagatcatc aaggacaagg acttccttga caacgaggag 1920
aacgaggaca tcctggaaga tatcgtcctg accttgaccc ttttcgagga tcgcgagatg 1980
atcgaggaga ggcttaagac ctacgctcat ctcttcgacg ataagtcat gaaacaactc 2040
aagcgccgcc ggtacactgg ttggggccgc ctctcccgca agctgatcaa cggtattcgc 2100
gataaacaga gcggtaaaac tatcctggat ttcctcaaat cggatggtct gctaatcgt 2160
aacttcatgc aattgatcca cgacgacagc ctgacctta aggaggacat ccaaaaagca 2220
caagtgtccg gacagggaga ctcactccat gaacacatcg cgaatctggc cggttcgccg 2280
gcgattaaga agggaattct gcaaactgtg aaggtggtcg acgagctggt gaaggtcatg 2340
ggacggcaca aaccggagaa tatcgtgatt gaaatggccc gagaaaacca gactacccag 2400
aagggccaga aaaactcccg cgaaaggatg aagcggatcg aagaaggaat caaggagctg 2460
ggcagccaga tcctgaaaga gcaccgggtg gaaaacacgc agctcagaa cgagaagctc 2520
tacctgtact atttgcaaaa tggacggac atgtacgtgg accaagagct ggacatcaat 2580
cggttgtctg attacgacgt ggaccacatc gttccacagt cctttctgaa ggatgactcg 2640
atcgataaca aggtgttgac tcgcagcgac aagaacagg taatcgtgcc a            2700
tcggaggagg tcgtgaagaa gatgaagaat tactggcggc agctcctgaa tgcgaagctg 2760
attcccagaa gaaagtttga caatctcact aaagccgagc gcggcggact ctcagagctg 2820
gataaggctg gattcatcaa acggcagctg gtcgagactc ggcagattac caagcacgtg 2880
gcgcagatct tggactcccg catgaacact aaatacgacg agaacgataa gctcatccgg 2940
gaagtgaagg tgattaccct gaaaagcaaa cttgtctcgg actttcggga ggactttcag 3000
ttttacaaag tgagagaaat caacaactac catcacgcgc atgacgcata cctcaacgct 3060
gtggtcggta ccgccctgat caaaaagtac cctaaacttg aatcggagtt tgtgtacgga 3120
gactacaagg tctacgacgt gaggaagatg atagccaagt ccgaacagga atcgggaaa 3180
gcaactgcga aatacttctt ttactcaaac atcatgaact tttttcaagac tgaaattacg 3240
ctggccaatg gaganaatcag gaagaggcca ctgatcgaaa ctaacgagga aacggcgcaa 3300
atcgtgtggg acaagggcag ggacttcgca actgttcgca aagtgctctc tatgccgcaa 3360
gtcaatattg tgaagaaaac cgaagtgcaa accggcggat tttcaaagga tcgatcctc 3420
ccaaagagaa atacgcaca gctcattgca cgcaagaaag actgggaccc gaagaagtac 3480
ggaggattcg attcgccgac tgtcgcatac tccgtcctcg tggtgccaa ggtggagaag 3540
ggaaagagca aaaagctcaa atccgtcaaa gagctgctgg gattaccat catggaacga 3600
```

```
tcctcgttcg agaagaaccc gattgatttc ctcgaggcga agggttacaa ggaggtgaag   3660
aaggatctga tcatcaaact ccccaagtac tcactgttcg aactggaaaa tggtcggaag   3720
cgcatgctgg cttcggccgg agaactccaa aaaggaaatg agctggcctt gcctagcaag   3780
tacgtcaact tcctctatct tgcttcgcac tacgaaaaac tcaaagggtc accggaagat   3840
aacgaacaga agcagctttt cgtggaacag cacaagcatt atctggatga aatcatcgaa   3900
caaatctccg agttttcaaa gcgcgtgatc ctcgccgacg ccaacctcga caaagtcctg   3960
tcggcctaca ataagcatag agataagccg atcagagaac aggccgagaa cattatccac   4020
ttgttcaccc tgactaacct gggagcccca gccgccttca agtacttcga tactactatc   4080
gatcgcaaaa gatacacgtc caccaaggaa gttctggacg cgaccctgat ccaccaaagc   4140
atcactggac tctacagaac taggatcgat ctgtcgcagc tgggtggcga tggcggtgga   4200
tctccgaaaa agaagagaaa ggtgtaatga gctagccatc acatttaaaa gcatctcagc   4260
ctaccatgag aataagagaa agaaaatgaa gatcaatagc ttattcatct cttttctctt   4320
ttcgttggtg taaagccaac accctgtcta aaaaacataa atttctttaa tcatttttgcc   4380
tcttttctct gtgcttcaat taataaaaaa tggaaagaac ctcgagaaaa aaaaaaaaaa   4440
aaaaaaaaaa aaaaaaaaaa aaaaaaaaaa aaaaaaaaaa aaaaaaaaaa aaaaaaaaaa   4500
aaaaaaaaaa aaaaaaaaaa aaa                                          4523

SEQ ID NO: 7             moltype = DNA  length = 4581
FEATURE                  Location/Qualifiers
misc_feature             1..4581
                         note = T7 promoter and Cas9 mRNA with a poly-A tail
                          comprising SEQ ID NO: 1
source                   1..4581
                         mol_type = other DNA
                         organism = synthetic construct
SEQUENCE: 7
taatacgact cactataggg tcccgcagtc ggcgtccagc ggctctgctt gttcgtgtgt    60
gtgtcgttgc aggccttatt cggatctgcc accatggata gaagtactc gatcgggctg    120
gatatcggaa ctaattccgt gggttgggca gtgatcacgg atgaatacaa agtgccgtcc    180
aagaagttca aggtcctggg gaacaccgat agacacagca tcaagaagaa tctcatcgga    240
gccctgctgt ttgactccgg cgaaaccgca gaagcgaccc ggctcaaacg taccgcgagg    300
cgacgctaca cccggcggaa gaatcgcatc tgctatctgc aagaaatctt ttcgaacgaa    360
atggcaaagg tggacgacag cttcttccac cgcctgaaag aatctttcct ggtggaggag    420
gacaagaagc atgaacggca tcctatcttt ggaaacatcg tggacgaagt ggcgtaccaa    480
gaaaagtacc cgaccatcta ccatctgcgg aagaagttgg ttgactcaac tgacaaggcc    540
gacctcagat tgatctactt ggccctcgcc catatgatca aattccgcgg acacttcctg    600
atcgaaggcg atctgaaccc tgataactcc gacgtggata gctgttcat tcaactggtg    660
cagacctaca accaactgtt cgaagaaaac ccaatcaatg ccagcggcgt cgatgccaag    720
gccatcctgt ccgcccggct gtcgaagtcg ccggcgtcca aaaacctgat cgcacagctg    780
ccggagaga agaagaacgg acttttcggc aacttgatcg ctctctcact gggactcact    840
cccaatttca gtccaatttt tgacctggcc gaggacgcga agctgcaact ctcaaaggac    900
acctacgacg acgacttgga caatttgctg gcacaaattg gcgatcagta cgcggatctg    960
ttccttgccg ctaagaacct ttcggacgca atcttgctgt cgatatcct gcgcgtgaac    1020
accgaaataa ccaaagcgcc gcttagcgcc tcgatgatta gcggtacga cgagcatcac    1080
caggatctca cgctgctcaa agcgctcgtg agacagcaac tgcctgaaaa gtacaaggag    1140
attttcttgc accagtccaa gaatgggtac gcagggtaca tcgatggagg cgccagccag    1200
gaagagttct ataagttcat caagcaaatc tggaaaaga tgacgaaac cgaagaactg    1260
ctggtcaagc tgaacaggga ggatctgctc cgcaaacaga gaacctttga caacggaagc    1320
attccacacc agatccatct gggtgagctg cacgccatct gcggcgcca ggaggacttt    1380
tacccattcc tcaaggacaa ccgggaaaag atcgagaaaa ttctgacgtt ccgcatcccg    1440
tattacgtgg gcccactggc gcgcggcaat tcgcgcttcg cgtggatgac tagaaaatca    1500
gaggaaacca tcactccttg gaatttcgag gaagttgtgg ataagggagc ttcggcacaa    1560
tccttcatcg aacgaatgac caacttcgac aagaatctcc caaacgagaa ggtgcttcct    1620
aagcacagcc tcctttacga atacttcact gtctacaacg aactgactaa agtgaaatac    1680
gttactgaag gaatgaggaa gccggccttt ctgagcggaa aacagaagaa agcgattgtc    1740
gatctgctgt tcaagaccaa ccgcaaggtg accgtcaagc agcttaaaga ggactacttc    1800
aagaagatcg agtgtttcga ctcagtggaa atcagcggag tggaggacag attcaacgct    1860
tcgctgggaa cctatcatga tctcctgaag atcatcaagg acaaggactt ccttgacaac    1920
gaggagaaca aggacctcct ggaagatatc gtcctgacct tgaccctttt cgaggatcgg    1980
gagatgatcg aggagaggct taagacctac gctcatctct tcgacgataa ggtcatgaaa    2040
caactcaagc gccgcggtg cactggtggg ggccgcctct cccgcaagct gatcaacggt    2100
attcgcgata acagagcgg taaaactatc ctggatttcc tcaaatcgga tggcttcgct    2160
aatcgtaact tcatgcagtt gatccacgac gacagcctga cctttaagga ggacatccag    2220
aaagcacaag tgagcggaca gggagctca ctccatgaac ggctggtcg tctggccagt    2280
tgccggcga ttaagaaggg aatcctgcaa actgtgaagg tggtggacga gctggtgaag    2340
gtcatgggac ggcacaaacc ggagaatatc gtgattgaaa tggcccgaga aaaccagact    2400
acccagaagg gccagaagaa ctcccgcgaa aggatgaagc ggatcgaaga aggaatcaag    2460
gagctgggca gccagatcct gaaagagcac ccggtggaaa acactcagct cgagaacgag    2520
aagctctacc tgtactattt gcaaaatgga cgggacatgt acgtggacca agagctggac    2580
atcaatcggt tgtctgatta cgacgtggac cacatcgttc cacagtcctt tctgaaggat    2640
gactccatcg ataacaaggt gttgactcgc agcgacaaga cagagggaa gtcagataat    2700
gtgccatcgg aggaggtcgt gaagaagatg aagaattact ggcggcagct cctgaatgcg    2760
aagctgatta cccagagaaa gtttgacaat ctcactaaag ccgagcgcgg cggactctca    2820
gagctggata aggctggatt catcaaacgc cagctggtcg agacgcggca gatcaccaag    2880
cacgtggcgc agatcctgga ctcccgcatg aacactaaat acgacgagaa cgataagctc    2940
atccgggaag tgaaggtgat taccctgaaa agcaaacttg tgtcggactt cggaaggac    3000
tttcagtttt acaaagtgag agaaatcaac aactaccatc acgcgcatga cgcataccctc    3060
aacgctgtgg tcggcaccgc cctgatcaag aagtacccta aacttgaatc ggagtttgtg    3120
tacgagact acaaggtcta cgacgtgagg aagatgatag ccaagtccga acaggaaatc    3180
```

-continued

```
gggaaagcaa ctgcgaaata cttcttttac tcaaacatca tgaacttctt caagactgaa    3240
attacgctgg ccaatggaga aatcaggaag aggccactga tcgaaactaa cggagaaacg    3300
ggcgaaatcg tgtgggacaa gggcagggac ttcgcaactg ttcgcaaagt gctctctatg    3360
ccgcaagtca atattgtgaa gaaaaccgaa gtgcaaaccg gcggattttc aaaggaatcg    3420
atcctcccaa agagaaatag cgacaagctc attgcacgca agaaagactg ggacccgaag    3480
aagtacggag gattcgattc gccgactgtc gcatactccg tcctcgtggt ggccaaggtg    3540
gagaagggaa agagcaagaa gctcaaatcc gtcaaagagc tgctggggat taccatcatg    3600
gaacgatcct cgttcgagaa gaacccgatt gatttcctgg aggcgaaggg ttacaaggag    3660
gtgaagaagg atctgatcat caaactgccc aagtactcac tgttcgaact ggaaaatggt    3720
cggaagcgca tgctggcttc ggccggagaa ctccagaaag gaaatgagct ggccttgcct    3780
agcaagtacg tcaacttcct ctatcttgct tcgcactacg agaaactcaa agggtcaccg    3840
gaagataacg aacagaagca gcttttcgtg gagcagcaca agcattatct ggatgaaatc    3900
atcgaacaaa tctccgagtt ttcaaagcgc gtgatcctcg ccgacgccaa cctcgacaaa    3960
gtcctgtcgg cctacaataa gcatagagat aagccgatca gagaacaggc cgagaacatt    4020
atccacttgt tcaccctgac taacctggga gctccagccg ccttcaagta cttcgatact    4080
actatcgacc gcaaaagata cacgtccacc aaggaagttc tggacgcgac cctgatccac    4140
caaagcatca ctggactcta cgaaactagg atcgatctgt cgcagctggg tggcgatggt    4200
ggcggtggat cctacccata cgacggtgcct gactacgcct ccggaggtgg tggccccaag    4260
aagaaacgga aggtgtgata gctagccatc acatttaaaa gcatctcagc ctaccatgag    4320
aataagagaa agaaaatgaa gatcaatagc ttattcatct ctttttcttt ttcgttggtg    4380
taaagccaac accctgtcta aaaaacataa atttctttaa tcattttgcc tcttttctct    4440
gtgcttcaat taataaaaaa tggaaagaac ctcgagaaaa aaaaaaaaaa aaaaaaaaaa    4500
aaaaagcga aaaaaaaaaa aaaaaaaaaa aaaaaaaaac cgaaaaaaaa aaaaaaaaaa    4560
aaaaaaaaaa aaaaaaaaaa a                                             4581
```

```
SEQ ID NO: 8            moltype = RNA  length = 100
FEATURE                 Location/Qualifiers
misc_feature            1..100
                        note = Single guide RNA targeting SEAP
modified_base           1..3
                        mod_base = OTHER
                        note = Each nucleotide modified with 2'-O-Me and is linked
                          to the next nucleotide with a Phosphorothioate (PS)
                          linkage or bond
modified_base           29..39
                        mod_base = OTHER
                        note = 2'-O-Me
modified_base           68..96
                        mod_base = OTHER
                        note = 2'-O-Me
modified_base           97..99
                        mod_base = OTHER
                        note = Each nucleotide modified with 2'-O-Me and is linked
                          to the next nucleotide with a Phosphorothioate (PS)
                          linkage or bond
modified_base           100
                        mod_base = OTHER
                        note = 2'-O-Me
source                  1..100
                        mol_type = other RNA
                        organism = synthetic construct
SEQUENCE: 8
ctccctgatg gagatgacag gttttagagc tagaaatagc aagttaaaat aaggctagtc    60
cgttatcaac ttgaaaaagt ggcaccgagt cggtgctttt                          100
```

```
SEQ ID NO: 9            moltype = RNA  length = 100
FEATURE                 Location/Qualifiers
misc_feature            1..100
                        note = Single guide RNA targeting mouse TTR
modified_base           1..3
                        mod_base = OTHER
                        note = Each nucleotide modified with 2'-O-Me and is linked
                          to the next nucleotide with a Phosphorothioate (PS)
                          linkage or bond
modified_base           29..39
                        mod_base = OTHER
                        note = 2'-O-Me
modified_base           68..96
                        mod_base = OTHER
                        note = 2'-O-Me
modified_base           97..99
                        mod_base = OTHER
                        note = Each nucleotide modified with 2'-O-Me and is linked
                          to the next nucleotide with a Phosphorothioate (PS)
                          linkage or bond
modified_base           100
                        mod_base = OTHER
                        note = 2'-O-Me
source                  1..100
```

```
                        mol_type = other RNA
                        organism = synthetic construct
SEQUENCE: 9
ttacagccac gtctacagca gttttagagc tagaaatagc aagttaaaat aaggctagtc    60
cgttatcaac ttgaaaaagt ggcaccgagt cggtgctttt                          100

SEQ ID NO: 10           moltype = DNA   length = 116
FEATURE                 Location/Qualifiers
misc_feature            1..116
                        note = 12PA - mRNA sequence of an exemplary poly-A tail
                         comprising non-adenine nucleotides with nine sets of 12
                         consecutive adenosines and mononucleotide interrupting
                         sequences
source                  1..116
                        mol_type = other DNA
                        organism = synthetic construct
SEQUENCE: 10
aaaaaaaaaa aataaaaaaa aaaaataaaa aaaaaaaaca aaaaaaaaaa ataaaaaaaa    60
aaaacaaaaa aaaaaaagaa aaaaaaaaaa caaaaaaaaa aaataaaaaa aaaaaa        116

SEQ ID NO: 11           moltype = DNA   length = 115
FEATURE                 Location/Qualifiers
misc_feature            1..115
                        note = 8PA - mRNA sequence of an exemplary poly-A tail
                         comprising non-adenine nucleotides with twelve sets of 8
                         consecutive adenosines and mononucleotide interrupting
                         sequences
source                  1..115
                        mol_type = other DNA
                        organism = synthetic construct
SEQUENCE: 11
aaaaaaaata aaaaaaataa aaaaacaaaa aaaaaaaaaa aaagaaaaaa aataaaaaaa    60
acaaaaaaaa caaaaaaaat aaaaaaaaga aaaaaaacaa aaaaaataaa aaaaa         115

SEQ ID NO: 12           moltype = DNA   length = 159
FEATURE                 Location/Qualifiers
misc_feature            1..159
                        note = PolyA-1, Bcl11a primer annealing sites flanking
                         sequence comprising five interrupting sequences separating
                         six repeats of 12 consecutive adenosines
source                  1..159
                        mol_type = other DNA
                        organism = synthetic construct
SEQUENCE: 12
tcttccttca gtctgtaaac ctcagctcga gaaaaaaaaa aaatggaaaa aaaaaaaacg    60
gaaaaaaaaa aaaggtaaaa aaaaaaaata taaaaaaaaa aaacataaaa aaaaaaacg   120
ttcatatcgg ttctagacca cacttcttac tgaggtccc                          159

SEQ ID NO: 13           moltype = DNA   length = 188
FEATURE                 Location/Qualifiers
misc_feature            1..188
                        note = PolyA-2, Bcl11a primer annealing sites flanking
                         sequence comprising five interrupting sequences separating
                         six sets of 12 consecutive adenosines
source                  1..188
                        mol_type = other DNA
                        organism = synthetic construct
SEQUENCE: 13
tcttccttca gtctgtaaac ctcagaattc atctagctcg agaaaaaatt cgaaaaaaaa    60
aaaacgtaaa aaaaaaaaac tcaaaaaaaa aaaagataaa aaaaaaaac ctaaaaaaaa   120
aaaatgtaaa aaaaaaaaag ggaaagtctt ccatatcggt tctagaccac acttcttact  180
gaggtccc                                                            188

SEQ ID NO: 14           moltype = DNA   length = 170
FEATURE                 Location/Qualifiers
misc_feature            1..170
                        note = PolyA-3, Bcl11a primer annealing sites flanking
                         sequence comprising five interrupting sequences separating
                         six sets of 12 consecutive adenosines
source                  1..170
                        mol_type = other DNA
                        organism = synthetic construct
SEQUENCE: 14
tcttccttca gtctgtaaac ctcagctcga ggaagacaag ggaaaaaaaa aaaacgcaaa    60
aaaaaaaaac acaaaaaaaa aaaatgcaaa aaaaaaaaat cgaaaaaaaa aaaatctaaa   120
aaaaaaaaac gttcatatcg gttctagacc acacttctta ctgaggtccc              170

SEQ ID NO: 15           moltype = DNA   length = 171
FEATURE                 Location/Qualifiers
```

```
misc_feature         1..171
                     note = PolyA-4, Blc11a primer annealing sites flanking
                      sequence comprising six interrupting sequences separating
                      seven sets of 12 consecutive adenosines
source               1..171
                     mol_type = other DNA
                     organism = synthetic construct
SEQUENCE: 15
tcttccttca gtctgtaaac ctcagctcga gaaaaaattc gaaaaaaaaa aaacccaaaa    60
aaaaaaaaga caaaaaaaaa aaatagaaaa aaaaaaaagt taaaaaaaaa aaactgaaaa   120
aaaaaaaatt taaaaaaaaa aaatctagac cacacttctt actgaggtcc c            171

SEQ ID NO: 16        moltype = DNA   length = 267
FEATURE              Location/Qualifiers
misc_feature         1..267
                     note = PolyA 1-2, Blc11a primer annealing sites flanking
                      sequence comprising 11 interrupting sequences separating
                      12 sets of 12 consecutive adenosines
source               1..267
                     mol_type = other DNA
                     organism = synthetic construct
SEQUENCE: 16
tcttccttca gtctgtaaac ctcagaattc atctagctcg agaaaaaaaa aaaatggaaa    60
aaaaaaaaac ggaaaaaaaa aaaggtaaaa aaaaaaaaat ataaaaaaaa aaaacataaa   120
aaaaaaaaac gaaaaaaaaa aaacgtaaaa aaaaaaaact caaaaaaaaa aaagataaaa   180
aaaaaaaacc taaaaaaaaa aaatgtaaaa aaaaaaaagg gaaagtcttc catatcggtt   240
ctagaccaca cttcttactg aggtccc                                        267

SEQ ID NO: 17        moltype = DNA   length = 261
FEATURE              Location/Qualifiers
misc_feature         1..261
                     note = PolyA 3-4, Blc11a primer annealing sites flanking
                      sequence comprising 12 interrupting sequences separating
                      13 sets of 12 consecutive adenosines
source               1..261
                     mol_type = other DNA
                     organism = synthetic construct
SEQUENCE: 17
tcttccttca gtctgtaaac ctcagctcga ggaagacaag ggaaaaaaaa aaaacgcaaa    60
aaaaaaaaac acaaaaaaaa aaaatgcaaa aaaaaaaaat cgaaaaaaaa aaaatctaaa   120
aaaaaaaaac gaaaaaaaaa aaacccaaaa aaaaaaaaga caaaaaaaaa aaatagaaaa   180
aaaaaaaagt taaaaaaaaa aaactgaaaa aaaaaaaatt taaaaaaaaa aaatctagac   240
cacacttctt actgaggtcc c                                              261

SEQ ID NO: 18        moltype = DNA   length = 370
FEATURE              Location/Qualifiers
misc_feature         1..370
                     note = 300pa, mRNA sequence of an exemplary poly-A tail
                      comprising 24 interrupting sequences separating 13 repeats
                      of 12 consecutive adenosines
source               1..370
                     mol_type = other DNA
                     organism = synthetic construct
SEQUENCE: 18
aaaaaaaaaa aatggaaaaa aaaaaaacgg aaaaaaaaaa aaggtaaaaa aaaaaaaatat    60
aaaaaaaaaa aacataaaaa aaaaaaacga aaaaaaaaaa acgtaaaaaa aaaaaaactca   120
aaaaaaaaaa agataaaaaa aaaaaaaccta aaaaaaaaaa atgtaaaaaa aaaaaagggga   180
aaaaaaaaaa acgcaaaaaa aaaaaacaca aaaaaaaaaa atgcaaaaaa aaaaaaatcga   240
aaaaaaaaaa atctaaaaaa aaaaaaacgaa aaaaaaaaaa cccaaaaaaa aaaaagacaa   300
aaaaaaaaaa tagaaaaaaa aaaaagttaa aaaaaaaaaa ctgaaaaaaa aaaaatttaa   360
aaaaaaaaaa                                                           370

SEQ ID NO: 19        moltype = DNA   length = 97
FEATURE              Location/Qualifiers
misc_feature         1..97
                     note = 100PA - sequence of an exemplary poly-A tail
                      comprising 97 adenine nucleotide homopolymer
source               1..97
                     mol_type = other DNA
                     organism = synthetic construct
SEQUENCE: 19
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaa aaaaaa                                 97

SEQ ID NO: 20        moltype = DNA   length = 20
FEATURE              Location/Qualifiers
misc_feature         1..20
                     note = pUC-M seq2 forward primer
source               1..20
```

```
                        mol_type = other DNA
                        organism = synthetic construct
SEQUENCE: 20
gggttattgt ctcatgagcg                                           20

SEQ ID NO: 21           moltype = DNA  length = 20
FEATURE                 Location/Qualifiers
misc_feature            1..20
                        note = pUC-M seq reverse primer
source                  1..20
                        mol_type = other DNA
                        organism = synthetic construct
SEQUENCE: 21
ttttgtgatg ctcgtcaggg                                           20

SEQ ID NO: 22           moltype = DNA  length = 25
FEATURE                 Location/Qualifiers
misc_feature            1..25
                        note = RN-Bcl11a for
source                  1..25
                        mol_type = other DNA
                        organism = synthetic construct
SEQUENCE: 22
tcttccttca gtctgtaaac ctcag                                     25

SEQ ID NO: 23           moltype = DNA  length = 22
FEATURE                 Location/Qualifiers
misc_feature            1..22
                        note = RN-Bcl11a rev
source                  1..22
                        mol_type = other DNA
                        organism = synthetic construct
SEQUENCE: 23
gggacctcag taagaagtgt gg                                        22

SEQ ID NO: 24           moltype = DNA  length = 4506
FEATURE                 Location/Qualifiers
misc_feature            1..4506
                        note = Liv-Udepleted: Cas9 mRNA with a poly-A tail
                         consisting of 98 consecutive adenosines
source                  1..4506
                        mol_type = other DNA
                        organism = synthetic construct
SEQUENCE: 24
tcccgcagtc ggcgtccagc ggctctgctt gttcgtgtgt gtgtcgttgc aggccttatt   60
cggatccgcc accatggaca agaagtacag catcggactg gacatcggaa caaacagcgt  120
cggatgggca gtcatcacag acgaatacaa ggtcccggac aagaagttca aggtcctggg  180
aaacacagac agacacagca tcaagaagaa cctgatcgga gcactgctgt tcgacagcgg  240
agaaacagca gaagcaacaa gactgaagag aacagcaaga agaagataca caagaagaaa  300
gaacagaatc tgctacctgc aggaaatctt cagcaacgaa atggcaaagg tcgacgcacg  360
cttcttccac agactggaag aaagcttcct ggtcgaagaa gacaagaagc acgaaagaca  420
cccgatcttc ggaaacatcg tcgacgaagt cgcataccac gaaaagtacc cgacaatcta  480
ccacctgaga aagaagctgg tcgacagcac agacaaggca gacctgagac tgatctacct  540
ggcactggca cacatgatca agttcagagg acacttcctg atcgaaggag acctgaaccc  600
ggacaacagc gacgtcgaca agctgttcat ccagctggtc cagacataca accagctgtt  660
cgaagaaaac ccgatcaacg caagcggagt cgacgcaaag gcaatcctga gcgcaagact  720
gagcaagagc agaagactgg aaaacctgat cgcacagctg ccgggagaaa agaagaacgg  780
actgttcgga aacctgatcg cactgagcct gggactgaca ccgaacttca gagcaacttc  840
cgacctggca gaagacgcaa agctgcagct gagcaaggac acatacgacg acgacctgga  900
caacctgctg gcacagatcg gagaccagta cgcagacctg ttcctggcag caaagaacct  960
gagcgacgca atcctgctga gcgacatcct gagagtcaac acagaaatca caaaggcacc 1020
gctgagcgca agcatgatca gagatacga cgaacaccac caggacctga cactgctgaa 1080
ggcactggtc agacagcagc tgccggaaaa gtacaaggaa atcttcttcg accagagcaa 1140
gaacggatac gcaggataca tcgacggagg agcaagccag gaagaattct acaagttcat 1200
caagccgatc ctggaaaaga tggacggaac agaagaactg ctggtcaagc tgaacagaga 1260
agacctgctg agaaagcaga gaacattcga caacggaagc atcccgcacc agatccacct 1320
gggagaactg cacgcaatcc tgagaagaca ggaagacttc taccgttcc tgaaggacaa 1380
cagagaaaag atcgaaaaga tcctgacatt cagaatcccg tactacgtcg gaccgctggc 1440
aagaggaaac agcagattcg catggatgac aagaaagagc gaagaaacaa tcacacctg 1500
gaacttcgaa gaagtcgtcg acaagggagc aagcgcacag agcttcatcg aaagaatgac 1560
aaacttcgac aagaacctgc cgaacgaaaa ggtcctgccg aagcacagcc tgctgtacga 1620
atacttcaca gtctacaacg aactgacaaa ggtcaagtac gtcacagaag aatgagaaa 1680
gccggcattc ctgagcggag aacagaagaa ggcaatcgtc gacctgctgt tcaagacaaa 1740
cagaaaggtc acagtcaagc agctgaagga agacttcaag aagaatgttc 1800
cagcgtcgaa atcagcggag tcgaagacag attcaacgca agcctgggaa cataccacga 1860
cctgctgaag atcatcaagg acaaggactt cctggacaac gaagaaaacg aagacatcct 1920
ggaagacatc gtcctgacac tgacactgtt cgaagacaga gaaatgatcg aagaaagact 1980
gaagacatac gcacacctgt tcgacgacaa ggtcatgaag cagctgaaga agaagaata 2040
cacaggatgg ggaagactga gcagaaagct gatcaacgga atcagagaca gcagagcgg 2100
```

```
aaagacaatc ctggacttcc tgaagagcga cggattcgca aacagaaact tcatgcagct   2160
gatccacgac gacagcctga cattcaagga agacatccag aaggcacagg tcagcggaca   2220
gggagacagc ctgcacgaac acatcgcaaa cctggcagga agcccggcaa tcaagaaggg   2280
aatcctgcag acagtcaagg tcgtcgacga actggtcaag gtcatgggaa gacacaagcc   2340
ggaaaacatc gtcatcgaaa tggcaagaga aaaccagaca acagaaggg gacagaagaa   2400
cagcagagaa agaatgaaga gaatcgaaga aggaatcaag gaactgggaa gccagatcct   2460
gaaggaaacc ccggtcgaaa acacacagct gcagaacgaa aagctgtacc tgtactacct   2520
gcagaacgga agagacatgt acgtcgacca ggaactggac atcaacgac tgagcgacta   2580
cgacgtcgac cacatcgtcc cgcagagctt cctgaaggac gacagcatcg acaacaaggt   2640
cctgacaaga agcgacaaga acagaggaaa gagcgacaac gtcccgagcg aagaagtcgt   2700
caagaagatg aagaactact ggagacagct gctgaacgca aagctgatca cacagagaaa   2760
gttcgacaac ctgacaaagg cagagagagg aggactgagc gaactggaca aggcaggatt   2820
catcaagaga cagctggtcg aaacaagaca gatcacaaag cacgtcgcac agatcctgga   2880
cagcagaatg aacacaaagt acgacaagct gatcagaaag tcaaggtcat   2940
cacactgaag agcaagctgg tcagcgactt cagaaaggac ttccagttct acaaggtcag   3000
agaaatcaac aactaccacc acgcacacga cgcatacctg aacgcagtcg tcggaacagc   3060
actgatcaag aagtacccga agctggaaag cgaattcgtc tacggagact acaaggtcta   3120
cgacgtcaga aagatgatcg caaagagcga acaggaaatc ggaaaggcaa cagcaaagta   3180
cttcttctac agcaacatca tgaacttctt caagacagaa atcacactgg caaacgaga   3240
aatcagaaaa gaccgctga tcgaaacaaa cggagaaaca ggagaaatcg tctgggacaa   3300
gggaagagac ttcgcaacag tcagaaaggt cctgagcatg ccgcaggtca acatcgtcaa   3360
gaagcacaga gtccagacag gaggattcag caaggaacgc atcctgccga agagaaacag   3420
cgacaagctg atcgcaagaa agaaggactg ggaccccgaag aagtacgag attcgcagc   3480
cccgacagtc gcatacagcg tcctggtcgt cgcaaaggtc gaaaaggaa agagcaagaa   3540
gctgaagagc gtcaaggaac tgctgggaat cacaatcatg gaaagaagca gcttcgaaaa   3600
gaacccgatc gacttcctgg aagcaaaggg atacaaggaa gtcaagaagg acctgatcat   3660
caagctgccg aagtacgacc tgttcgaact ggaaaacgga agaaagagaa tgctggcaag   3720
cgcaggagaa ctgcagaagg gaaacgaact ggcactgccg agcaagtacg tcaacttcct   3780
gtacctggca agccactacg aaaagctgaa gggaagcccg gaagacaacg aacagaagca   3840
gctgttcgtc gaacagcaca gcactacct ggacgaaatc gtcgaacaga tcagcgaatt   3900
cagcaagaga gtcatcctgg cagacgcaaa cctggacaag gtcctgagcg catacaacaa   3960
gcacagagac aagccgatca gagaacaggc agaaaacatc atccacctgt tcacactgac   4020
aaacctggga gcaccggcag cattcaagta cttcgacaca caatcgaca gaagagata   4080
cacaagcaca aaggaagtcc tggacgcaac actgatccac cagagcatca caggactgta   4140
cgaaacaaga atcgacctga gccagctggg aggagacgga ggaggaagcc cgaagaagaa   4200
gagaaaggtc tagctagcca tcacatttaa aagcatctca gcctaccatg agaataagag   4260
aaagaaaatg aagatcaata gcttattcat ctctttttct ttttcgttgg tgtaaagcca   4320
acaccctgtc taaaaaacat aaatttcttt aatcattttg cctctttct ctgtgcttca   4380
attaataaaa aatggaaaga acctcgagaa aaaaaaaaaa aaaaaaaaaa aaaaaaaaaa   4440
aaaaaaaaaa aaaaaaaaaa aaaaaaaaaa aaaaaaaaaa aaaaaaaaaa aaaaaaaaaa   4500
aaaaaa                                                               4506

SEQ ID NO: 25          moltype = DNA  length = 4512
FEATURE                Location/Qualifiers
misc_feature           1..4512
                       note = Cas9 mRNA with a poly-A tail comprising SEQ ID NO: 3
source                 1..4512
                       mol_type = other DNA
                       organism = synthetic construct
SEQUENCE: 25
tcccgcagtc ggcgtccagc ggctctgctt gttcgtgtgt gtgtcgttgc aggccttatt    60
cggatccgcc accatggaca gaagtacgac catcggactg gacatcggaa caaacagcgt   120
cggatgggca gtcatcacag acgaataaa ggtcccgagc aagaagttca aggtcctggg   180
aaacacagac agacacagca tcaagaagaa cctgatcgga gcactgctgt tcgacagcgg   240
agaaacagca gaagcaacaa gactgaagag aacagcagaa aagagatac aaggaagaaa   300
gaacagaatc tgctacctgc aggaaatctt cagcaacgaa atggcaaagg tcgacgacag   360
cttcttccac agactggaag aaagcttcct ggtcgaagaa gacaagaagc acgaaagaca   420
cccgatcttc ggaaacatcg tcgacgaagt cgcataccac gaaaagtacc cgacaatcta   480
ccacctgaga aagaagctgg tcgacagcac agacaaggca gacctgagac tgatctacct   540
ggcactggca cacatgatca agttcagagg acacttcctg atcgaaggag acctgaaccc   600
ggacaacagc gacgtcgaca agctgttcat ccagctggtc cagacataca accagctgtt   660
cgaagaaaac ccgatcaacg caagcggagt cgacgcaaag gcaatcctga cgcaagact   720
gagcaagagc agaagactgg aaaacctgat cgcacagctg ccgggagaaa agaagaacgg   780
actgttcgga aacctgatcg cactgagcct gggactgaca ccgaacttca agagcaactt   840
cgacctggca gaagacgcaa agctgcagct gagcaaggac acatacgacg acgacctgga   900
caacctgctg gcacagatcg agaccagta cgcagacctg ttcctggcag caaagaacct   960
gagcgacgca atcctgctga gcgacatcct gagagtcaac acagaaatca aaggcacc   1020
gctgagcgca agcatgatca agagatacga cgaacaccac caggacctga cactgctgaa   1080
ggcactggtc agacaagcag ctgccggaaa gtacaaggaa atcttcttcg accagagcaa   1140
gaacggatac gcaggataca tcgacggagg agcaagccag gaagaattct acaagttcat   1200
caagccgatc ctggaaaaga tggacggaac agaagaactg ctggtcaagc tgaacagaga   1260
agacctgctg agaaagcaga gaacattcga caacggaagc atcccgcacc agatccacct   1320
gggagaactg cacgcaatcc tgagaagaca ggaagacttc taccgttcc tgaaggacaa   1380
cagagaaaag atcgaaaaga tcctgacatt caatccgat tactacgtcg gaccgctgca   1440
aagaggaaac agcagattcg catgatgac aagaaagagc gaaaacaa tcacaccgtg   1500
gaacttcgaa gaagtcgtcg acaagggagc aagcgcacag agcttcatcg aaagaatgac   1560
aaacttcgaa aagaacctgc cgaacgaaaa ggtcctgccg aagcacagcc tgctgtacga   1620
atacttcaca gtctacaacg aactgacaaa ggtcaagtac gtcacagaag aatgagaaa   1680
gccggcattc ctgagcggag aacagaagaa ggcaatcgtc gacctgctgt tcaagacaaa   1740
```

```
cagaaaggtc acagtcaagc agctgaagga agactacttc aagaagatcg aatgcttcga 1800
cagcgtcgaa atcagcggag tcgaagacag attcaacgca agcctgggaa cataccacga 1860
cctgctgaag atcatcaagg acaaggactt cctggacaac gaagaaaacg aagacatcct 1920
ggaagacatc gtcctgacac tgacactgtt cgaagacaga gaaatgatcg aagaaagact 1980
gaagacatac gcacacctgt tcgacgacaa ggtcatgaag cagctgaaga gaagaagata 2040
cacaggatgg ggaagactga gcagaaagct gatcaacgga atcagagaca agcagagcgg 2100
aaagacaatc ctggacttcc tgaagagcga cggattcgca aacagaaact tcatgcagct 2160
gatccacgac gacagcctga cattcaagga agacatccag aaggcacagg tcagcggaca 2220
gggagacagc ctgcacgaac acatcgcaaa cctggcagga agcccggcaa tcaagaaggg 2280
aatcctgcag acagtcaagg tcgtcgacga actggtcaag gtcatgggaa gacacaagcc 2340
ggaaaacatc gtcatcgaaa tggcaagaga aaaccagaca acacagaagg acagaagaa 2400
cagcagagaa agaatgaaga gaatcgaaga aggaatcaag gaactgggaa gccagatcct 2460
gaaggaacac ccggtcgaaa acacacagct gcagaacgaa aagctgtacc tgtactacct 2520
gcagaacgga agagacatgt acgtcgacca ggaactggac atcaacagac tgagcgacta 2580
cgacgtcgac cacatcgtcc cgcagagctt cctgaaggac gacagcatcg acaacaaggt 2640
cctgacaaga agcgacaaga acagaggaaa gagcgacaac gtcccgagcg aagaagtcgt 2700
caagaagatg aagaactact ggagacagct gctgaacgca aagctgatca cacagagaaa 2760
gttcgacaac ctgacaaagg cagagaggg aggactgagc gaactggaca aggcaggatt 2820
catcaagaga cagctggtcg aaacaagaca gatcacaaag cacgtcgcac agatcctgga 2880
cagcagaatg aacacaaagt acgacgaaaa cgacaagctg atcagagaag tcaaggtcat 2940
cacactgaag agcaagctgg tcagcgactt cagaaaggac ttccagttct acaaggtcag 3000
agaaatcaac aactaccacc acgcacacga cgcatacctg aacgcagtcg tcggaacagc 3060
actgatcaag aagtacccga agctggaaag cgaattcgtc tacggagact acaaggtcta 3120
cgacgtcaga aagatgatcg caaagagcga acaggaaatc ggaaaggcaa cagcaaagta 3180
cttcttctac agcaacatca tgaacttctt caagacagaa atcacactgg caaacggaga 3240
aatcagaaag agaccgctga tcgaaacaaa cggagaaaca tctgggacaa 3300
gggaagagac ttcgcaacag tcagaaaggt cctgagcatg ccgcaggtca acatcgtcaa 3360
gaagacagaa gtccgacag gaggattcag caaggaaagc atcctgccga gagaaaacag 3420
cgacaagctg atcgcaagaa agaaggactg ggacccgaag aagtacgag gattcgacag 3480
cccgacagtc gcatacagcg tcctggtcgt cgcaaaggtc gaaaagggaa agagcaagaa 3540
gctgaagagc gtcaaggaac tgctgggaat cacaatcatg gaaagaagca gcttcgaaaa 3600
gaacccgatc gacttcctgg aagcaaaggg atacaaggaa gtcaagaagg acctgatcat 3660
caagctgccg aagtacagcc tgttcgaact ggaaaacgga agaaagagaa tgctggcaag 3720
cgcaggagaa ctgcagaagg gaaacgaact ggcactgccg agcaagtacg tcaacttcct 3780
gtacctggca agccactacg aaaagctgaa gggaagcccg gaagacaacg aacagaagca 3840
gctgttcgtc gaacagcaca gcactacct ggacgaaatc atcgaacaga tcagcgaatt 3900
cagcaagaga gtcatcctgg cagacgcaaa cctggacaag gtcctgagcg catacaacaa 3960
gcacagagac aagccgatca gagaacaggc agaaaacatc atccacctgt tcacactgac 4020
aaacctggga gcaccggcag cattcaagta cttcgacaca acaatcgaca gaaagagata 4080
cacaagcaca aaggaagtcc tggacgcaac actgatccac cagagcatca caggactgta 4140
cgaaacaaga atcgacctga ccagctggg aggagacgga ggaggaagcc cgaagaagaa 4200
gagaaaggtc tagctagcca tcacatttaa aagcatctcg gcctaccatg agaataagag 4260
aaagaaaatg aagatcaata gcttattcat ctctttttct ttttcgttgg tgtaaagcca 4320
acaccctgtc taaaaaacat aaatttcttt aatcattttg cctctttcct ctgtgcttca 4380
attaataaaa aatggaaaga accaaaaaaa aaaaaaaaaa aaaaaaaagc gaaaaaaaaa 4440
aaaaaaaaaa aaaaaaccga aaaaaaaaaa aaaaaaaaa aaaagtgaaa aaaaaaaaaa 4500
aaaaaaaaaa aa                                                    4512

SEQ ID NO: 26          moltype = DNA   length = 4504
FEATURE                Location/Qualifiers
misc_feature           1..4504
                       note = Cas9 mRNA with a poly-A tail comprising SEQ ID NO: 4
source                 1..4504
                       mol_type = other DNA
                       organism = synthetic construct
SEQUENCE: 26
tcccgcagtc ggcgtccagc ggctctgctt gttcgtgtgt gtgtcgttgc aggccttatt 60
cggatccgcc accatggaca agaagtacag catcggactg gacatcggaa caaacagcgt 120
cggatgggca gtcatcacag acgaaataca aggtcccgagc aagaagttca aggtcctggg 180
aaacacagac agacacagca tcaagaagaa cctgatcgga gcactgctgt tcgacagcgg 240
agaaacagca gaagcaacaa gactgaagag aacagcaaga agaagatata caagaagaaa 300
gaacagaatc tgctacctgc aggaaatctt cagcaacgaa atggcaaagg tcgacgacag 360
cttcttccac agactggaag aaagcttcct ggtcgaagaa gacaagaagc acgaaagaca 420
cccgatcttc ggaaacatcg tcgacgaagt cgcatccac cagcaatctga 480
ccacctgaga aagaagctgg tcgacagcac agacaaggca gacctgagac tgatctacct 540
ggcactggca cacatgatca agttcagagg acacttcctg atcgaaggag acctgaaccc 600
ggacaacagc gacgtcgaca agctgttcat ccagctggtc cagacataca accagctgtt 660
cgaagaaaac ccgatcaacg caagcggagt cgacgcaaaa gcaatcctga gcgcaagact 720
gagcaagagc agaagactgg aaaacctgat cgcacagctg ccgggagaaa agaagaacgg 780
actgttcgga aacctgatcg cactgagcct gggactgaca ccgaacttca agagcaactt 840
cgacctggca gaagacgcaa agctgcagct gagcaaggac acatacgacg acgacctgga 900
caacctgctg gcacagatcg agaccagta cgcagacctg ttcctggcag caagaaacct 960
gagcgacgca atcctgctga gcgacatcct gagagtcaac acagaaatca aaaggcacc 1020
gctgagcgca agcatgatca gagatacga cgaaccacga cgacctga cactgctgaa 1080
ggcactggtc agacagcagc tgccggaaa gtacaaggaa atcttcttcg accagagcaa 1140
gaacggatac gcaggataca tcgacggagg agcaagccag gaagaattct acagttcat 1200
caagccgatc ctgaaaaaga tggacggaac agaagaactg ctggtcaagc tgaacagaga 1260
agacctgctg agaaagcaga gaacattcga caacggaagc atcccgcacc agatccacct 1320
gggagaactg cacgcaatcc tgagaagaca ggaagacttc taccggttcc tgaaggacaa 1380
```

```
cagagaaaag atcgaaaaga tcctgacatt cagaatcccg tactacgtcg gaccgctggc   1440
aagaggaaac agcagattcg catggatgac aagaaagagc gaagaaacaa tcacaccgtg   1500
gaacttcgaa gaagtcgtcg acaagggagc aagcgcacag agcttcatcg aaagaatgac   1560
aaacttcgac aagaacctgc cgaacgaaaa ggtcctgccg aagcacagcc tgctgtacga   1620
atacttcaca gtctacaacg aactgacaaa ggtcaagtca gtcacagaag gaatgagaaa   1680
gccggcattc ctgagcggag aacagaagaa ggcaatcgtc gacctgctgt tcaagacaaa   1740
cagaaaggtc acagtcaagc agctgaagga agactacttc aagaagatcg aatgcttcga   1800
cagcgtcgaa atcagcggag tcgaagacag attcaacgca agcctgggaa cataccacga   1860
cctgctgaag atcatcaagg acaaggactt cctggacaac gaagaaaacg aagacatcct   1920
ggaagacatc gtcctgacac tgacactgtt cgaagacaga gaaatgatcg aagaaagact   1980
gaagacatac gcacacctgt tcgacgacaa ggtcatgaag cagctgaaga agaagaagata   2040
cacaggatgg ggaagactga gcagaaagct gatcaacgga atcagagaca agcagagcgg   2100
aaagacaatc ctggacttcc tgaagagcga cggattcgca aacagaaact tcatgcagct   2160
gatccacgac gacagcctga cattcaagga agacatccag aaggcacagg tcagcggaca   2220
gggagacagc ctgcacgaac acatcgcaaa cctggcagga agcccggcaa tcaagaaggg   2280
aatcctgcag acagtcaagg tcgtcgacga actggtcaag gtcatgggaa gacacaagcc   2340
ggaaaacatc gtcatcgaaa tggcaagaga aaaccagaca acacgaaagg gacagaagaa   2400
cagcagagaa agaatgaaga atcagaaga aggaatcgaga gaactgggaa gccagatcct   2460
gaaggaacac ccggtcgaaa acacacagct gcagaacgaa aagctgtacc tgtactacct   2520
gcagaacgga agagacatgt acgtcgacca ggaactggac atcaacgacc tgagcgacta   2580
cgacgtcgac cacatcgtcc cgcagagctt cctgaaggac gacagcatcg acaacaaggt   2640
cctgacaaga agcgacaaga acagaggaaa gagcgacaac gtcccgagcg aagaagtcgt   2700
caagaagatg aagaactact ggagacagct gctgaacgca aagctgatca cagagagaaa   2760
gttcgacaac ctgacaaagg cagagagagg aggactgagc gaactggaca aggcaggatt   2820
catcaagaga cagctggtcg aaacaagaca gatcacaaag cacgtcgcac agatcctgga   2880
cagcagaatg aacacaaagt acgacgaaaa cgacaagctg atcagagaag tcaaggtcat   2940
cacactgaag agcaagctgg tcagcgactt cagaaaggac ttccagttct acaaggtcag   3000
agaaatcaac aactaccacc acgcacacga cgcataccctg aacgcagtcg tcggaacagc   3060
actgatcaag aagtacccga agctggaaag cgaattcgtc tacggagact acaaggtcta   3120
cgacgtcaga aagatgatcg caaagagcga acaggaaatc ggaaaggcaa cagcaaagta   3180
cttcttctac agcaacatca tgaacttctt caagacagaa atcacactgg caaacgaga   3240
aatcagaaag agaccgctga tcgaaacaaa cggagaaaca ggagaaatcg tctgggacaa   3300
gggaagagac ttcgcaacag tcagaaaggt cctgagcatg ccgcaggtca acatcgtcaa   3360
gaagacagaa gtccagacag aggattcag caaggaaagc atcctgccga agaaaacga   3420
cgacaagctg atcgcaagaa agaaggactg ggacccagaa aagtacggag gattcgacag   3480
cccgacagtc gcatcagcg tcctggtcgt cgcaaaggtc gaaaagggaa agagcaagaa   3540
gctgaagagc gtcaaggaac tgctgggaat cacaatcatg gaagaagca gcttcgaaaa   3600
gaaccgatc gacttcctgg aagcaaaggg atacaaggaa gtcaagaagg acctgatcat   3660
caagctgccg aagtacagcc tgttcgaact ggaaaacgga agagaagaa tgctggcaag   3720
cgcaggagaa ctgcagaagg aaacgaact ggcactgccg agcaagtacg tcaacttcct   3780
gtacctggca agccactacg aaaagctgaa gggaagcccg aagacaacg aacagaagca   3840
gctgttcgtc aacagcaca agcactacct ggacgaaatc atcgaacaga tcagcgaatt   3900
cagcaagaga gtcatcctgg cagacgcaaa cctggacaag gtcctgagcg catacaacaa   3960
gcacagagac aagccgatca gagaacaggc agaaaacatc atccacctgt tcacactgac   4020
aaacctggga gcaccggcag cattcaagta cttcgacaca caatcgaca gaaagagata   4080
cacaagcaca aaggaagtcc tggacgcaac actgatccac cagagcatca caggactgta   4140
cgaaacaaga atcgacctga gccagctggg aggagacgga agaaggaagcc cgaagaagaa   4200
gagaaaggtc tagctagcca tcacatttaa aagcatctca gcctaccatg agaataagag   4260
aaagaaaatg aagatcaata gcttattcat ctcttttct ttttcgttgg tgtaaagcca   4320
acaccctgtc taaaaacat aaatttcttt aatcattttg cctctttct ctgtgcttca   4380
attaataaaa aatggaaaga accaaaaaaa aaaaaaaag aaaaaaaaaa aaaaaacaaa   4440
aaaaaaaaaa aaataaaaaa aaaaaaaaaa taaaaaaaaa aaaaaacaa aaaaaaaaa   4500
aaaa                                                               4504
SEQ ID NO: 27            moltype = DNA  length = 4568
FEATURE                  Location/Qualifiers
misc_feature             1..4568
                         note = Cas9 mRNA with a poly-A tail comprising SEQ ID NO: 5
source                   1..4568
                         mol_type = other DNA
                         organism = synthetic construct
SEQUENCE: 27
tcccgcagtc ggcgtccagc ggctctgctt gttcgtgtgt gtgtcgttgc aggccttatt     60
cggatccgcc accatggaca agaagtacag catcggactg gacatcggaa caaacagcgt    120
cggatgggca gtcatcacag acgaatacaa ggtcccgagc aagaagttca ggtcctggg     180
aaacacagac agacacagca tcaagaagaa cctgatcgga gcactgctgt tcgacagcgg    240
agaaacagca gaagcaacaa gactgaagag aacagcaaga agaagataca caagaagaaa    300
gaacagaatc tgctacctgc aggaaatctt cagcaacgaa atggcaaagg tcgacgacag    360
cttcttccac agactggaag aaagcttcct ggtcgaagaa gacaagaagc acgaaagaca    420
cccgatcttc ggaaacatcg tcgacgaagt cgcataccac gaaaagtacc cgacaatcta    480
ccacctgaga aagaagctgg tcgacagcac agacaaggca gacctgagac tgatctacct    540
ggcactggca cacatgatca agttcagagg acacttcctg atcgaggag acctgaaccc    600
ggacaacagc gacgtcgaca agctgttcat ccagctggtc cagacataca accagctgtt    660
cgaagaaaac cgatcaaacg caagggagt cgacgcaaaa atcctgagcg cgcaagact    720
gagcaagagc agaagactgg aaaacctgat cgcacagctg ccgggagaaa agaagaacgg    780
actgttcgga aacctgatcg cactgagcct gggactgaca ccgaacttca agagcaactt    840
cgacctggca gaagacgcaa agctgcagct gagcaaggac acatacgacg acgacctgga    900
caacctgctg gcacagatcg agaccagta cgcagacctg ttcctggcag caaagaacct    960
gagcgacgca atcctgctga gcgacatcct gagagtcaac acagaaatca aaaggcacc   1020
```

```
gctgagcgca agcatgatca agagatacga cgaacaccac caggacctga cactgctgaa  1080
ggcactggtc agacagcagc tgccggaaaa gtacaaggaa atcttcttcg ccagagcaa  1140
gaacggatac gcaggataca tcgacggagg agcaagccag gaagaattct acaagttcat  1200
caagccgatc ctggaaaaga tggacggaac agaagaactg ctggtcaagc tgaacagaga  1260
agacctgctg agaaagcaga gaacattcga caacggcacg atcccgcacc agatccacct  1320
gggagaactg cacgcaatcc tgagaagaca ggaagacttc tacccgttcc tgaaggacaa  1380
cagagaaaag atcgaaaaga tcctgacatt cagaatcccg tactacgtcg gaccgctggc  1440
aagaggaaac agcagattcg catggatgac aagaaagagc gaagaaacaa tcacaccgtg  1500
gaacttcgaa gaagtcgtcg acaagggagc aagcgcacag agcttcatcg aaagaatgac  1560
aaacttcgac aagaacctgc cgaacgaaaa ggtcctgccg aagcacagcc tgctgtacga  1620
atacttcaca gtctacaacg aactgacaaa ggtcaagtac gtcacagaag aatgagaaa  1680
gccggcattc tgagcggag aacagaagaa ggcaatcgtc gacctgctgt tcaagacaaa  1740
cagaaaggtc acagtcaagc agctgaagga agactacttc aagaagatcg aatgcttcga  1800
cagcgtcgaa agactacttc gaagacag attcaacgca agcctgggaa cataccacga  1860
cctgctgaag atcatcaagg acaaggactt cctggacaac gaagaaaacg aagcatcct  1920
ggaagacatc gtcctgacac tgacactgtt cgaagacaga gaaatgatcg aagaaagact  1980
gaagacatac gcacacctgt tcgacgacaa ggtcatgaag cagctgaaga agagaagata  2040
cacaggatgg ggaagactga gcagaaagct gatcaacgga atcagagaca agcagagcgg  2100
aaaagacaatc ctggacttcc tgaagagcga cggattcgca aacagaaact tcatgcagct  2160
gatccacgac gacagcctga cattcaagga agacatccag aaggcacagg tcagcggaca  2220
gggagacagc ctgcacgaac acatcgcaaa cctggcagga agcccggcaa tcaagaaggg  2280
aatcctgcag acagtcaagg tcgtcgacga actggtcaag gtcatgggaa gacacaagcc  2340
ggaaaacatc gtcatcgaaa tggcaagaga aaaccagaca acacagaagg acagaagaa  2400
cagcagagaa agaatgaaga aatcgaaga aggaatcaag gaactgggaa gccagatcct  2460
gaaggaacac ccggtcgaaa cacacagct gcagaacgaa aagctgtacc tgtactacct  2520
gcagaacgga agagacatgt acgtcgacca ggaactggac atcaacagac tgagcgacta  2580
cgacgtcgac cacatcgtcc cgcagagctt cctgaaggac gacagcatcg acaacaaggt  2640
cctgacaaga agcgacaaga acagaggaaa gagcgacaac gtcccgagcg aagaagtcgt  2700
caagaagatg aagaactact ggagacagct gctgaacgca agctgatca cacagagaaa  2760
gttcgacaac ctgacaaagg cagagagg aggactgagc gaactggaca agaggcaggatt  2820
catcaagaga cagctggtcg aaacaagaca gatcacaaag cacgtcgcac agatcctgga  2880
cagcagaatg aacacaaagt acgacgaaaa cgacaagctg atcagagaag tcaaggtcat  2940
cacactgaag agcaagctgg tcagcgactt cagaaaggac ttccagttct acaaggtcag  3000
agaaatcaac aactaccacc acgcacacga cgcatacctg aacgcagtcg tcggaacagc  3060
actgatcaag aagtacccga agctggaaag cgaattcgtc tacggagact acaaggtcta  3120
cgacgtcaga aagatgatcg caaagagcga acaggaaatc ggaaaggcaa cagcaaagta  3180
cttcttctac agcaacatca tgaacttctt caagacagaa atcacactgg caaacggaga  3240
aatcagaaag agaccgctga tcgaaacaaa cggagaaaca ggagaaatcg tctgggacaa  3300
gggaagagac ttcgcaacag tcagaaaggt cctgagcatg ccgcaggtca acatcgtcaa  3360
gaagacagaa gtccgacag gaggattcag caaggaaagc atcctgccga gagaaacaga  3420
cgacaagctg atcgcaagaa agaaggactg ggacccgaag aagtacgag gattcgacag  3480
cccgacagtc gcatacagcg tcctggtcgt cgcaaaggtc gaaagggaaa gagcaagaa  3540
gctgaagaga gtcaaggaac tgctgggaat cacaatcatg gaaagaagcc gcttcgaaaa  3600
gaacccgatc gacttcctgg aagcaaaggg atacaaggaa gtcaagaagg acctgatcat  3660
caagctgccg aagtacagcc tgttcgaact ggaaaacgga agaaagagaa tgctggcaag  3720
cgcaggagaa ctgcagaagg aaacgaact ggcactgccg agcaagtacg tcaacttcct  3780
gtacctggca agcactacg aaaagctggca gggaagccc gaagacaacg aacagaagca  3840
gctgttcgtc gaacagcaca agcactacct ggacgaaatc atcgaacaga tcagcgaatt  3900
cagcaagaga gtcatcctgg cagacgcaaa cctggacaag gtcctgagcg catacaacaa  3960
gcacagagac aagccgatca gagaacaggc agaaaacatc atccacctgt tcacactgac  4020
aaacctggga gcaccggcag cattcaagta cttcgacaca acaatcgaca gaaagagata  4080
cacaagcaca aaggaagtcc tggacgcaac actgatccac cagagcatca caggactgta  4140
cgaaacaaga atcgacctga ccagctggg aggacgga ggaggaagcc gaagaagaa  4200
gagaaaggtc tagctagcca tcacatttaa agcatctca gcctaccatg agaataagag  4260
aaagaaaatg aagatcaata gcttattcat ctctttttct ttcgttgg tgtaaagcca  4320
acaccctgtc taaaaacat aaatttcttt aatcattttg cctcttttct ctgtgcttca  4380
attaataaaa aatggaaaga accaaaaaaa aaaaaaaag aaaaaaaaaa aaaaacaaa  4440
aaaaaaaaaa aaataaaaaa aaaaaaaaaa taaaaaaaaa aaaaaacaa aaaaaaaaa  4500
aaaacaaaaa aaaaaaaaaa aaaaaaaaaa aaaaaaaaa aaaaaaaaa aaaaaaaaaa  4560
aaaaaaaa                                                          4568

SEQ ID NO: 28         moltype = DNA   length = 4519
FEATURE               Location/Qualifiers
misc_feature          1..4519
                      note = Cas9 mRNA with a poly-A tail comprising SEQ ID NO: 10
source                1..4519
                      mol_type = other DNA
                      organism = synthetic construct
SEQUENCE: 28
tcccgcagtc ggcgtccagc ggctctgctt gttcgtgtgt gtgtcgttgc aggccttatt   60
cggatccgcc accatggaca agaagtacag catcggactg gacatcggaa caaacagcgt  120
cggatgggca gtcatcacag acgaatacaa ggtcccgagc aagaagttca ggtcctggg  180
aaacacagac agacacagca tcaagaagaa cctgatcgga gcactgctgt tcgacagcgg  240
agaaacagca gaagcaacaa gactgaagag aacagcaaga agagataca caagaagaaa  300
gaacagaatc tgctacctgc aggaaatctt cagcaacgaa atggcaaagg tcgacgacag  360
cttcttccac agactggaag aaagcttcct ggtcgaagaa gacaagaagc acgaaagaca  420
cccgatcttc ggaaacatcg tcgacgaagt cgcataccac gaaaagtacc cgacaatcta  480
ccacctgaga aagaagctgg tcgacagcac agacaaggca gacctgagac tgatctacct  540
ggcactggca cacatgatca agttcagagg acacttcctg atcgaaggag acctgaaccc  600
```

```
ggacaacagc gacgtcgaca agctgttcat ccagctggtc cagacataca accagctgtt    660
cgaagaaaac ccgatcaacg caagcggagt cgacgcaaag gcaatcctga gcgcaagact    720
gagcaagagc agaagactgg aaaacctgat cgcacagctg ccgggagaaa agaagaacgg    780
actgttcgga aacctgatcg cactgagcct gggactgaca ccgaacttca agagcaactt    840
cgacctggca gaagacgcaa agctgcagct gagcaaggac acatacgacg acgacctgga    900
caacctgctg gcacagatcg gagaccagta cgcagacctg ttcctggcag caaagaacct    960
gagcgacgca atcctgctga gcgacatcct gagagtcaac acagaaatca caaaggcacc   1020
gctgagcgca agcatgatca agagatacga cgaacaccac caggacctga cactgctgaa   1080
ggcactggtc agacagcagc tgccggaaaa gtacaaggaa atcttcttcg accagagcaa   1140
gaacggatac gcaggataca tcgacggagg agcaagccag gaagaattct acaagttcat   1200
caagccgatc ctggaaaaga tggacggaac agaagaactg ctggtcaagc tgaacagaga   1260
agacctgctg agaaagcaga gaacattcga caacggaagc atcccgcacc agatccacct   1320
gggagaactg cacgcaatcc tgagaagaca ggaagacttc taccgttcc tgaaggacaa    1380
cagagaaaag atcgaaaaga tcctgacatt cagaatcccg tactacgtcg gaccgctggc   1440
aagaggaaac agcagattcg catggatgac aagaaagagc gaagaaacaa tcacaccgtg   1500
gaacttcgaa gaagtcgtcg acaagggagc aagcgcacag agcttcatcg aaagaatgac   1560
aaacttcgac aagaacctgc cgaacgaaaa ggtcctgccg aagcacagcc tgctgtacga   1620
atacttcaca gtctacaacg aactgacaaa ggtcaagtac gtcacagaag gaatgagaaa   1680
gccggcattc ctgagcggag aacagaagaa ggcaatcgtc gacctgctgt tcaagacaaa   1740
cagaaaggtc acagtcaagc agctgaagga agactactt aagaagatcg aatgcttcga    1800
cagcgtcgaa atcagcggag tcgaagacag attcaacgca agcctgggaa cataccacga   1860
cctgctgaag atcatcaagg acaaggactt cctggacaac gaagaaaacg aagacatcct   1920
ggaagacatc gtcctgacac tgacactgtt cgaagacaga gaaatgatcg aagaaagact   1980
gaagacatac gcacacctgt tcgacgacaa ggtcatgaag cagctgaaga agaagatca    2040
cacaggatgg ggaagactga gcagaaagct gatcaacgga atcagagaca agcagagcgg   2100
aaagacaatc ctggacttcc tgaagagcga cggattcgca aacagaaact tcatgcagct   2160
gatccacgac gacagcctga cattcaagga agacatccag aaggcacagg tcagcggaca   2220
gggagacagc ctgcacgaac acatcgcaaa cctggcagga agcccggcaa tcaagaaggg   2280
aatcctgcag acagtcaagg tcgtcgacga actggtcaag gtcatgggaa gacacaagcc   2340
ggaaaacatc gtcatcgaaa tggcaagaga aaaccagaca acacaggaag gacagaagaa   2400
cagcagagaa agaatgaaga gaatcgaaga aggaatcaag gaactgggaa gccagatcct   2460
gaaggaacac ccggtcgaaa acacacagct gcagaacgaa aagctgtacc tgtactacct   2520
gcagaacgga gagacatgt acgtcgacca ggaactggac atcaacgac tgagcgacta    2580
cgacgtcgac cacatcgtcc cgcagagctt cctgaaggac gacagcatcg acaacaaggt   2640
cctgacaaga agcgacaaga acagaggaaa gagcgacaac gtcccgagcg aagaagtcgt   2700
caagaagatg aagaactact ggagacagct gctgaacgca aagctgatca cacagagaaa   2760
gttcgacaac ctgacaaagg cagagagagg aggactgagc gaactggaca aggcaggatt   2820
catcaagaga cagctggtcg aaacaagaca gatcacaaag cacgtcgcac agatcctgga   2880
cagcagaatg aacacaaagt acgacgaaaa cgacaagctg atcagagaag tcaaggtcat   2940
cacactgaag agcaagctgg tcagcgactt cagaaaggac ttccagttct acaaggtcag   3000
agaaatcaac aactaccacc acgcacacga cgcataccg aacgcagtcg tcggaacagc    3060
actgatcaag aagtacccga agctggaaag cgaattcgtc tacggagact acaaggtcta   3120
cgacgtcaga aagatgatcg caaagagcga acaggaaatc ggaaaggcaa cagcaaagta   3180
cttcttctac agcaacatca tgaacttctt caagacagaa atcacactgg caaacgaga   3240
aatcagaaag agaccgctga tcgaaacaaa cggagaaaca ggagaaatcg tctgggacaa   3300
gggaagagac ttcgcaacag tcagaaaggt cctgagcatg ccgcaggtca catcgtcaa    3360
gaagacagaa gtccagacag gaggattcag caaggaaagc atcctgccga agagaaacag   3420
cgacaagctg atcgcaagaa agaaggactg gacccgaag aagtacgag gattcgacag    3480
cccgacagtc gcatacagcg tcctggtcgt cgcaaaggtc gaaaaggaa agagcaagaa   3540
gctgaagagc gtcaaggaac tgctgggaat cacaatcatg gaaagaagca gcttcgaaaa   3600
gaacccgatc gacttcctgg aagcaaaggg atacaaggaa gtcaagaagg acctgatcat   3660
caagctgccg aagtacagcc tgttcgaact ggaaaacgga gaaaagagaa tgctggcaag   3720
cgcaggagaa ctgcagaagg gaaacgaact ggcactgccg agcaagtacg tcaacttcct   3780
gtacctggca agcactacg aaaagctgaa gggaagcccg gaagacaacg aacagaagca    3840
gctgttcgtc gaacagcaca agcactacct ggacgaaatc atcgaacaga tcagcgaatt   3900
cagcaagaga gtcatcctgg cagacgcaaa cctggacaag gtcctgagcg catacaacaa   3960
gcacagagac aagccgatca gaaacaggc agaaaacatc atccacctgt tcacactgac    4020
aaacctggga gcaccggcag cattcaagta cttcgacaca acatcgaca gaaagagata    4080
cacaagcaca aaggaagtcc tggacgcaac actgatccac cagagcatca caggactgta   4140
cgaaacaaga atcgacctga gccagctggg aggagacgga ggaggaagcc cgaagaagaa   4200
gagaaaggtc tagctagcca tcacatttaa aagcatctca gcctaccatg agaataagag   4260
aaagaaaatg aagatcaata gcttattcat ctcttttct ttttcgttgg tgtaaagcca    4320
acaccctgtc taaaaaacat aaatttcttt aatcattttg cctcttttct ctgtgcttca   4380
attaataaaa aatggaaaga accaaaaaaa aaaataaaa aaaaaaata aaaaaaaaa      4440
acaaaaaaaa aaaataaaa aaaaaacaa aaaaaaaa gaaaaaaaa aaacaaaaaa        4500
aaaaaataaa aaaaaaaaa                                                4519

SEQ ID NO: 29       moltype = DNA  length = 4518
FEATURE             Location/Qualifiers
misc_feature        1..4518
                    note = Cas9 mRNA with a poly-A tail comprising SEQ ID NO: 11
source              1..4518
                    mol_type = other DNA
                    organism = synthetic construct
SEQUENCE: 29
tcccgcagtc ggcgtccagc ggctctgctt gttcgtgtgt gtgtcgttgc aggccttatt     60
cggatccgcc accatggaca agaagtacag catcggactg gacatcggaa caaacagcgt   120
cggatgggca gtcatcacag acgaatacaa ggtcccgagc aagaagttca ggtcctggg    180
aaacacagac agacacagca tcaagaagaa cctgatcgga gcactgctgt tcgacagcgg   240
```

```
agaaacagca gaagcaacaa gactgaagag aacagcaaga agaagataca caagaagaaa    300
gaacagaatc tgctacctgc aggaaatctt cagcaacgaa atggcaaagg tcgacgacag    360
cttcttccac agactggaag aaagcttcct ggtcgaagaa gacaagaagc acgaaagaca    420
cccgatcttc ggaaacatcg tcgacgaagt cgcataccac gaaaagtacc cgacaatcta    480
ccacctgaga aagaagctgg tcgacagcac agacaaggca gacctgagac tgatctacct    540
ggcactggca cacatgatca agttcagagg cacttcctg atcgaaggag acctgaaccc     600
ggacaacagc gacgtcgaca agctgttcat ccagctggtc cagacataca accagctgtt    660
cgaagaaaac ccgatcaacg caagcggagt cgacgcaaag gcaatcctga cgcaagact     720
gagcaagagc agaagactgg aaaacctgat cgcacacgtc ccgggagaaa agaagaacgg    780
actgttcgga aacctgatcg cactgagcct gggactgaca ccgaacttca agagcaactt    840
cgacctggca gaagacgcaa agctgcagct gagcaaggac acatacgacg acgacctgga    900
caacctgctg gcacagatcg gagaccagta cgcagacctg ttcctggcag caaagaacct    960
gagcgacgca atcctgctga cgacatcct gagagtcaac acagaaatca caaaggcacc   1020
gctgagcgca agcatgatca agagatacga cgaaccacc caggacctga cactgctgaa   1080
ggcactggtc agacagcagc tgccggaaaa gtacaaggaa atcttcttcg accagagcaa   1140
gaacggatac gcaggataca tcgacggagg agcaagccag gaagaattct acaagttcat   1200
caagcccgatc ctgaaaaaga tggacggaac agaagaactg ctggtcaagc tgaacagaga   1260
agacctgctg agaaagcaga gaacattcga caacggaagc atcccgcacc agatccacct   1320
gggagaactg cacgcaatcc tgagaagaca ggaagacttc tacccgttcc tgaaggacaa   1380
cagagaaaag atcgaaaaga tcctgacatt cagaatcccg tactacgtcg accgctggc   1440
aagaggaaac agcagattcg catggatgac aagaaagagc gaagaaacaa tcacaccgtg   1500
gaacttcgaa gaagtcgtcg acaagggagc aagcgcacag agcttcatcg aaagaatgac   1560
aaacttcgac aagaacctgc cgaacgaaaa ggtcctgccg aagcacagcc tgctgtacga   1620
atacttcaca gtctacaacg aactgacaaa ggtcaagtac gtcacagaag aatgagaaa   1680
gccggcattc ctgagcggag aacagaagaa ggcaatcgtc gacctgctgt tcaagacaaa   1740
cagaaaggtc acagtcaagc agctgaagga agactacttc aagaagatcg aatgcttcga   1800
cagcgtcgaa atcagcggag tcgaagacag attcaacgca agcctgggaa cataccacga   1860
cctgctgaag atcatcaagg acaaggactt cctggacaac gaagaaaacg aagacatcct   1920
ggaagacatc gtcctgacac tgacactgtt cgaagacaga gaaatgatcg aagaaagact   1980
gaagacatac gcacacctgt tcgacgacaa ggtcatgaag cagctgaaga agagaagata   2040
cacaggatgg ggaagactga gcagaaagct gatcaacgga atcagagaca agcagagcgg   2100
aaagacaatc ctggacttcc tgaagagcga cggattcgca aacagaaact tcatgcagct   2160
gatccacgac gacagcctga cattcaagga agacatccag aaggcacagg tcagcggaca   2220
gggagacagc ctgcacgaac acatcgcaaa cctggcagga agcccggcaa tcaaagaaggg   2280
aatcctgcag acagtcaagg tcgtcgacga actggtcaag gtcatgggaa gacacaagcc   2340
ggaaaacatc gtcatcgaaa tggcaagaga aaaccagaca acagaaggg gacagaagaa   2400
cagcagagaa agaatgaaga gaatcgaaga aggaatcaag gaactgggaa gccagatcct   2460
gaaggaacac ccggtcgaaa acacacagct gcagaacgaa aagctgtacc tgtactacct   2520
gcagaacgga agagacatgt acgtcgacca ggaactgaca atcaacagac tgagcgacta   2580
cgacgtcgac cacatcgtcc cgcagagctt cctgaaggac gacagcatcg acaacaaggt   2640
cctgacaaga agcgacaaga acagaggaaa gagcgacaac gtcccgagcg aagaagtcgt   2700
caagaagatg aagaactact ggagacagct gctgaacgca aagctgatca cacagagaaa   2760
gttcgacaac ctgacaaagg cagagagagg aggactggac gaactggaca agagcaggatt   2820
catcaagaga cagctggtcg aaacaagaca gatcacaaag cacgtcgcac agatcctgga   2880
cagcagaatg aacacaaagt acgacgaaaa cgacaagctg atcagagaag tcaaggtcat   2940
cacactgaag agcaagctgg tcagcgactt cagaaaggac ttccagttct acaaggtcag   3000
agaaatcaac aactaccacc acgcacacga cgcatacctg aacgcagtct cggaacagc   3060
actgatcaag aagtacccga agctggaaag cgaattcgtc tacgagact acaaggtcta   3120
cgacgtcaga aagatgatcg caaagagcga acaggaaatc ggaaaggcaa cagcaaagta   3180
cttcttctac agcaacatca tgaacttctt caagacagaa atcacactgg caaacggaga   3240
aatcagaaag agaccgctga tcgaaacaaa cggagaaaca tcgacggaaa tcg tctgggacaa   3300
gggaagagac ttcgcaacag tcagaaaggt cctgagcatg ccgcaggtca acatcgtcaa   3360
gaagacagaa gtccagacag gaggattcag caaggaaagc atcctgccga agagaaacag   3420
cgacaagctg atcgcaagaa agaaggactg ggacccgaag aagtacgag gattcgacag   3480
cccgacagtc gcatacagcg tcctggtcgt cgcaaaggtc gaaaaggg aagacaagaa   3540
gctgaagagc gtcaaggaac tgctgggaat cacaatcatg gaaagaagca gcttcgaaaa   3600
gaacccgatc gacttcctgg aagcaaaggg atacaaggaa gtcaagaagg acctgatcat   3660
caagctgccg aagtacagcc tgttcgaact ggaaaacgga agaaagagaa tgctggcaag   3720
cgcaggagaa ctgcagaagg gaaacgaact ggcactgccg agcaagtacg tcaacttcct   3780
gtacctggca agccactacg aaaagctgaa gggaagccg gaagacaacg aacagaagca   3840
gctgttcgtc gaacagcaca agcactacct ggacgaaatc atcgaacaga tcagcgaatt   3900
cagcaagaga gtcatcctgg cagacgcaaa cctggacaag gtcctgagcg catacaacaa   3960
gcacagagac aagccgatca gagaacagg agaaaacatc atcccacctgt tcacactgac   4020
aaacctggga gcaccggcag cattcaagta cttcgacaca caatcgaca gaaagcagta   4080
cacaagcaca aaggaagtcc tggacgcaac actgatccac cagagcatca caggactgta   4140
cgaaacaaga atcgacctga ccagctgggg aggacgga ggaggaagcc cgaagaagaa   4200
gagaaaggtc tagctagcca tcacatttaa agcatctca gcctaccatg agaataagag   4260
aaagaaaatg aagatcaata gcttattcat ctctttttct ttttcgttgg tgtaaagcaa   4320
acaccctgtc taaaaaacat aaatttcttt aatcattttg cctcttttct ctgtgcttca   4380
attaataaaa aatggaaaga accaaaaaaa ataaaaaaaa taaaaaaaac aaaaaaaaa   4440
aaaaagaaa aaaataaaa aaaacaaaaa aaacaaaaaa aataaaaaaa agaaaaaaaa   4500
caaaaaaaat aaaaaaaa                                                4518
```

SEQ ID NO: 30        moltype = DNA  length = 4500
FEATURE               Location/Qualifiers
misc_feature      1..4500
                      note = Cas9 mRNA with a poly-A tail comprising SEQ ID NO: 19
source                1..4500
                      mol_type = other DNA organism = synthetic construct
SEQUENCE: 30

```
tcccgcagtc ggcgtccagc ggctctgctt gttcgtgtgt gtgtcgttgc aggccttatt   60
cggatccgcc accatggaca agaagtacag catcggactg gacatcggaa caaacagcgt  120
cggatgggca gtcatcacag acgaatacaa ggtcccgagc aagaagttca aggtcctggg  180
aaacacagac agacacagca tcaagaagaa cctgatcgga gcactgctgt tcgacagcgg  240
agaaacagca gaagcaacaa gactgaagag aacagcaaga agaagataca caagaagaaa  300
gaacagaatc tgctacctgc aggaaatctt cagcaacgaa atggcaaagg tcgacgcacg  360
cttcttccac agactggaag aaagcttcct ggtcgaagaa gacaagaagc acgaaagaca  420
cccgatcttc ggaaacatcg tcgacgaagt cgcataccac gaaaagtacc cgacaatcta  480
ccacctgaga aagaagctgg tcgacagcac agacaaggca gacctgagac tgatctacct  540
ggcactggca cacatgatca agttcagagg acacttcctg atcgaaggag acctgaaccc  600
ggacaacagc gacgtcgaca agctgttcat ccagctggtc cagacataca accagctgtt  660
cgaagaaaac ccgatcaacg caagcggagt cgacgaagca caatcctgac gcgcaagact  720
gagcaagagc agaagactgg aaaacctgat cgcacagctg ccgggagaaa agaagaacgg  780
actgttcgga aacctgatcg cactgagcct gggactgaca ccgaacttca gagcaactt   840
cgacctggca gaagacgcaa agctgcagct gagcaaggac atacgacg acgacctgga   900
caacctgctg gcacagatcg gagaccagta cgcagacctg ttcctggcag caaagaacct  960
gagcgacgca atcctgctga gcgacatcct gagagtcaac acagaaatca aaaggcacc  1020
gctgagcgca agcatgatca agatatacga cgaacaccac caggacctga cactgctgaa  1080
ggcactggtc agacagcagc tgccggaaaa gtacaaggaa atcttcttcg accagagcaa  1140
gaacggatac gcaggataca tcgacgaggg agcaagccag gaagaattct acaagttcat  1200
caagccgatc ctggaaaaga tggacgaaac agaagaactg ctggtcaagc tgaacagaga  1260
agacctgctg agaaagcaga gaacattcga caacggaagc atcccgcacc agatccacct  1320
gggagaactg cacgcaatcc tgagaagaca ggaagacttc taccccgttcc tgaaggacaa  1380
cagagaaaag atcgaaaaga tcctgacatt cagaatcccg tactacgtcg gaccgctggc  1440
aagaggaaac agcagattcg catggatgac aagaaagagc gaagaaacaa tcacaccgtg  1500
gaacttcgaa gaagtcgtcg acaagggagc aagcgcacag agcttcatcg aaagaatgac  1560
aaacttcgac aagaacctgc cgaacgaaaa ggtcctgccg aagcacagcc tgctgtacga  1620
atacttcaca gtctacaacg aactgacaaa ggtcaagtac gtcacagaag gaatgagaaa  1680
gccggcattc ctgagcggag aacagaagaa ggcaatcgtc gacctgctgt tcaagacaaa  1740
cagaaaggtc acagtcaagc agctgaagga agactacttc aagaagatcg aatgcttcga  1800
cagcgtcgaa atcagcggag tcgaagacag attcaacgca agcctgggaa cataccacga  1860
cctgctgaag atcatcaagg acaaggactt cctggacaac gaagaaaacg aagacatcct  1920
ggaagacatc gtcctgacac tgacactgtt cgaagacaga gaaatgatcg aagaaagact  1980
gaagacatac gcacacctgt tcgacgacaa ggtcatgaag cagctgaaga agaagaagata  2040
cacaggatgg ggaagactga gcagaaagct gatcaacgga atcagagaca agcagagcgg  2100
aaagacaatc ctggacttcc tgaagagcga cggattcgca aacgaaaact tcatgcagct  2160
gatccacgac gacagcctga cattcaagga agacatccag aaggcacagg tcagcggaca  2220
gggagacagc ctgcacgaac acatcgcaaa cctggcagga agcccggcaa tcaagaaggg  2280
aatcctgcag acagtcaagg tcgtcgacga actggtcaag gtcatgggaa gacacaagcc  2340
ggaaaacatc gtcatcgaaa tggcaagaga aaaccagaca acacagaagg gacagaagaa  2400
cagcagagaa agaatgaaga gaatcgaaga aggaatcaag gaaatcctcc cgatcgaagc  2460
gaaggaacac ccgtcgaaaa cacacagct gcaacgaa aagctgtacc tgtactaccct  2520
gcagaacgga agagacatgt acgtcgacca ggaactggac atcaacgac tgagcgacta  2580
cgacgtcgac cacatcgtcc cgcagagctt cctgaaggac gacagcatcg acaacaaggt  2640
cctgacaaga agcgacaaga acagaggaaa gagcgacaac gtcccgagcg aagaagtcgt  2700
caagaagatg aagaactact ggagacagct gctgaacgca agctgatca cagagagaaa  2760
gttcgacaac ctgacaaagg cagagagagg aggactgagc gaactggaca aggcaggatt  2820
catcaagaga cagctggtcg aaacaagaca gatcacaaag cacgtcgcac agatcctgga  2880
cagcagaatg aacacaaagt acgacgaact gacaagctg atcagagaag tcaaggtcat  2940
cacactgaag agcaagctgg tcagcgactt cagaaaggac ttccagttct acaaggtcag  3000
agaaatcaac aactaccacc acgcacacga cgcatacctg aacgcagtcg tcggaacagc  3060
actgatcaag aagtacccga agctggaaag cgaattcgtc tacggagact acaaggtcta  3120
cgacgtcaga aagatgatcg caaagagcga acaggaaatc ggaaaggcaa cagcaaagta  3180
cttcttctac agcaacatca tgaacttctt caagacagaa atcacactgg caaacgagaa  3240
aatcagaaag agaccgctga tcgaaacaaa cggagaaaca ggagaaatcg tctgggacaa  3300
gggaagagac ttcgcaacag tcagaaaggt cctgagcatg ccgcaggtca catcgtcaa  3360
gaagacagaa gtccagacag gaggattcag caaggaaagc atcctgccga gagaaacag  3420
cgacaagctg atcgtcaagaa agaaggactg ggaccgaaga agtacggag gattcgcag  3480
cccgacagtc gcatacagcg tcctggtcgt cgcaaaggtc gaaaaggaa agagcaagaa  3540
gctgaagagc gtcaaggaac tgctgggaat cacaatcatg gaaagaagca gcttcgaaaa  3600
gaacccgatc gacttcctgg aagcaaaggg atacaaggaa gtcaagaagg acctgatcat  3660
caagctgccg aagtacagcc tgttcgaact gaaaaacgga agaaagagaa tgctggcaag  3720
cgcaggagaa ctgcagaagg gaaacgaact ggcactgccg agcaagtacg tcaacttcct  3780
gtacctggca agcactacg aaaagctgaa gggaagcccg gaagacacg aacagagca   3840
gctgttcgtc gaacagcaca gcactacctg gacgaaatc atcgaacaga tcagcgaatt  3900
cagcaagaga gtcatcctgg cagacgcaaa cctggacaag gtcctgagcg catacaacaa  3960
gcacagagac aagccgatca gagaacaggc agaaaacatc atcccacctgt tcacactgac  4020
aaacctggga gcaccggcag cattcaagta cttcgacaca caatcgaca gaaagagata  4080
cacaagcaca aaggaagtcc tggacgcaac actgatccac cagagcatca caggactgta  4140
cgaaacaaga atcgacctga ccagctgggg aggagacgga ggaggaagcc gaagaagaa  4200
gagaaaggtc tagctagcca tcacatttaa aagcatctca gcctaccatg agaataagag  4260
aaagaaaatg aagatcaata gcttattcat tctcttttct tttcgttgg tgtaaagcca  4320
acaccctgta taaaaacat aaatttcttt aatcattttg cctctttttct ctgtgcttca  4380
attaataaaa aatggaaaga accaaaaaaa aaaaaaaaaa aaaaaaaaaa aaaaaaaaaa  4440
aaaaaaaaaa aaaaaaaaaa aaaaaaaaaa aaaaaaaaaa aaaaaaaaaa aaaaaaaaaa  4500
```

SEQ ID NO: 31    moltype = DNA    length = 4500

| FEATURE | Location/Qualifiers |
|---|---|
| misc_feature | 1..4500 |
| | note = Cas9 mRNA with a poly-A tail comprising SEQ ID NO: 2 |
| source | 1..4500 |
| | mol_type = other DNA |
| | organism = synthetic construct |

SEQUENCE: 31

```
tcccgcagtc ggcgtccagc ggctctgctt gttcgtgtgt gtgtcgttgc aggccttatt    60
cggatccgcc accatggaca agaagtacag catcggactg gacatcggaa caaacagcgt   120
cggatgggca gtcatcacag acgaatacaa ggtcccgagc aagaagttca aggtcctggg   180
aaacacagac agacacagca tcaagaagaa cctgatcgga gcactgctgt tcgcagcgg   240
agaaacagca gaagcaacaa gactgaagag aacagcaaga agaagataca caagaagaaa   300
gaacagaatc tgctacctgc aggaaatctt cagcaacgaa atggcaaagg tcgacgacag   360
cttcttccac agactggaag aaagcttcct ggtcgaagaa gacaagagc acgaaagaca   420
cccgatcttc ggaaacatcg tcgacgaagt cgcataccac gaaaagtacc cgacaatcta   480
ccacctgaga aagaagctgg tcgacagcac agacaaggca gacctgagac tgatctacct   540
ggcactggca cacatgatca agttcagagg acacttcctg atcgaaggag acctgaaccc   600
ggacaacagc gacgtcgaca agctgttcat ccagctggtc cagacataca accagctgtt   660
cgaagaaaac ccgatcaacg caagcggagt cgacgcaaag gcaatcctga gcgcaagact   720
gagcaagagc agaagactgg aaaacctgat cgcacagctg ccgggagaaa agaagaacgg   780
actgttcgga aacctgatcg cactgagcct gggactgaca ccgaacttca gagcaactt   840
cgacctggca gaagacgcaa agctgcagct gagcaaggac acatacgacg acgacctgga   900
caacctgctg gcacagatcg gagaccagta cgcagacctg ttcctggcag caaagaacct   960
gagcgacgca atcctgctga gcgacatcct gagagtcaac acagaaatca caaaggcacc  1020
gctgagcgca agcatgatca agagatacga cgaacaccac caggacctga cactgctgaa  1080
ggcactggtc agacagcagc tgccggaaaa gtacaaggaa atcttcttcg accagagcaa  1140
gaacggatac gcaggataca tcgacggagg agcaagccag gaagaattct acaagttcat  1200
caagccgatc ctggaaaaga tggacggaac agaagaactg ctggtcaagc tgaacagaga  1260
agacctgctg agaaagcaga gaacattcga caacggaagc atcccgcacc agatccacct  1320
gggagaactg cacgcaatcc tgagaagaca ggaagacttc taccgttcc tgaaggacaa  1380
cagagaaaag atcgaaaaga tcctgacatt cagaatcccg tactacgtcg gaccgctggc  1440
aagaggaaac agcagattcg catggatgac aagaaagagc gaagaaacaa tcacaccgtg  1500
gaacttcgaa gaagtcgtcg acaagggagc aagcgcacag agcttcatcg aaagaatgac  1560
aaacttcgac aagaacctgc cgaacgaaaa ggtcctgccg aagcagctgg aagacatcct  1620
atacttcaca gtctacaacg aactgacaaa ggtcaagtac gtcacagaag gaatgagaaa  1680
gccggcattc ctgagcggag aacagaagaa ggcaatcgtc gacctgctgt tcaagacaaa  1740
cagaaaggtc acagtcaagc agctgaagga agactactc aagaagatcg aatgcttcga  1800
cagcgtcgaa atcagcggag tcgaagacag attcaacgca agcctgggaa cataccacga  1860
cctgctgaag atcatcaagg acaaggactt cctggacaac gaagaaaacg aagacatcct  1920
ggaagacatc gtcctgacac tgacactgtt cgaagacaga gaaatgatcg aagaaagact  1980
gaagacatac gcacacctgt tcgacgacaa ggtcatgaag cagctgaaga agaagaata  2040
cacaggatgg ggaagactga gcagaaagct gatcaacgga atcagagaca gcagagcgg  2100
aaagacaatc ctggacttcc tgaagagcga cggattcgca aacagaaact tcatgcagct  2160
gatccacgac gacagcctga cattcaagga agacatccag aaggcacagg tcagcggaca  2220
gggagacagc ctgcacgaac acatcgcaaa cctggcagga agcccggcaa tcaagaaggg  2280
aatcctgcag acagtcaagg tcgtcgacga actggtcaag gtcatgggaa gacacaagcc  2340
ggaaaacatc gtcatcgaaa tggcaagaga aaaccagaca acagaaggg acagaagaa  2400
cagcagagaa agaatgaaga aatcgaaga aggaatcaag gaactgggaa gccagatcct  2460
gaaggaaacc ccggtcgaaa acacacagct gcagaacgaa aagctgtacc tgtactacct  2520
gcagaacgga agagacatgt acgtcgacca ggaactggac atcaacagac tgagcgacta  2580
cgacgtcgac cacatcgtcc cgcagagctt cctgaaggac gacagcatcg acaacaagtg  2640
cctgacaaga agcgacaaga cagaggaaa gagcgacaac gtcccgagcg aagaagtcgt  2700
caagaagatg aagaactact ggagacagct gctgaacgca agctgatca cacagagaaa  2760
gttcgacaac ctgacaaagg cagagagagg aggactgagc gaactggaca aggcaggatt  2820
catcaagaga cagctggtcg aaacaagaca gatcacaaag cacgtcgcac agatcctgga  2880
cagcagaatg aacacaaagt acgacgaaaa cgacaagctg atcagagaag tcaaggtcat  2940
cacactgaag agcaagctgg tcagcgactt cagaaaggac ttccagttct acaaggtcag  3000
agaaatcaac aactaccacc acgcacacga cgcataccta aacgcagtcg tcggaacagc  3060
actgatcaag aagtacccga agctgaaag cgaattcgtc tacggagact acaaggtcta  3120
cgacgtcaga aagatgatcg caaagagcga acaggaaatc ggaaaggcaa cagcaaagta  3180
cttcttctac agcaacatca tgaacttctt caagacagaa atcacactgg caaacgaga   3240
aatcagaaag agaccgctga tcgaaacaaa cggagagaaca ggagaaatcg tctgggaca   3300
gggaagagac ttcgcaacag tcagaaaggt cctgagcatg ccgcaggtca acatcgtcaa  3360
gaagacagaa gtccagacag gaggattcag caaggaaagc atcctgccga agagaaacag  3420
cgacaagctg atcgcaagaa agaaggactg gaccccgaag aagtacgag attcgcag    3480
cccgacagtc gcatacagcg tcctggtcgt cgcaaaggtc gaaaaggaa agagcaagaa  3540
gctgaagagc gtcaaggaac tgctgggaat cacaatcatg gaaagaagca gcttcgaaaa  3600
gaacccgatc gacttcctgg aagcaaaggg atacaaggaa gtcaagaagg acctgatcat  3660
caagctgccg aagtacagcc tgttcgaact ggaaaacgga agaaagagaa tgctggcaag  3720
cgcaggagaa ctgcagaagg gaaacgaact ggcactgccg agcaagtacg tcaacttcct  3780
gtacctggca agcactacg aaaagctgaa gggaagcccg gaagacaacg aacagaagca  3840
gctgttcgtc gaacagcaca gcactacct ggacgaaatc atcgaacaga tcagcgaatt  3900
cagcaagaga gtcatcctgg cagacgcaaa cctggacaag gtcctgagcg catacaacaa  3960
gcacagagac aagccgatca gagaacaggc agaaaacatc atccacctgt tcacactgac  4020
aaacctggga gcaccggcag cattcaagta cttcgacaca acaatcgaca gaaagagata  4080
cacaagcaca aaggaagtcc tggacgcaac actgatccac cagagcatca caggactgta  4140
cgaaacaaga atcgacctga cccagctggg aggagacgga ggaggaagcc cgaagaagaa  4200
gagaaaggtc tagctagcca tcacatttaa aagcatctca gcctaccatg agaataagag  4260
aaagaaaatg aagatcaata gcttattcat ctctttttct tttcgttgg tgtaaagcca  4320
```

```
acaccctgtc taaaaaacat aaatttcttt aatcattttg cctcttttct ctgtgcttca    4380
attaataaaa aatggaaaga accaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
```

STABILIZED NUCLEIC ACIDS ENCODING MESSENGER RIBONUCLEIC ACID (MRNA)

This application is a Continuation of U.S. application Ser. No. 16/791,076, which was filed on Feb. 14, 2020, which is a Continuation of International Application No. PCT/US2018/046772, which was filed Aug. 14, 2018 and which claims the benefit of priority to U.S. Provisional Application No. 62/545,883, which was filed on Aug. 15, 2017, all of which are incorporated by reference in their entirety.

The patent application is filed with a sequence listing in electronic format. The Sequence Listing is provided as a file entitled "2023-04-27_01155-0019-01US_ST26," which was created on Apr. 27, 2023, and which is 95,864 bytes in size. The information in the electronic format of the sequence listing is incorporated herein by reference in its entirety.

This disclosure relates to the field of stabilized messenger ribonucleic acid (mRNA) and DNA encoding the stabilized mRNA.

BACKGROUND

Polyadenylation is the process of adding multiple adenine nucleotides to the 3' end of a messenger RNA (mRNA), forming a poly-A tail. The poly-A tail consists of multiple repeated adenine nucleotides, such as adenosine monophosphates, without other bases interrupting the sequence. The poly-A tail is critical for the nuclear export, translation, and stability of mRNA. In nature, as mRNA is produced from DNA, a terminal transferase adds adenine nucleotides to the 3' end of mRNA. This enzymatic process can be applied when producing mRNA ex vivo, but the process is difficult to control and results in poly-A tails of different lengths. By encoding a poly-A tail in the plasmid, it is possible to decrease the heterogeneity in the poly-A tail. However, it does not eliminate the heterogeneity, and has additional downsides such as potential instability of the plasmid.

The poly-A tail acts as the binding site for poly-A-binding protein. Poly-A-binding protein assists in exporting mRNA from the nucleus, translation, and inhibiting degradation of the mRNA. In the absence of export from the nucleus, mRNAs are typically degraded by the exosome. The poly-A-binding protein recruits proteins necessary for translation.

mRNA is now being used as a therapeutic molecule, for example, for the treatment of various diseases and disorders. mRNA is delivered to a subject in lieu of the protein so that the subject's cells produce the protein encoded by the mRNA within the cell. For these and other purposes, mRNA may be prepared via transcription from a DNA template, often contained in a plasmid. During mRNA production, the poly-A tail may be added to mRNA enzymatically after transcription from a plasmid or encoded on the plasmid itself. When the poly-A tail is encoded on a plasmid, the poly-A tail may become shorter (i.e., lose adenine nucleotides) over cycles of plasmid DNA replication, potentially leading to large variations in the resulting DNA and subsequent mRNA population. Thus, there exists a need in the art to design plasmids encoding poly-A tails that are stable and resistant to gradual loss of nucleotides encoding poly-A adenine nucleotides during DNA replication.

SUMMARY

Disclosed herein are DNA encoding, and mRNA comprising, poly-adenylated (poly-A) tails comprising consecutive adenine nucleotides located 3' to nucleotides encoding a protein of interest, wherein the poly-A tail is stabilized by inserting non-adenine nucleotide "anchors."

As used herein, the term "poly-A tail" refers to a poly-A tail on an mRNA molecule, or a sequence encoding a poly-A tail within a DNA plasmid. A poly-A tail may be encoded by a complementary DNA sequence within a plasmid. A sequence of repeating thymine (T) nucleotides in a DNA sequence, e.g. a homopolymer T sequence, may encode a poly-A tail on an mRNA. Two or more consecutive adenosine (e.g. adenosine or deoxyadenosine), thymidine, or other nucleotides are called homopolymers. Naturally-occurring poly-A tails comprise long, uninterrupted homopolymer A sequences.

The non-adenine nucleotide anchors disclosed herein interrupt the poly-A tail at regular or irregularly spaced intervals and stabilize the DNA encoding the poly-A tail as well as the mRNA produced from the DNA. Exemplary non-adenine nucleotide anchors are provided in Table 4. An anchor sequence, for example, is adjacent to two adenine nucleotide homopolymer sequences within the poly-A tail.

In some embodiments, a DNA composition comprising nucleotides encoding a poly-adenylated (poly-A) tail located 3' to nucleotides encoding a protein of interest, wherein the poly-A tail comprises at least 8 consecutive adenine (A) nucleotides and one or more non-adenine (A) nucleotides is encompassed.

In some embodiments, the poly-A tail comprises at least 10, 15, 20, 25, 30, 35, 40, 45, 50, 55, 60, 65, 70, 75, 80, 85, or 90 consecutive adenine nucleotides.

In some instances, the one or more non-adenine nucleotides prevent the loss of one or more adenine nucleotides during DNA replication as compared to the loss that occurs in a DNA comprising a 3' tail of a similar or same length that contains only adenine nucleotides.

In some embodiments, the one or more non-adenine nucleotides are positioned to interrupt the consecutive adenine nucleotides so that a poly(A) binding protein can bind to a stretch of consecutive adenine nucleotides.

In some embodiments, the poly-A tail comprises at least 50 total adenine nucleotides.

In some embodiments, the poly-A tail comprises 40-500 total adenine nucleotides.

In some instances, the poly-A tail comprises 95-100 total adenine nucleotides.

In some embodiments, the poly-A tail comprises or contains 90, 91, 92, 93, 94, 95, 96, or 97 total adenine nucleotides.

In some embodiments, the poly-A tail comprises or contains 96 or 97 total adenine nucleotides.

In some embodiments, the poly-A tail comprises or contains one non-adenine nucleotide or one consecutive stretch of 2-10 non-adenine nucleotides.

In some embodiments, the non-adenine nucleotide(s) is located after at least 8, 9, 10, 11, or 12 consecutive adenine nucleotides.

In some instances, the one or more non-adenine nucleotides are located after at least 8-50 consecutive adenine nucleotides.

In some embodiments, the one or more non-adenine nucleotides are located after at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, the poly-A tail comprises or contains one non-adenine nucleotide or one consecutive stretch of 2-10 nucleotides every 8-50 consecutive adenine nucleotides. In some embodiments, the poly-A tail comprises or contains one non-adenine nucleotide or one consecutive stretch of 2-10 nucleotides comprising at least two non-adenine nucleotides every 8-50 consecutive adenine nucleotides. In some embodiments, the poly-A tail has one or more non-adenine nucleotides or one or more consecutive stretches of 2-10 non-adenine nucleotides irregularly spaced anywhere along the length of the poly-A tail, wherein somewhere along the length of the poly-A tail there are at least 8 consecutive adenines. For example, a poly-A tail may be 70-1000 nucleotides in length, and have any number of non-adenines (either singly or grouped) irregularly spaced along the length, as long as there is one or more stretch of at least 8 consecutive adenines.

In some instances, the poly-A tail comprises or contains one non-adenine nucleotide or one consecutive stretch of 2-10 nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some instances, the poly-A tail comprises or contains one non-adenine nucleotide or one consecutive stretch of 2-10 nucleotides comprising at least two non-adenine nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, the poly-A tail comprises or contains 1, 2, 3, 4, or 5 consecutive non-adenine nucleotides every 8-50 consecutive adenine nucleotides.

In some instances, the poly-A tail comprises or contains 1, 2, 3, 4, or 5 consecutive non-adenine nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, the poly-A tail comprises or contains more than one non-adenine nucleotide or more than one consecutive stretch of 2-10 nucleotides as interrupting sequences irregularly spaced within the poly-A tail.

In some embodiments, the poly-A tail comprises or contains more than one non-adenine nucleotide or more than one consecutive stretch of 2-10 nucleotides comprising at least two non-adenine nucleotides irregularly spaced within the poly-A tail.

In some instances, the poly-A tail comprises or contains one non-adenine nucleotide or 2, 3, 4, or 5 consecutive non-adenine nucleotides every 12 consecutive adenine nucleotides.

In some embodiments, the poly-A tail comprises or contains one non-adenine nucleotide or 2, 3, 4, or 5 consecutive non-adenine nucleotides every 16 consecutive adenine nucleotides.

In some embodiments, the poly-A tail comprises or contains one non-adenine nucleotide or 2, 3, 4, or 5 consecutive non-adenine nucleotides every 25 consecutive adenine nucleotides.

In some instances, the poly-A tail comprises or contains one non-adenine nucleotide or 2, 3, 4, or 5 consecutive non-adenine nucleotides every 30 consecutive adenine nucleotides.

In some embodiments, the poly-A tail comprises or contains one non-adenine nucleotide or 2, 3, 4, or 5 consecutive non-adenine nucleotides every 39 consecutive adenine nucleotides.

In some embodiments, the non-adenine nucleotide is guanine, cytosine, or thymine. In some instances, the non-adenine nucleotide is a guanine nucleotide. In some embodiments, the non-adenine nucleotide is a cytosine nucleotide. In some embodiments, the non-adenine nucleotide is a thymine nucleotide.

In some instances, where more than one non-adenine nucleotide is present, the non-adenine nucleotide may be selected from: a) guanine and thymine nucleotides; b) guanine and cytosine nucleotides; c) thymine and cytosine nucleotides; or d) guanine, thymine and cytosine nucleotides.

In some embodiments, the non-adenine nucleotide consists of one non-adenine nucleotide selected from guanine, cytosine, and thymine.

In some instances, the non-adenine nucleotides comprise two non-adenine nucleotides selected from one or more of guanine, cytosine, and thymine.

In some embodiments, the non-adenine nucleotides comprise three non-adenine nucleotides selected from one or more of guanine, cytosine, and thymine.

The adenine nucleotides may be adenosine monophosphate.

In some embodiments, the protein encoded by the mRNA is a therapeutic protein. In some instances, the protein a cytokine, chemokine, growth factor, Cas9 or modified Cas9.

In some embodiments, mRNA encoded by any of the DNAs described herein is encompassed.

In some embodiments, the DNA is within a vector. The vector may be within a host cell, including insect, bacterial, or mammalian (e.g., human) cells.

In some embodiments, the one or more non-adenine nucleotide prevents loss of nucleotides encoding the poly-A tail within the vector during growth of the host cell as compared to the loss that occurs in a DNA comprising nucleotides encoding a poly-A tail of a similar or same length that contains only adenine nucleotides.

Methods of producing mRNA from any of the DNA vectors described herein are encompassed comprising: linearizing the vector downstream of the poly-A tail; denaturing the linearized vector; and contacting the denatured DNA with an RNA polymerase in the presence of guanine, cytosine, uracil, and adenine nucleotides.

In some embodiments, this disclosure includes a DNA comprising nucleotides encoding a poly-adenylated (poly-A) tail located 3' to nucleotides encoding a protein of interest, wherein the poly-A tail comprises a first homopolymer sequence of at least 8 consecutive adenine (A) nucleotides and an interrupting sequence comprising one or more non-adenine (A) nucleotides. In some such embodiments, the poly-A tail further comprises a second homopolymer sequence of at least consecutive adenine (A) nucleotides. In some embodiments, the poly-A tail comprises three or more homopolymer sequences of at least 8 consecutive adenine (A) nucleotides. In some embodiments, the first and/or subsequent homopolymer sequence comprises at least 10, 15, 20, 25, 30, 35, or 40 consecutive adenine nucleotides. In some embodiments, the one or more non-adenine nucleotide prevents the loss of one or more adenine nucleotide during DNA replication as compared to the loss that occurs in a DNA comprising a 3' tail of a similar or same length that contains only adenine nucleotides. In some embodiments, the one or more non-adenine nucleotide is positioned to interrupt the consecutive adenine nucleotides so that a poly(A) binding protein can bind to a stretch of consecutive adenine nucleotides. In some embodiments, the poly-A tail comprises at least 50 total adenine nucleotides. In some embodiments, the poly-A tail comprises 40-1000, 40-900, 40-800, 40-700, 40-600, 40-500, 40-400, 40-300, 40-200, or 40-100 total adenine nucleotides. In some embodiments, the poly-A tail comprises 95-100 total adenine nucleotides. In some embodiments, the poly-A tail comprises or contains 90, 91, 92, 93, 94, 95, 96, or 97 total adenine nucleotides. In some embodiments, the poly-A tail comprises or contains 96 or 97 total adenine nucleotides. In some embodiments, the one or more interrupting sequence comprises or contains one non-adenine nucleotide or one consecutive stretch of 2-10 non-adenine nucleotides. In some embodiments, the one or more interrupting sequence comprises or contains one non-adenine nucleotide or one consecutive stretch of 2-10 nucleotides that includes two or more non-adenine nucleotides. In some embodiments, the non-adenine nucleotide(s) is located after at least 8, 9, 10, 11, or 12 consecutive adenine nucleotides. In some embodiments, the one or more non-adenine nucleotide is located after at least 8-50 consecutive adenine nucleotides. In some embodiments, the one or more non-adenine nucleotide is located after at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, as described in the preceding paragraph, the interrupting sequence is a trinucleotide, dinucleotide or mononucleotide interrupting sequence. In some such embodiments, the poly-A tail comprises or contains one non-adenine nucleotide or one consecutive stretch of 2-10 non-adenine nucleotides every 8-50 consecutive adenine nucleotides. In some embodiments, the poly-A tail comprises or contains one non-adenine nucleotide or one consecutive stretch of 2-10 non-adenine nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides. In some embodiments, the poly-A tail comprises or contains 1, 2, 3, 4, or 5 consecutive non-adenine nucleotides every 8-50 consecutive adenine nucleotides. In some embodiments, the poly-A tail comprises or contains 1, 2, 3, 4, or 5 consecutive non-adenine nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides. In some embodiments, the poly-A tail comprises or contains more than one non-adenine nucleotide or more than one consecutive stretch of 2-10 non-adenine nucleotides. In some embodiments, the more than one non-adenine nucleotide or more than one consecutive stretch of 2-10 non-adenine nucleotides are irregularly spaced within the poly-A tail. In some embodiments, the poly-A tail comprises or contains one non-adenine nucleotide or 2, 3, 4, or 5 consecutive non-adenine nucleotides every 12 consecutive adenine nucleotides. In some embodiments, the poly-A tail comprises or contains one non-adenine nucleotide or 2, 3, 4, or 5 consecutive non-adenine nucleotides every 16 consecutive adenine nucleotides. In some embodiments, the poly-A tail comprises or contains one non-adenine nucleotide or 2, 3, 4, or 5 consecutive non-adenine nucleotides every 25 consecutive adenine nucleotides. In some embodiments, the poly-A tail comprises or contains one non-adenine nucleotide or 2, 3, 4, or 5 consecutive non-adenine nucleotides every 30 consecutive adenine nucleotides. In some embodiments, the poly-A tail comprises or contains one non-adenine nucleotide or 2, 3, 4, or 5 consecutive non-adenine nucleotides every 39 consecutive adenine nucleotides. In some embodiments, the non-adenine nucleotide is guanine, cytosine, or thymine. In some embodiments, the non-adenine nucleotide is a guanine nucleotide. In some embodiments, the non-adenine nucleotide is a cytosine nucleotide. In some embodiments, the non-adenine nucleotide is a thymine nucleotide. In some embodiments, the DNA comprises more than one non-adenine nucleotide selected from: (a) guanine and thymine nucleotides; (b) guanine and cytosine nucleotides; (c) thymine and cytosine nucleotides; or (d) guanine, thymine and cytosine nucleotides. In some embodiments described above, the non-adenine nucleotide consists of one non-adenine nucleotide selected from guanine, cytosine, and thymine. In some embodiments, non-adenine nucleotides comprise two non-adenine nucleotides selected from one or more of guanine, cytosine, and thymine. In some embodiments, non-adenine nucleotides comprise three non-adenine nucleotides selected from one or more of guanine, cytosine, and thymine. In some embodiments, adenine nucleotides are adenosine monophosphate. In some embodiments, the protein is a therapeutic protein. In some embodiments, the protein a cytokine or chemokine. In some embodiments, the protein a growth factor. In some embodiments, the protein is Cas9 or modified Cas9.

This disclosure also encompasses an mRNA encoded by the DNA as described in the preceding paragraphs.

In some embodiments, the DNA described in the preceding paragraphs may also be comprised within a vector. In some embodiments, the vector is comprised within a host cell. In some embodiments, where the DNA is within a vector, the one or more non-adenine nucleotide prevents loss of nucleotides encoding the poly-A tail within the vector during growth of the host cell as compared to the loss that occurs in a DNA comprising nucleotides encoding a poly-A tail of a similar or same length that contains only adenine nucleotides.

This disclosure also encompasses methods of producing mRNA from the DNA vectors described herein, comprising: (a) linearizing the vector downstream of the poly-A tail; (b) denaturing the linearized vector; and (c) contacting the denaturized DNA with an RNA polymerase in the presence of guanine, cytosine, uracil, and adenine nucleotides.

FIGURE LEGENDS

DETAILED DESCRIPTION

Figure 1:
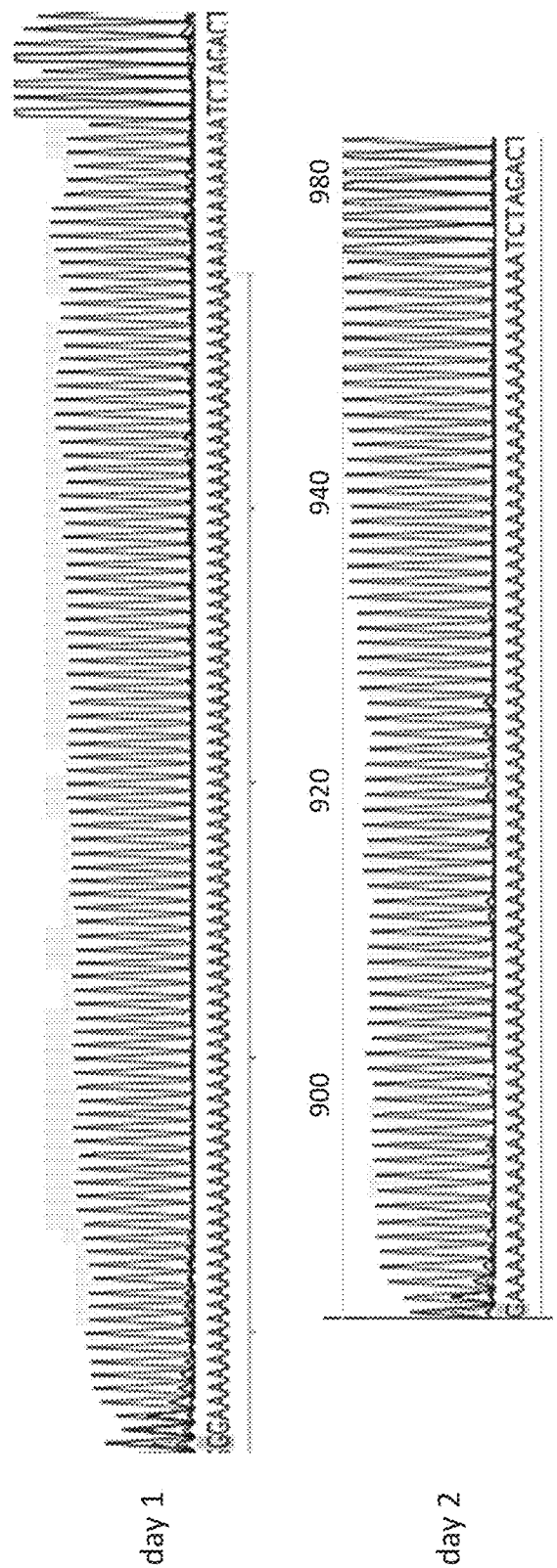
FIG. 1 shows a sequence encoding a poly-A tail that contains only adenosines decreasing in length over rounds of growth. Each clone refers to a DNA generated by successive rounds of growth/purification of host cells expressing plasmid encoding the clones.

Disclosed herein are DNAs encoding a poly-adenylated tail located 3' to nucleotides encoding a protein of interest, wherein the poly-A tail comprises one or more non-adenine nucleotides. During DNA replication, DNA encoding a poly-A tail comprising one or more non-adenine nucleotide may show less gradual loss of adenine nucleotides within the poly-A tail compared with poly-A tails consisting only of adenine nucleotides. Thus, plasmids comprising DNA encoding a poly-A tail comprising one or more non-adenine nucleotide are provided. mRNA encoded by such DNA is also encompassed. Both the DNA and RNA may exhibit greater stability against processive loss of adenine nucleotides than similar molecules comprising non-interrupted poly-A tails.

The protein of interest may be any natural or non-natural protein. As used herein, "protein" refers to any sequence of consecutive amino acids. As such, a protein may refer to a protein that comprises the full amino acid sequence of a naturally occurring protein. In addition, a protein may refer to an amino acid sequence that comprises a fragment of a full-length protein. A protein may be a naturally-occurring sequence, a naturally-occurring sequence with one or more modifications, or an artificial sequence that does not occur in nature.

The protein of interest may be of therapeutic use in a subject, or this protein may be of use in a biochemical reaction. Therapeutic proteins include, for example, growth factors, antigens for vaccines or immuno-oncology, and enzymes, among others. Therapeutic proteins may be naturally occurring or modified. In certain circumstances, a modified protein may be a fusion protein.

In some embodiments, expression of a protein by an mRNA is for use as a treatment for a disease. In some embodiments, expression of a protein by an mRNA is for use as a cancer immunotherapy, vaccination against infectious disease, to induce tolerance to a type I allergy, as a replacement therapy, or as a regenerative medicine (see Sergeeva O V et al, *Biochemistry* (Moscow) 81(7):709-722 (2016)).

In some embodiments, autologous dendritic cells are transfected ex vivo with an mRNA encoding for prostate-specific antigen (PSA) to modulate the T-cell immune response in subjects with metastatic prostate cancer.

In some embodiments, an mRNA is a prophylactic vaccine. In some embodiments, an mRNA encodes for one or more antigenic proteins. In some embodiments, the antigenic protein(s) is a viral protein. In some embodiments, the mRNA causes cells of the body to produce and express an antigenic protein. In some embodiments, the mRNA causes expression of antigenic proteins without a danger or disease or spread between individuals. In some embodiments, expression of antigenic proteins causes the immune system of a subject to produce antibodies. In some embodiments, these antibodies can neutralize a virus and prevent future infection after exposure to the virus. In some embodiments, the mRNA is a prophylactic vaccine for an infectious disease. In some embodiments, the mRNA is prophylactic vaccine against influenza, chikungunya, Zika, cytomegalovirus, human metapneumovirus (HMPV), or parainfluenza virus type 3 (PIV3). In some embodiments, the mRNA is a prophylactic vaccine against influenza H10 or H7 subtypes.

In some embodiments, an mRNA is a personalized cancer vaccine. In some embodiments, an mRNA primes the immune system of a subject with cancer to recognize cancer cells and mount a response. In some embodiments, this response is tailored to the individual patient's cancer or tumor. In some embodiments, an mRNA encodes a patient's specific neoantigens (unique proteins with mutations present in the patient's cancer or tumor). In some embodiments, an mRNA causes expression of a patient's specific neoantigens. In some embodiments, expression of neoantigens elicits a specific immune response in the patient to recognize and destroy cancer cells. In some embodiments, an mRNA is of use as a personalized cancer vaccine. In some embodiments, an mRNA is of use as a personalized cancer vaccine together with one or more checkpoint inhibitor antibodies, such as anti-PD-1 therapies.

In some embodiments, an mRNA is of use for intratumoral immuno-oncology. In some embodiments, injection of an mRNA into a tumor reduces off-target effects and/or may be more potent compared to systemic administration. In some embodiments, the mRNA causes expression of OX40L (CD252), the ligand for CD134. In some embodiments, the mRNA causes expression of cytokines such as interleukin 12 (IL-12).

In some embodiments, an mRNA causes expression of a protein for localized therapy. In some embodiments, an mRNA causes creation of more blood vessels and improved blood supply in a local tissue. In some embodiments, the mRNA causes expression of vascular endothelial growth factor A (VEGF-A). In some embodiments, expression of VEGF-A is local and transient. In some embodiments, local and transient expression of VEGF-A is of use for treatment of heart failure or after a heart attack, of diabetic wound healing, or of other ischemic vascular diseases.

In some embodiments, an mRNA causes expression of a protein for replacement therapy. In some embodiments, the protein is surfactant protein-B.

In some embodiments, an mRNA causes expression of an RNA-guided nuclease such as class 2 CRISPR-associated Cas endonuclease, e.g. Cas9/Csn1 (Cas9). An exemplary Cas9 sequence is UniProt Q99ZW2. In some embodiments, the protein is a modified Cas9 or a Cas9 protein fused to another functional protein or peptide. Modified versions of Cas9 having one catalytic domain, either RuvC or HNH, that is inactive are termed "nickases". In some embodiments, the compositions and methods comprise nickases. In some embodiments, the compositions and methods comprise a nickase Cas9 that induces a nick rather than a double strand break in the target DNA.

In some embodiments, the Cas protein may be modified to contain only one functional nuclease domain. For example, the Cas protein may be modified such that one of the nuclease domains is mutated or fully or partially deleted to reduce its nucleic acid cleavage activity. In some embodiments, a nickase Cas is used having a RuvC domain with reduced activity. In some embodiments, a nickase Cas is used having an inactive RuvC domain. In some embodiments, a nickase Cas is used having an HNH domain with reduced activity. In some embodiments, a nickase Cas is used having an inactive HNH domain.

In some embodiments, chimeric Cas proteins are encoded by the DNA, where one domain or region of the protein is replaced by a portion of a different protein. In some embodiments, a Cas nuclease domain may be replaced with a domain from a different nuclease such as Fok1. In some embodiments, a Cas protein may be a modified nuclease.

I. DNA Encoding Poly-A Tails Comprising Non-Adenine Nucleotides

As used herein, a "poly-A tail" refers to a sequence comprising adenosines or other adenine nucleotides at the 3' end of an mRNA. While natural poly-A tails may be comprised solely of adenine nucleotides, a "poly-A tail" of the present invention is stabilized by one or more non-adenine nucleotide "anchors". In some embodiments, the poly-A tail comprises at least 8 consecutive adenine nucleotides and one or more interrupting sequence comprising a non-adenine nucleotide. In other words, the poly-A tails of the present invention comprise at least 8 consecutive adenines, but also comprise one or more non-adenine nucleotide within the interrupting or anchor sequences. The interrupting sequences disclosed herein interrupt the poly-A tail at regular or irregularly spaced intervals and stabilize the DNA encoding the poly-A tail as well as the mRNA produced from the DNA. Exemplary interrupting sequences are provided in Table 4.

As used herein, "non-adenine nucleotides" refer to any natural or non-natural nucleotides that do not comprise adenine. Guanine, thymine, and cytosine nucleotides are exemplary non-adenine nucleotides.

Native poly-A tails are added in a process of polyadenylation that begins after transcription of a DNA into mRNA. In molecular biology methods, however, poly-A tails are often encoded by a section of DNA within a plasmid that encodes a protein of interest. In this instance, the size of the poly-A tail (i.e., the number of adenine nucleotides comprised in the poly-A tail) is directly dependent on the number of DNA nucleotides in the plasmid that encode for these consecutive adenine nucleotides.

The number of DNA nucleotides encoding the poly-A tail may gradually decrease during DNA replication during, for example, growth of the plasmid in a host cell. When the number of consecutive adenine-encoding nucleotides in a plasmid reduces, the yield of plasmid encoding full-length poly-A tail is reduced, and the resulting mRNA having shorter poly-A tails may have decreased stability and/or increased degradation. For example, an mRNA with a poly-A tail of 40 consecutive adenine nucleotides might be expected to have lower stability than an mRNA with a poly-A tail of 90 or more nucleotides. By lower stability, it is meant that an mRNA may be degraded more quickly, and consequently expression of a target protein is decreased from an mRNA with a shorter poly-A tail. As such, maintaining the length of a poly-A tail within a DNA plasmid over multiple rounds of DNA replication within host cells is beneficial. In addition, the poly-A tail may be important for translation, and maintaining a longer poly-A tail may result in improved protein expression from the mRNA.

Inclusion of one or more non-adenine nucleotides in a poly-A tail located 3' to nucleotides encoding a protein of interest may prevent the loss of one or more adenine nucleotides during DNA replication as compared to the loss that occurs in a DNA comprising a 3' poly-A tail of a similar or same length that contains only adenine nucleotides. The presence of a longer poly-A tail may also improve the efficiency of protein translation from an mRNA.

A. Adenine Nucleotides

The number of consecutive adenine nucleotides in a poly-A tail of this invention is designed to allow the poly-A-binding protein to bind to the consecutive adenosines. As used herein, "poly-A binding protein," "poly A binding protein," or "polyadenylate-binding protein" refers to a protein that binds to a poly-A tail of an mRNA. A poly-A binding protein may function to regulate translational initiation. By binding to poly-A tails, a poly-A binding protein may protect them from uridylation by ZCCHC6/ZCCHC11 and hence contribute to mRNA stability. A poly-A binding protein may be localized in cytoplasmic messenger ribonucleoprotein (mRNP) granules containing untranslated mRNAs that shuttle between the cytoplasm and the nucleus. An exemplary poly-A binding protein is PABPC1 (Uniprot Reference Number: P11940). DNA of the present invention may encode sufficient consecutive adenine nucleotides such that when transcribed into mRNA, one or more poly-A binding proteins retains ability to bind the poly-A tail. An interrupting non-adenine nucleotide anchor is placed after this functional number of consecutive adenine nucleotides.

In some embodiments, the one or more non-adenine nucleotide is positioned to interrupt the consecutive adenine nucleotides so that a poly-A binding protein can bind to a stretch of consecutive adenine nucleotides (i.e. an adenine nucleotide homopolymer or "homopolymer A". In some embodiments, the poly-A tail comprises at least 8 consecutive adenine nucleotides. In some embodiments, the at least 8 consecutive adenine nucleotides are 8, 9, 10, 11, and/or 12 consecutive nucleotides. In some embodiments, the poly-A tail comprises at least 10, 15, 20, 25, 30, 35, and/or 40 consecutive adenine nucleotides. In some embodiments, the poly-A tail comprises at least 10, 15, 20, 25, 30, 35, 40, 45, 50, 55, 60, 65, 70, 75, 80, 85, and/or 90 consecutive adenine nucleotides. A homopolymer, for example in a poly-A RNA sequence, may comprise at least 8, 9, 10, 11, 12, 13, 14, 15, 16, 17, 18, 19, 20, 21, 22, 23, 24, 25, 30, 35, or 40 consecutive adenosine nucleotides. A homopolymer, for example in a plasmid sequence encoding the poly-A tail, may comprise at least 8, 9, 10, 11, 12, 13, 14, 15, 16, 17, 18, 19, 20, 21, 22, 23, 24, 25, 30, 35, or 40 consecutive thymidine nucleotides. In some embodiments, the poly-A tail comprises two or more homopolymer A sequences of different lengths, e.g. the interrupting sequences in the poly-A tail are irregularly spaced. In some embodiments, the poly-A tail comprises regularly spaced interrupting sequences and two or more homopolymers of the same length.

In some embodiments, the poly-A tail comprises a first homopolymer sequence of at least 8 consecutive adenine nucleotides, a second homopolymer sequence of at least 5 consecutive adenine nucleotides, and an anchor comprising one or more non-adenine nucleotides.

In some embodiments, the poly-A tail comprises one or more sets of 8-50 consecutive adenine nucleotides. In some embodiments, the poly-A tail comprises one or more sets of 8-100 consecutive adenine nucleotides. For poly-A tails with multiple sets of consecutive adenine nucleotides, i.e. multiple homopolymer sequences, each set of adenine nucleotides does not need to be the same length.

In addition to the number of consecutive adenine nucleotides, a poly-A tail may also be characterized by the number of total adenine nucleotides. The number of total adenine nucleotides is simply the sum of all adenine nucleotides in a poly-A tail. All adenine nucleotides in different groups of consecutive or non-consecutive groupings of adenine nucleotides would therefore be included in the number of total adenine nucleotides in a poly-A tail.

In some embodiments, the poly-A tail comprises 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, 290-300, 300-310, 310-320, 320-330, 330-340, 340-350, 350-360, 360-370, 370-380, 380-390, 390-400, 400-410, 410-420, 420-430, 430-440, 440-450, 450-460, 460-470, 470-480, 480-490, 490-500, 500-510, 510-520, 520-530, 530-540, 540-550, 550-560, 560-570, 570-580, 580-590, or 590-600 total adenine nucleotides. In some embodiments, the poly-A tail comprises one or more homopolymer A sequence of at least 8, 9, 10, 12, 25, 30, 50 nucleotides in length.

In some embodiments, the poly-A tail comprises 40-1000, 40-900, 40-800, 40-700, 40-600, 40-500, 40-400, 40-300, 40-200, or 40-100 total adenine nucleotides.

In some embodiments, the poly-A tail comprises at least 40 total adenine nucleotides. In some embodiments, the poly-A tail comprises at least 50 total adenine nucleotides. In some embodiments, the poly-A tail comprises at least 40, 50, 60, 70 80, 90, 100, 110, 120, 130, 140, 150, 160, 170, 180, 190, 200, 220, 240, 260, 280, or 300 adenine nucleotides.

In some embodiments, the poly-A tail comprises or contains 90, 91, 92, 93, 94, 95, 96, or 97 total adenine nucleotides. In some embodiments, the poly-A tail comprises or contains 96 or 97 total adenine nucleotides.

In some embodiments, the adenine nucleotides are adenosine monophosphate. The nucleotides may be modified.

B. Interrupting Sequences Comprising Non-Adenine Nucleotides

Non-adenine nucleotides of the present invention may comprise or consist of natural or non-natural nucleotides such as guanine, cytosine, or thymine. The nucleotides may be modified.

In some embodiments, a poly-A tail comprises one non-adenine nucleotide in a poly-A tail that otherwise consists only of adenine nucleotides. The one non-adenine nucleotide may interrupt a sequence of adenine nucleotides. The one non-adenine nucleotide may be selected from guanine, cytosine, and thymine. In some embodiments, the one non-adenine nucleotide is a guanine nucleotide. In some embodiments, the one non-adenine nucleotide is a cytosine nucleotide. In some embodiments, the one non-adenine nucleotide is a thymine nucleotide. The interrupting sequence may be a mononucleotide, dinucleotide, trinucleotide sequence. The interrupting sequence may comprise 1, 2, 3, 4, 5, or more non-adenine nucleotides and it may be 1, 2, 3, 4, 5, 6, 7, 8, 9, 10, or more nucleotides in length.

In some embodiments, a single non-adenine nucleotide may interrupt sets or groups of consecutive adenine nucleotides. The one non-adenine nucleotide may be positioned to interrupt consecutive adenine nucleotides in such a way that a poly-A binding protein can bind to a stretch of consecutive adenine nucleotides.

In some embodiments, there are more than one non-adenine nucleotides in a poly-A tail. The more than one non-adenine nucleotide may be positioned to interrupt consecutive adenine nucleotides in such a way that a poly-A binding protein can bind to a stretch of consecutive adenine nucleotides. In some embodiments, non-adenine nucleotides are interspersed between more than one set of consecutive adenine nucleotides, with the number of adenine nucleotides in each series of consecutive adenine nucleotides being sufficient to allow binding of a poly-A binding protein.

The non-adenine nucleotides may be in stretches of more than one non-adenine nucleotide. The non-adenine nucleotides may be in stretches of 2-10 consecutive nucleotides that comprise one or more non-adenine nucleotides. The non-adenine nucleotides may be in interrupting sequences that are interspersed between more than one set of consecutive adenine nucleotides, e.g., more than one homopolymer A sequence. In some embodiments, the number of consecutive non-adenine nucleotides may be one, two, three, four, or five. In some embodiments, there are consecutive stretches of 2-10 non-adenine nucleotides. In some embodiments, there are consecutive stretches of 2-10 nucleotides comprising at least two non-adenine nucleotides.

The consecutive non-adenine nucleotides may be more than one of the same nucleotide or the consecutive non-adenine nucleotides may be different from each other. For example, the non-adenine nucleotides may be more than one guanine, cytosine, or thymine nucleotides. The non-adenine nucleotides may also be guanine and thymine nucleotides; guanine and cytosine nucleotides; thymine and cytosine nucleotides; or guanine, thymine and cytosine nucleotides. The non-adenine nucleotides may comprise two non-adenine nucleotides selected from one or more of guanine, cytosine, and thymine. The non-adenine nucleotide may comprise three non-adenine nucleotides selected from one or more of guanine, cytosine, and thymine. The non-adenine nucleotide may comprise more than three non-adenine nucleotides selected from one or more of guanine, cytosine, and thymine. The poly-A tail may comprise adenine nucleotides between non-adenine nucleotides at regular or irregular intervals. For example, one may view the poly-A tail as having a pattern, where the pattern is regular or irregular. The key to the pattern is the presence of one or more non-adenine nucleotide anywhere in the poly-A tail so long as there are at least 8 consecutive adenines anywhere along the length. In some embodiments, a poly-A may comprise a stretch of at least 8 consecutive adenine nucleotides anywhere along the length, where the adenine nucleotides are "interrupted" anywhere after 8 or more adenines with one or more non-adenine nucleotide. The interrupting sequence may be one non-adenine nucleotide, or 2 to 10 consecutive nucleotides, optionally comprising at least two non-adenine nucleotides. Each one or consecutive stretch of nucleotides comprising at least two non-adenine nucleotides may be followed by one or more adenines, optionally followed by one or more non-adenine nucleotides, optionally followed by one or more than one adenine nucleotides and so on until the end of the poly-A tail. This pattern of adenine nucleotides/non-adenine nucleotides may repeat at regular or irregular intervals. Alternatively, there may be no pattern, such as where there is only one or one consecutive stretch of 2-10 nucleotides, optionally comprising at least two non-adenine nucleotides along the entire length of poly-A.

II. Exemplary Patterns of Adenine and Non-Adenine Nucleotides in Poly-A Tails

Poly-A tails of this invention may comprise or consist of a number of different patterns of interrupting sequences such as consecutive adenine nucleotides and one or more non-adenine nucleotide.

A poly-A tail may begin with one or a series of consecutive adenine nucleotides followed by a non-adenine nucleotide. A poly-A tail that begins with a series of adenine nucleotides means that the 5' end of the poly-A tail consists of one or a series of consecutive adenine nucleotides with one or more non-adenine nucleotide coming after the consecutive adenine nucleotides. "After," means that the non-adenine nucleotides are 3' to a series of consecutive adenine nucleotides.

In some embodiments, the 5' end of the poly-A tail may consist of a series of consecutive adenine nucleotides followed by one or more non-adenine nucleotide(s). In some embodiments, one or more non-adenine nucleotide(s) is located after at least 8, 9, 10, 11, or 12 consecutive adenine nucleotides. In some embodiments, the one or more non-adenine nucleotide is located after at least 8-50 consecutive adenine nucleotides. In some embodiments, the one or more non-adenine nucleotide is located after at least 8-100 consecutive adenine nucleotides. In some embodiments, the non-adenine nucleotide is after one, two, three, four, five, six, or seven adenine nucleotides and is followed by at least 8 consecutive adenine nucleotides.

In some embodiments, the 5' end of the poly A tail consists of one to eight adenine nucleotides followed by one or more non-adenine nucleotide(s). In such embodiments, the non-adenine nucleotide(s) are followed by more adenine nucleotides. The adenine nucleotides that follow the one or more non-adenine nucleotide comprise at least 8 adenines nucleotides before another non-adenine nucleotide.

The range of size of a group of consecutive adenine nucleotides that begins the poly-A tail may vary. In some embodiments, the 5' end of the poly-A tail consists of 1, 2, 3 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 90, 91, 92, 93, 94, 95, 96, 97, 98, 99, or 100 consecutive adenine nucleotides. Where the first non-adenine nucleotide falls after 1-7 adenine nucleotides, the poly-A tail further comprises a stretch of at least 8 adenine nucleotides after the non-adenine nucleotide.

In some embodiments, the one or more non-adenine nucleotide is located after at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

The poly-A tail may end with a stretch of non-adenine nucleotides at the 3' end. The number of non-adenine nucleotides at the 3' end of the poly-A tail may be 1, 2, 3, 4, 5, 6, 7, 8, 9, or 10 non-adenine nucleotides. Alternatively, the 3' end of the poly-A tail may consist of one or more adenine nucleotides.

The poly-A tail of the present invention may comprise one sequence of consecutive adenine nucleotides followed by one or more non-adenine nucleotides, optionally followed by additional adenine nucleotides. The poly-A tail of the present invention may also comprise more than one sequence of consecutive adenine nucleotides interrupted by one or more non-adenine nucleotides. The sequence of consecutive adenine nucleotides may be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides. The number of non-adenine nucleotides in an interrupting sequence may be 1, 2, 3, 4, 5, 6, 7, 8, 9, or 10 non-adenine nucleotides.

A poly-A tail of the invention may also comprise more than one series of consecutive adenine nucleotides that are interrupted or interspersed with non-adenine nucleotides. The length of the interrupting sequence may be 1, 2, 3, 4, 5, 6, 7, 8, 9, or 10 nucleotides. The length of the interrupting sequence may be 1-3, 1-5, 1-10, 2-10, 2-8, 2-6, or 2-5 nucleotides. The poly-A tails of the invention may comprise more than one set of consecutive adenine nucleotides and an interrupting sequence comprising one non-adenine nucleotide or more than one consecutive stretch of 2-10 non-adenine nucleotides between each set of consecutive adenine nucleotides. The poly-A tails of the invention may comprise more than one set of consecutive adenine nucleotides and one non-adenine nucleotide or more than one consecutive stretch of 2-10 nucleotides comprising at least two non-adenine nucleotides between each set of consecutive adenine nucleotides. The poly-A tails of the invention may comprise more than one set of consecutive adenine nucleotides and one or more interrupting sequences, each comprising one or more non-adenine nucleotide. The sets may each comprise the same or different number of adenine nucleotides. In embodiments with multiple sets of consecutive adenine nucleotides, each set of consecutive adenine nucleotides may be sufficient in length to allow binding of a poly-A binding protein.

In some embodiments, one or more non-adenine nucleotide is an interrupting sequence located at regular intervals with the poly-A tail. By regular intervals, it is meant that a set number of consecutive adenine nucleotides is followed by non-adenine nucleotides in a repeated fashion.

In some embodiments, one or more non-adenine nucleotide is located at irregular intervals with the poly-A tail. By irregular intervals, it is meant that a set number of consecutive adenine nucleotides is followed by non-adenine nucleotides followed by another set of consecutive adenine nucleotides that comprise a different number of adenines than the first set.

In some embodiments, the poly-A tail comprises or contains one non-adenine nucleotide or one consecutive stretch of 2-10 nucleotides non-adenine nucleotides every 8-50 consecutive adenine nucleotides. In some embodiments, the poly-A tail comprises or contains one non-adenine nucleotide or one consecutive stretch of 2-10 non-adenine nucleotides every 8-50 consecutive adenine nucleotides. In some embodiments, the poly-A tail comprises or contains one non-adenine nucleotide or one consecutive stretch of 2-10 nucleotides non-adenine nucleotides every 8-100 consecutive adenine nucleotides. In some embodiments, the poly-A tail comprises or contains one non-adenine nucleotide or one consecutive stretch of 2-10 non-adenine nucleotides every 8-100 consecutive adenine nucleotides.

In some embodiments, the poly-A tail comprises or contains one non-adenine nucleotide or one consecutive stretch of 2-10 nucleotides comprising at least two non-adenine nucleotides every 8-50 consecutive adenine nucleotides. In some embodiments, the poly-A tail comprises or contains one non-adenine nucleotide or one consecutive stretch of 2-10 nucleotides comprising at least two non-adenine nucleotides every 8-50 consecutive adenine nucleotides. In some embodiments, the poly-A tail comprises or contains one non-adenine nucleotide or one consecutive stretch of 2-10 nucleotides comprising at least two non-adenine nucleotides every 8-100 consecutive adenine nucleotides. In some embodiments, the poly-A tail comprises or contains one non-adenine nucleotide or one consecutive stretch of 2-10 nucleotides comprising at least two non-adenine nucleotides every 8-100 consecutive adenine nucleotides.

In some embodiments, the poly-A tail comprises or contains one non-adenine nucleotide or one consecutive stretch of 2-10 nucleotides comprising a non-adenine nucleotide every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, the poly-A tail comprises or contains one non-adenine nucleotide or one consecutive stretch of 2-10 nucleotides comprising at least two non-adenine nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

In some embodiments, number of non-adenine nucleotides may be 1, 2, 3, 4, or 5 consecutive non-adenine nucleotides. In some embodiments, the number of consecutive adenine nucleotides may be 8-50 adenine nucleotides. In some embodiment embodiments, the poly-A tail comprises or contains 1, 2, 3, 4, or 5 consecutive non-adenine nucleotides every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive adenine nucleotides.

The numbers of consecutive adenine nucleotides in a poly-A tail may be 12, 16, 25, 30, or 39. The number of consecutive adenine nucleotides may also be greater than 39. In some embodiments, the poly-A tail comprises or contains 1, 2, 3, 4, or 5 consecutive non-adenine nucleotides every 12 consecutive adenine nucleotides. In some embodiments, the poly-A tail comprises or contains 1, 2, 3, 4, or 5 consecutive non-adenine nucleotides every 16 consecutive adenine nucleotides. In some embodiments, the poly-A tail comprises or contains 1, 2, 3, 4, or 5 consecutive non-adenine nucleotides every 25 consecutive adenine nucleotides. In some embodiments, the poly-A tail comprises or contains 1, 2, 3, 4, or 5 consecutive non-adenine nucleotides every 30 consecutive adenine nucleotides. In some embodiments, the poly-A tail comprises or contains 1, 2, 3, 4, or 5 consecutive non-adenine nucleotides every 39 consecutive adenine nucleotides. The number of consecutive non-adenine nucleotides may also be greater than 5.

Exemplary trinucleotide interrupting sequences include GCG, CCG, GTG, TGG, CGG, GGT, TAT, CAT, CGT, CTC, GAT, CCT, TGT, CGC, CAC, TGC, TCG, TCT, CCC, GAC, TAG, GTT, CTG, and TTT. There are 63 possible trinucleotide interrupting sequences, and 36 trinucleotide interrupting sequences that omit a terminal A. In some embodiments, the poly-A tail comprises one or more trinucleotide interrupting sequences chosen from TGG, CGG, GGT, TAT, CAT, CGT, CTC, GAT, CCT, TGT, CGC, CAC, TGC, TCG, TCT, CCC, GAC, TAG, GTT, CTG, and TTT. In some embodiments, the poly-A tail comprises multiple interrupting sequences designed to minimize hybridization and annealing between 3 or more nucleotides within the sequence encoding the poly-A tail or within the poly-A tail. In certain embodiments, the interrupting sequences that minimize annealing between 3 or more nucleotides are chosen from the 34 trinucleotide interrupting sequences that omit a terminal A. In some embodiments, the interrupting sequences that minimize annealing between 3 or more nucleotides are chosen from TGG, CGG, GGT, TAT, CAT, CGT, CTC, GAT, CCT, TGT, CGC, CAC, TGC, TCG, TCT, CCC, GAC, TAG, GTT, CTG, and TTT. In some embodiments, e.g. SEQ ID NO: 18, the poly-A tail comprises di- and/or tri-nucleotide interrupting sequences chosen from TGG, CGG, GGT, TAT, CAT, CGT, CTC, GAT, CCT, TGT, CGC, CAC, TGC, TCG, TCT, CCC, GAC, TAG, GTT, CTG, TTT, and CG. In certain embodiments, the poly-A tail comprises trinucleotide interrupting sequences chosen from GCG, CCG, and GTG. Exemplary dinucleotide interrupting sequences include CG, GC, CC, GG, TT, CT, TC, GT, and TG. There are 15 possible dinucleotide interrupting sequences, and 9 dinucleotides that do not include a terminal A. Mononucleotide interrupting sequences can be C, G, and T. Note that, with respect to any nucleotide sequence above, when referring to an RNA sequence (such as an mRNA), as opposed to a DNA sequence, T is replaced by U.

One skilled in the art would be able to design a number of different patterns of DNA encoding poly-A tails with consecutive adenine nucleotides and one or more non-adenine nucleotide. Some exemplary poly-A tails comprising at least 8 consecutive adenine nucleotides and one or more adenine-nucleotide are presented, for example, in SEQ ID Nos: 1-5, 10, 11, and 18.

III. Methods of Use

The DNA of this invention may be used for production of mRNA encoded by the DNA. In some embodiments, an mRNA is encoded by the DNA of the invention.

In some embodiments, the DNA of the invention is prepared for production of mRNA. In some embodiments, the DNA is within a vector. In some embodiments, the vector is within a host cell. In some embodiments, an mRNA encoded by the DNA of this invention is used for translating the protein of interest encoded by the DNA.

In some embodiments, the one or more non-adenine nucleotide prevents the loss of one or more adenine nucleotides during DNA replication as compared to the loss that occurs in a DNA comprising a 3' tail of a similar or same length that contains only adenine nucleotides. DNA replication is a necessary step in growth of plasmid for DNA purification. As such, a plasmid comprising the DNA of this invention encoding a poly-A tail comprising at least 8 consecutive adenine nucleotides and one or more non-adenine nucleotide may show improved stability over one more rounds of growth and purification of the plasmid, as compared to a plasmid encoding a poly-A tail consisting only of adenine nucleotides.

A plasmid comprising the DNA of this invention comprising a sequence encoding a poly-A tail comprising at least 8 consecutive adenine nucleotides and one or more non-adenine nucleotide may have greater stability when grown in a host cell compared to a plasmid comprising a DNA comprising a sequence encoding a poly-A tail consisting only of consecutive adenine nucleotides. During growth of the host cell expressing a plasmid with a DNA sequence, a DNA sequence encoding a poly-A tail that comprises consecutive adenine nucleotides and one or more non-adenine nucleotide may be resistant to a decrease in length of the DNA encoding the poly-A tail compared to a poly-A tail consisting only of adenine nucleotides. In some embodiments, a plasmid comprising a DNA encoding a poly-A tail comprising one or more non-adenine nucleotide prevents loss of adenines during growth of a host cell as compared to a plasmid comprising a DNA encoding a poly-A tail comprising only adenine nucleotides.

Any means of growing and purifying a vector known to one skilled in the art may be used for growth of a host cell encoding a plasmid. The process of growth and purification of a vector may also be referred to as plasmid preparation. Standard steps of plasmid purification include growth of a bacterial culture, harvesting and lysis of the bacteria, and purification of plasmid DNA. Many kits are available from various manufacturers to purify plasmid DNA. The step of plasmid preparation may be minipreparation (with expected yield of 20 to 40 µg or 50 to 100 µg of plasmid DNA), midipreparation (with expected yield of 100 to 350 µg of plasmid DNA), maxipreparation (with expected yield of 500-850 µg of plasmid DNA), megapreparation (with expected yield of 1.5-2.5 mg of plasmid DNA), or gigapreparation (with expected yield of 7.5-10 mg of plasmid DNA). For therapeutic mRNA production, plasmids may be produced at scales of 100 mg, 1 g, 10 g, or more. The increased stability and replication efficiency of plasmids encoding poly-A tails with non-adenine nucleotides as described herein may improve the consistency and efficiency of plasmids made at such scales.

In some embodiments, a method of producing mRNA from a DNA vector of the present invention is encompassed. In some embodiments, the method of producing mRNA from the DNA vector comprises linearizing the vector downstream of the poly-A tail; denaturing the linearized vector; and contacting the denaturized DNA with an RNA polymerase in the presence of RNA nucleotides such as guanine, cytosine, uracil, adenine, or chemically modified version of such nucleotides such as pseudouridine, N-1-methyl pseudouridine, methoxyuridine, among others. Modified residues, such as base, sugar, and backbone modifications of nucleotide residues can be used in the mRNAs, polynucleotides, and methods described herein.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Description of Sequences

This table provides a listing of certain sequences referenced herein. Note again that, when referring to the RNA version of a DNA sequence in the table below, T is replaced by U. When referring to a DNA version of an RNA sequence in the table below, U is replaced by T.

TABLE 1

| Description | Sequence | SEQ ID No |
|---|---|---|
| sequence of an exemplary poly-A tail comprising non-adenine nucleotides with 30, 30, and 39 consecutive adenosines and ending with non-adenine nucleotides | AAAAAAAAAA AAAAAAAAAA AAAAAAAAAA GCGAAAAAAA AAAAAAAAAA AAAAAAAAAA AAACCGAAAA AAAAAAAAAA AAAAAAAAAA AAAAAAAAAA AAAAACCC | 1 |
| 30PA-sequence of an exemplary poly-A tail comprising non-adenine nucleotides with 30, 30, and 39 consecutive adenosines | AAAAAAAAAA AAAAAAAAAA AAAAAAAAAA GCGAAAAAAA AAAAAAAAAA AAAAAAAAAA AAACCGAAAA AAAAAAAAAA AAAAAAAAAA AAAAAAAAAA AAAA | 2 |
| 25PA-sequence of an exemplary poly-A tail comprising non-adenine nucleotides with four sets of 25 consecutive adenosines | AAAAAAAAAA AAAAAAAAAA AAAAAGCGAA AAAAAAAAAA AAAAAAAAAA AAACCGAAAA AAAAAAAAAA AAAAAAAAAA AGTGAAAAAA AAAAAAAAAA AAAAAAAAA | 3 |
| 16PA-sequence of an exemplary poly-A tail comprising non-adenine nucleotides with six sets of 16 consecutive adenosines | AAAAAAAAAA AAAAAGAAA AAAAAAAAAA AAACAAAAAA AAAAAAAAAA TAAAAAAAAA AAAAAAATAA AAAAAAAAAA AAAACAAAAA AAAAAAAAAA A | 4 |
| 16PA long-sequence of an exemplary poly-A tail comprising non-adenine nucleotides with six sets of 16 consecutive adenosines and 63 consecutive adenosines | AAAAAAAAAA AAAAAGAAA AAAAAAAAAA AAACAAAAAA AAAAAAAAAA TAAAAAAAAA AAAAAAATAA AAAAAAAAAA AAAACAAAAA AAAAAAAAAA ACAAAAAAAA AAAAAAAAAA AAAAAAAAAA AAAAAAAAAA AAAAAAAAAA AAAAA | 5 |
| Cas9 mRNA with a poly-A tail consisting of 97 adenosines | TAATACGACTCACTATAGGGTCCCGCAGTCGGCGTCCAGC GGCTCTGCTTGTTCGTGTGTGTGTCGTTGCAGGCCTTATT CGGATCCATGGATAAGAAGTACTCAATCGGGCTGGATATC GGAACTAATTCCGTGGGTTGGGCAGTGATCACGGATGAAT ACAAAGTGCCGTCCAAGAAGTTCAAGGTCCTGGGGAACAC CGATAGACACAGCATCAAGAAAAATCTCATCGGAGCCCTG CTGTTTGACTCCGGCGAAACCGCAGAAGCGACCCGGCTCA AACGTACCGCGAGGCGACGCTACACCCGGCGGAAGAATCG | 6 |

TABLE 1-continued

| Description | Sequence | SEQ ID No |
|---|---|---|
| | CATCTGCTATCTGCAAGAGATCTTTTCGAACGAAATGGCA | |
| | AAGGTCGACGACAGCTTCTTCCACCGCCTGGAAGAATCTT | |
| | TCCTGGTGGAGGAGGACAAGAAGCATGAACGGCATCCTAT | |
| | CTTTGGAAACATCGTCGACGAAGTGGCGTACCACGAAAAG | |
| | TACCCGACCATCTACCATCTGCGGAAGAAGTTGGTTGACT | |
| | CAACTGACAAGGCCGACCTCAGATTGATCTACTTGGCCCT | |
| | CGCCCATATGATCAAATTCCGCGGACACTTCCTGATCGAA | |
| | GGCGATCTGAACCCTGATAACTCCGACGTGGATAAGCTTT | |
| | TCATTCAACTGGTGCAGACCTACAACCAACTGTTCGAAGA | |
| | AAACCCAATCAATGCTAGCGGCGTCGATGCCAAGGCCATC | |
| | CTGTCCGCCCGGCTGTCGAAGTCGCGGCGCCTCGAAAACC | |
| | TGATCGCACAGCTGCCGGGAGAGAAAAAGAACGGACTTTT | |
| | CGGCAACTTGATCGCTCTCTCACTGGGACTCACTCCCAAT | |
| | TTCAAGTCCAATTTTGACCTGGCCGAGGACGCGAAGCTGC | |
| | AACTCTCAAAGGACACCTACGACGACGACTTGGACAATTT | |
| | GCTGGCACAAATTGGCGATCAGTACGCGGATCTGTTCCTT | |
| | GCCGCTAAGAACCTTTCGGACGCAATCTTGCTGTCCGATA | |
| | TCCTGCGCGTGAACACCGAAATAACCAAAGCGCCGCTTAG | |
| | CGCCTCGATGATTAAGCGGTACGACGAGCATCACCAGGAT | |
| | CTCACGCTGCTCAAAGCGCTCGTGAGACAGCAACTGCCTG | |
| | AAAAGTACAAGGAGATCTTCTTCGACCAGTCCAAGAATGG | |
| | GTACGCAGGGTACATCGATGGAGGCGCTAGCCAGGAAGAG | |
| | TTCTATAAGTTCATCAAGCCAATCCTGGAAAAGATGGACG | |
| | GAACCGAAGAACTGCTGGTCAAGCTGAACAGGGAGGATCT | |
| | GCTCCGGAAACAGAGAACCTTTGACAACGGATCCATTCCC | |
| | CACCAGATCCATCTGGGTGAGCTGCACGCCATCTTGCGGC | |
| | GCCAGGAGGACTTTTACCCATTCCTCAAGGACAACCGGGA | |
| | AAAGATCGAGAAAATTCTGACGTTCCGCATCCCGTATTAC | |
| | GTGGGCCCACTGGCGCGCGGCAATTCGCGCTTCGCGTGGA | |
| | TGACTAGAAAATCAGAGGAAACCATCACTCCTTGGAATTT | |
| | CGAGGAAGTTGTGGATAAGGGAGCTTCGGCACAAAGCTTC | |
| | ATCGAACGAATGACCAACTTCGACAAGAATCTCCCAAACG | |
| | AGAAGGTGCTTCCTAAGCACAGCCTCCTTTACGAATACTT | |
| | CACTGTCTACAACGAACTGACTAAAGTGAAATACGTTACT | |
| | GAAGGAATGAGGAAGCCGGCCTTTCTGTCCGGAGAACAGA | |
| | AGAAAGCAATTGTCGATCTGCTGTTCAAGACCAACCGCAA | |
| | GGTGACCGTCAAGCAGCTTAAAGAGGACTACTTCAAGAAG | |
| | ATCGAGTGTTTCGACTCAGTGGAAATCAGCGGGGTGGAGG | |
| | ACAGATTCAACGCTTCGCTGGGAACCTATCATGATCTCCT | |
| | GAAGATCATCAAGGACAAGGACTTCCTTGACAACGAGGAG | |
| | AACGAGGACATCCTGGAAGATATCGTCCTGACCTTGACCC | |
| | TTTTCGAGGATCGCGAGATGATCGAGGAGAGGCTTAAGAC | |
| | CTACGCTCATCTCTTCGACGATAAGGTCATGAAACAACTC | |
| | AAGCGCCGCCGGTACACTGGTTGGGGCCGCCTCTCCCGCA | |
| | AGCTGATCAACGGTATTCGCGATAAACAGAGCGGTAAAAC | |
| | TATCCTGGATTTCCTCAAATCGGATGGCTTCGCTAATCGT | |
| | AACTTCATGCAATTGATCCACGACGACAGCCTGACCTTTA | |
| | AGGAGGACATCCAAAAGCACAAGTGTCCGGACAGGGAGA | |
| | CTCACTCCATGAACACATCGCGAATCTGGCCGGTTCGCCG | |
| | GCGATTAAGAAGGGAATTCTGCAAACTGTGAAGGTGGTCG | |
| | ACGAGCTGGTGAAGGTCATGGGACGGCACAAACCGGAGAA | |
| | TATCGTGATTGAAATGGCCCGAGAAAACCAGACTACCCAG | |
| | AAGGGCCAGAAAAACTCCCGCGAAAGGATGAAGCGGATCG | |
| | AAGAAGGAATCAAGGAGCTGGGCAGCCAGATCCTGAAAGA | |
| | GCACCCGGTGGAAAACACGCAGCTGCAGAACGAGAAGCTC | |
| | TACCTGTACTATTTGCAAAATGGACGGGACATGTACGTGG | |
| | ACCAAGAGCTGGACATCAATCGGTTGTCTGATTACGACGT | |
| | GGACCACATCGTTCCACAGTCCTTTCTGAAGGATGACTCG | |
| | ATCGATAACAAGGTGTTGACTCGCAGCGACAAGAACAGAG | |
| | GGAAGTCAGATAATGTGCCATCGGAGGAGGTCGTGAAGAA | |
| | GATGAAGAATTACTGGCGGCAGCTCCTGAATGCGAAGCTG | |
| | ATTACCCAGAGAAAGTTTGACAATCTCACTAAAGCCGAGC | |
| | GCGGCGGACTCTCAGAGCTGGATAAGGCTGGATTCATCAA | |
| | ACGGCAGCTGGTCGAGACTCGGCAGATTACCAAGCACGTG | |
| | GCGCAGATCTTGGACTCCCGCATGAACACTAAATACGACG | |
| | AGAACGATAAGCTCATCCGGGAAGTGAAGGTGATTACCCT | |
| | GAAAAGCAAACTTGTGTCGGACTTTCGGAAGGACTTTCAG | |
| | TTTTACAAAGTGAGAGAAATCAACAACTACCATCACGCGC | |
| | ATGACGCATACCTCAACGCTGTGGTCGGTACCGCCCTGAT | |
| | CAAAAAGTACCCTAAACTTGAATCGGAGTTTGTGTACGGA | |
| | GACTACAAGGTCTACGACGTGAGGAAGATGATAGCCAAGT | |
| | CCGAACAGGAAATCGGGAAAGCAACTGCGAAATACTTCTT | |
| | TTACTCAAACATCATGAACTTTTTCAAGACTGAAATTACG | |
| | CTGGCCAATGGAGAAATCAGGAAGAGGCCACTGATCGAAA | |
| | CTAACGGAGAAACGGGCGAAATCGTGTGGGACAAGGGCAG | |
| | GGACTTCGCAACTGTTCGCAAAGTGCTCTCTATGCCGCAA | |

TABLE 1-continued

| Description | Sequence | SEQ ID No |
|---|---|---|
| | GTCAATATTGTGAAGAAAACCGAAGTGCAAACCGGCGGAT<br>TTTCAAAGGAATCGATCCTCCCAAAGAGAAATAGCGACAA<br>GCTCATTGCACGCAAGAAAGACTGGGACCCGAAGAAGTAC<br>GGAGGATTCGATTCGCCGACTGTCGCATACTCCGTCCTCG<br>TGGTGGCCAAGGTGGAGAAGGGAAAGAGCAAAAAGCTCAA<br>ATCCGTCAAAGAGCTGCTGGGGATTACCATCATGGAACGA<br>TCCTCGTTCGAGAAGAACCCGATTGATTTCCTCGAGGCGA<br>AGGGTTACAAGGAGGTGAAGAAGGATCTGATCATCAAACT<br>CCCCAAGTACTCACTGTTCGAACTGGAAAATGGTCGGAAG<br>CGCATGCTGGCTTCGGCCGGAGAACTCCAAAAAGGAAATG<br>AGCTGGCCTTGCCTAGCAAGTACGTCAACTTCCTCTATCT<br>TGCTTCGCACTACGAAAAACTCAAAGGGTCACCGGAAGAT<br>AACGAACAGAAGCAGCTTTTCGTGGAGCAGCACAAGCATT<br>ATCTGGATGAAATCATCGAACAAATCTCCGAGTTTTCAAA<br>GCGCGTGATCCTCGCCGACGCCAACCTCGACAAAGTCCTG<br>TCGGCCTACAATAAGCATAGAGATAAGCCGATCAGAGAAC<br>AGGCCGAGAACATTATCCACTTGTTCACCCTGACTAACCT<br>GGGAGCCCCAGCCGCCTTCAAGTACTTCGATACTACTATC<br>GATCGCAAAAGATACACGTCCACCAAGGAAGTTCTGGACG<br>CGACCCTGATCCACCAAAGCATCACTGGACTCTACGAAAC<br>TAGGATCGATCTGTCGCAGCTGGGTGGCGATGGCGGTGGA<br>TCTCCGAAAAGAAGAGAAAGGTGTAATGAGCTAGCCATC<br>ACATTTAAAAGCATCTCAGCCTACCATGAGAATAAGAGAA<br>AGAAAATGAAGATCAATAGCTTATTCATCTCTTTTTCTTT<br>TTCGTTGGTGTAAAGCCAACACCCTGTCTAAAAAACATAA<br>ATTTCTTTAATCATTTTGCCTCTTTTCTCTGTGCTTCAAT<br>TAATAAAAAATGGAAAGAACCTCGAGAAAAAAAAAAAAAA<br>AAAAAAAAAAAAAAAAAAAAAAAAAAAAAAAAAAAAAAAA<br>AAAAAAAAAAAAAAAAAAAAAAAAAAAAAAAAAAAAAAAA<br>AAA | |
| T7 promoter and Cas9 mRNA with a poly-A tail comprising SEQ ID NO: 1 | TAATACGACT CACTATAGGG TCCCGCAGTC<br>GGCGTCCAGC GGCTCTGCTT GTTCGTGTGT<br>GTGTCGTTGC AGGCCTTATT CGGATCTGCC<br>ACCATGGATA AGAAGTACTC GATCGGGCTG<br>GATATCGGAA CTAATTCCGT GGGGTTGGGCA<br>GTGATCACGG ATGAATACAA AGTGCCGTCC<br>AAGAAGTTCA AGGTCCTGGG GAACACCGAT<br>AGACACAGCA TCAAGAAGAA TCTCATCGGA<br>GCCCTGCTGT TTGACTCCGG CGAAACCGCA<br>GAAGCGACCC GGCTCAAACG TACCGCGAGG<br>CGACGCTACA CCCGGCGGAA GAATCGCATC<br>TGCTATCTGC AAGAAATCTT TTCGAACGAA<br>ATGGCAAAGG TGGACGACAG CTTCTTCCAC<br>CGCCTGGAAG AATCTTTCCT GGTGGAGGAG<br>GACAAGAAGC ATGAACGGCA TCCTATCTTT<br>GGAAACATCG TGGACGAAGT GGCGTACCAC<br>GAAAAGTACC CGACCATCTA CCATCTGCGG<br>AAGAAGTTGG TTGACTCAAC TGACAAGGCC<br>GACCTCAGAT TGATCTACTT GGCCCTCGCC<br>CATATGATCA AATTCCGCGG ACACTTCCTG<br>ATCGAAGGCG ATCTGAACCC TGATAACTCC<br>GACGTGGATA AGCTGTTCAT TCAACTGGTG<br>CAGACCTACA ACCAACTGTT CGAAGAAAAC<br>CCAATCAATG CCAGCGGCGT CGATGCCAAG<br>GCCATCCTGT CCGCCCGGCT GTCGAAGTCG<br>CGGCGCCTCG AAAACCTGAT CGCACAGCTG<br>CCGGGAGAGA AGAAGAACGG ACTTTTCGGC<br>AACTTGATCG CTCTCTCACT GGGACTCACT<br>CCCAATTTCA AGTCCAATTT TGACCTGGCC<br>GAGGACGCGA AGCTGCAACT CTCAAAGGAC<br>ACCTACGACG ACGACTTGGA CAATTTGCTG<br>GCACAAATTG GCGATCAGTA CGCGGATCTG<br>TTCCTTGCCG CTAAGAACCT TTCGGACGCA<br>ATCTTGCTGT CCGATATCCT GCGCGTGAAC<br>ACCGAAATAA CCAAAGCGCC GCTTAGCGCC<br>TCGATGATTA AGCGGTACGA CGAGCATCAC<br>CAGGATCTCA CGCTGCTCAA AGCGCTCGTG<br>AGACAGCAAC TGCCTGAAAA GTACAAGGAG<br>ATTTTCTTCG ACCAGTCCAA GAATGGGTAC<br>GCAGGGTACA TCGATGGAGG CGCCAGCCAG<br>GAAGAGTTCT ATAAGTTCAT CAAGCCAATC<br>CTGGAAAAGA TGGACGGAAC CGAAGAACTG<br>CTGGTCAAGC TGAACAGGGA GGATCTGCTC<br>CGCAAACAGA GAACCTTTGA CAACGGAAGC<br>ATTCCACACC AGATCCATCT GGGTGAGCTG | 7 |

TABLE 1-continued

| Description | Sequence | SEQ ID No |
|---|---|---|
| | CACGCCATCT TGCGGCGCCA GGAGGACTTT | |
| | TACCCATTCC TCAAGGACAA CCGGGAAAAG | |
| | ATCGAGAAAA TTCTGACGTT CCGCATCCCG | |
| | TATTACGTGG GCCCACTGGC GCGCGGCAAT | |
| | TCGCGCTTCG CGTGGATGAC TAGAAAATCA | |
| | GAGGAAACCA TCACTCCTTG GAATTTCGAG | |
| | GAAGTTGTGG ATAAGGGAGC TTCGGCACAA | |
| | TCCTTCATCG AACGAATGAC CAACTTCGAC | |
| | AAGAATCTCC CAAACGAGAA GGTGCTTCCT | |
| | AAGCACAGCC TCCTTTACGA ATACTTCACT | |
| | GTCTACAACG AACTGACTAA AGTGAAATAC | |
| | GTTACTGAAG GAATGAGGAA GCCGGCCTTT | |
| | CTGAGCGGAG AACAGAAGAA AGCGATTGTC | |
| | GATCTGCTGT TCAAGACCAA CCGCAAGGTG | |
| | ACCGTCAAGC AGCTTAAAGA GGACTACTTC | |
| | AAGAAGATCG AGTGTTTCGA CTCAGTGGAA | |
| | ATCAGCGGAG TGGAGGACAG ATTCAACGCT | |
| | TCGCTGGGAA CCTATCATGA TCTCCTGAAG | |
| | ATCATCAAGG ACAAGGACTT CCTTGACAAC | |
| | GAGGAGAACG AGGACATCCT GGAAGATATC | |
| | GTCCTGACCT TGACCCTTTT CGAGGATCGC | |
| | GAGATGATCG AGGAGAGGCT TAAGACCTAC | |
| | GCTCATCTCT TCGACGATAA GGTCATGAAA | |
| | CAACTCAAGC GCCGCCGGTA CACTGGTTGG | |
| | GGCCGCCTCT CCCGCAAGCT GATCAACGGT | |
| | ATTCGCGATA AACAGAGCGG TAAAACTATC | |
| | CTGGATTTCC TCAAATCGGA TGGCTTCGCT | |
| | AATCGTAACT TCATGCAGTT GATCCACGAC | |
| | GACAGCCTGA CCTTTAAGGA GGACATCCAG | |
| | AAAGCACAAG TGAGCGGACA GGGAGACTCA | |
| | CTCCATGAAC ACATCGCGAA TCTGGCCGGT | |
| | TCGCCGGCGA TTAAGAAGGG AATCCTGCAA | |
| | ACTGTGAAGG TGGTGGACGA GCTGGTGAAG | |
| | GTCATGGGAC GGCACAAACC GGAGAATATC | |
| | GTGATTGAAA TGGCCCGAGA AAACCAGACT | |
| | ACCCAGAAGG GCCAGAAGAA CTCCCGCGAA | |
| | AGGATGAAGC GGATCGAAGA AGGAATCAAG | |
| | GAGCTGGGCA GCCAGATCCT GAAAGAGCAC | |
| | CCGGTGGAAA ACACGCAGCT GCAGAACGAG | |
| | AAGCTCTACC TGTACTATTT GCAAAATGGA | |
| | CGGGACATGT ACGTGGACCA AGAGCTGGAC | |
| | ATCAATCGGT TGTCTGATTA CGACGTGGAC | |
| | CACATCGTTC CACAGTCCTT TCTGAAGGAT | |
| | GACTCCATCG ATAACAAGGT GTTGACTCGC | |
| | AGCGACAAGA ACAGAGGGAA GTCAGATAAT | |
| | GTGCCATCGG AGGAGGTCGT GAAGAAGATG | |
| | AAGAATTACT GGCGGCAGCT CCTGAATGCG | |
| | AAGCTGATTA CCCAGAGAAA GTTTGACAAT | |
| | CTCACTAAAG CCGAGCGCGG CGGACTCTCA | |
| | GAGCTGGATA AGGCTGGATT CATCAAACGG | |
| | CAGCTGGTCG AGACTCGGCA GATTACCAAG | |
| | CACGTGGCGC AGATCCTGGA CTCCCGCATG | |
| | AACACTAAAT ACGACGAGAA CGATAAGCTC | |
| | ATCCGGGAAG TGAAGGTGAT TACCCTGAAA | |
| | AGCAAACTTG TGTCGGACTT TCGGAAGGAC | |
| | TTTCAGTTTT ACAAAGTGAG AGAAATCAAC | |
| | AACTACCATC ACGCGCATGA CGCATACCTC | |
| | AACGCTGTGG TCGGCACCGC CCTGATCAAG | |
| | AAGTACCCTA AACTTGAATC GGAGTTTGTG | |
| | TACGGAGACT ACAAGGTCTA CGACGTGAGG | |
| | AAGATGATAG CCAAGTCCGA ACAGGAAATC | |
| | GGGAAAGCAA CTGCGAAATA CTTCTTTTAC | |
| | TCAAACATCA TGAACTTCTT CAAGACTGAA | |
| | ATTACGCTGG CCAATGGAGA AATCAGGAAG | |
| | AGGCCACTGA TCGAAACTAA CGGAGAAACG | |
| | GGCGAAATCG TGTGGGACAA GGGCAGGGAC | |
| | TTCGCAACTG TTCGCAAAGT GCTCTCTATG | |
| | CCGCAAGTCA ATATTGTGAA GAAAACCGAA | |
| | GTGCAAACCG GCGGATTTTC AAAGGAATCG | |
| | ATCCTCCCAA AGAGAAATAG CGACAAGCTC | |
| | ATTGCACGCA AGAAAGACTG GGACCCGAAG | |
| | AAGTACGGAG GATTCGATTC GCCGACTGTC | |
| | GCATACTCCG TCCTCGTGGT GGCCAAGGTG | |
| | GAGAAGGGAA AGAGCAAGAA GCTCAAATCC | |
| | GTCAAAGAGC TGCTGGGGAT TACCATCATG | |
| | GAACGATCCT CGTTCGAGAA GAACCCGATT | |

TABLE 1-continued

| Description | Sequence | SEQ ID No |
|---|---|---|
| | GATTTCCTGG AGGCGAAGGG TTACAAGGAG<br>GTGAAGAAGG ATCTGATCAT CAAACTGCCC<br>AAGTACTCAC TGTTCGAACT GGAAAATGGT<br>CGGAAGCGCA TGCTGGCTTC GGCCGGAGAA<br>CTCCAGAAAG GAAATGAGCT GGCCTTGCCT<br>AGCAAGTACG TCAACTTCCT CTATCTTGCT<br>TCGCACTACG AGAAACTCAA AGGGTCACCG<br>GAAGATAACG AACAGAAGCA GCTTTTCGTG<br>GAGCAGCACA AGCATTATCT GGATGAAATC<br>ATCGAACAAA TCTCCGAGTT TTCAAAGCGC<br>GTGATCCTCG CCGACGCCAA CCTCGACAAA<br>GTCCTGTCGG CCTACAATAA GCATAGAGAT<br>AAGCCGATCA GAGAACAGGC CGAGAACATT<br>ATCCACTTGT TCACCCTGAC TAACCTGGGA<br>GCTCCAGCCG CCTTCAAGTA CTTCGATACT<br>ACTATCGACC GCAAAAGATA CACGTCCACC<br>AAGGAAGTTC TGGACGCGAC CCTGATCCAC<br>CAAAGCATCA CTGGACTCTA CGAAACTAGG<br>ATCGATCTGT CGCAGCTGGG TGGCGATGGT<br>GGCGGTGGAT CCTACCCATA CGACGTGCCT<br>GACTACGCCT CCGGAGGTGG TGGCCCCAAG<br>AAGAAACGGA AGGTGTGATA GCTAGCCATC<br>ACATTTAAAA GCATCTCAGC CTACCATGAG<br>AATAAGAGAA AGAAAATGAA GATCAATAGC<br>TTATTCATCT CTTTTTCTTT TTCGTTGGTG<br>TAAAGCCAAC ACCCTGTCTA AAAAACATAA<br>ATTTCTTTAA TCATTTTGCC TCTTTTCTCT<br>GTGCTTCAAT TAATAAAAAA TGGAAAGAAC<br>CTCGAGAAAA AAAAAAAAAA AAAAAAAAAA<br>AAAAAAGCGA AAAAAAAAAA AAAAAAAAAA<br>AAAAAAAAAC GAAAAAAAAA AAAAAAAAAA<br>AAAAAAAAAA AAAAAAAAAA A | |
| Single guide RNA targeting SEAP | mC*mU*mC*C CUGAUGGAGA UGACAGGUUU<br>UAGAmGmCmU mAmGmAmAmA mUmAmGmCAA<br>GUUAAAAUAA GGCUAGUCCG UUAUCAmAmC<br>mUmUmGmAmA mAmAmAmGmU mGmGmCmAmC<br>mCmGmAmGmU mCmGmGmUmG<br>mCmUmUmU *mU | 8 |
| Single guide RNA targeting mouse TTR | mU*mU*mA*CAGCCACGUCUACAGCAGUUUUAGAmGmCmU<br>mAmGmAmAm<br>AmUmAmGmCAAGUUAAAAUAAGGCUAGUCCGUUAUCAmAm<br>CmUmUmGm<br>AmAmAmAmAmGmUmGmGmCmAmCmCmGmAmGmUmCmGmGm<br>UmGmCmU*<br>mUmUmU | 9 |
| 12PA-sequence of an exemplary poly-A tail comprising non-adenine nucleotides with nine sets of 12 consecutive adenosines and mononucleotide interrupting sequences | AAAAAAAAAAAATAAAAAAAAAAAATAAAAAAAAAAACA<br>AAAAAAAAAAATAAAAAAAAAAAACAAAAAAAAAAAGAA<br>AAAAAAAAAACAAAAAAAAAAAATAAAAAAAAAAAA | 10 |
| 8PA-sequence of an exemplary poly-A tail comprising non-adenine nucleotides with twelve sets of 8 consecutive adenosines and mononucleotide interrupting sequences | AAAAAAAATAAAAAAAATAAAAAAACAAAAAAAAAAAA<br>AAAGAAAAAAAATAAAAAAAACAAAAAAAACAAAAAAAT<br>AAAAAAAAGAAAAAAAACAAAAAAAATAAAAAAAA | 11 |
| PolyA-1 Bcl11a primer annealing sites flanking sequence comprising five interrupting sequences separating six repeats of 12 consecutive adenosines | TCTTCCTTCAGTCTGTAAACCTCAGCTCGAGAAAAAAAAA<br>AAATGGAAAAAAAAAAACGGAAAAAAAAAAAAGGTAAAA<br>AAAAAAAATATAAAAAAAAAAACATAAAAAAAAAAAACG<br>TTCATATCGGTTCTAGACCACACTTCTTACTGAGGTCCC | 12 |

TABLE 1-continued

| Description | Sequence | SEQ ID No |
|---|---|---|
| PolyA-2 Bcl11a primer annealing sites flanking sequence comprising five interrupting sequences separating six sets of 12 consecutive adenosines | TCTTCCTTCAGTCTGTAAACCTCAGAATTCATCTAGCTCG AGAAAAAATTCGAAAAAAAAAAAACGTAAAAAAAAAAAAC TCAAAAAAAAAAAAGATAAAAAAAAAAAAACCTAAAAAAAA AAAATGTAAAAAAAAAAAAAGGGAAAGTCTTCCATATCGGT TCTAGACCACACTTCTTACTGAGGTCCC | 13 |
| PolyA-3 Bcl11a primer annealing sites flanking sequence comprising five interrupting sequences separating six sets of 12 consecutive adenosines | TCTTCCTTCAGTCTGTAAACCTCAGCTCGAGGAAGACAAG GGAAAAAAAAAAAACGCAAAAAAAAAAAAACACAAAAAAAA AAAATGCAAAAAAAAAAAAATCGAAAAAAAAAAAAATCTAAA AAAAAAAAACGTTCATATCGGTTCTAGACCACACTTCTTA CTGAGGTCCC | 14 |
| PolyA-4 Blcl1a primer annealing sites flanking sequence comprising six interrupting sequences separating seven sets of 12 consecutive adenosines | TCTTCCTTCAGTCTGTAAACCTCAGCTCGAGAAAAAATTC GAAAAAAAAAAAACCCAAAAAAAAAAAAGACAAAAAAAAA AAATAGAAAAAAAAAAAAAGTTAAAAAAAAAAAAACTGAAAA AAAAAAATTTAAAAAAAAAAAAATCTAGACCACACTTCTT ACTGAGGTCCC | 15 |
| PolyA 1-2 Blcl1a primer annealing sites flanking sequence comprising 11 interrupting sequences separating 12 sets of 12 consecutive adenosines | TCTTCCTTCAGTCTGTAAACCTCAGAATTCATCTAGCTCG AGAAAAAAAAAAAATGGAAAAAAAAAAAACGGAAAAAAAA AAAAGGTAAAAAAAAAAAAATATAAAAAAAAAAAAACATAAA AAAAAAAAACGAAAAAAAAAAAACGTAAAAAAAAAAAAACT CAAAAAAAAAAAAGATAAAAAAAAAAAAACCTAAAAAAAAA AAATGTAAAAAAAAAAAAAGGGAAAGTCTTCCATATCGGTT CTAGACCACACTTCTTACTGAGGTCCC | 16 |
| PolyA 3-4 Blcl1a primer annealing sites flanking sequence comprising 12 interrupting sequences separating 13 sets of 12 consecutive adenosines | TCTTCCTTCAGTCTGTAAACCTCAGCTCGAGGAAGACAAG GGAAAAAAAAAAAACGCAAAAAAAAAAAAACACAAAAAAAA AAAATGCAAAAAAAAAAAAATCGAAAAAAAAAAAAATCTAAA AAAAAAAAACGAAAAAAAAAAAACCCAAAAAAAAAAAAAGA CAAAAAAAAAAAATAGAAAAAAAAAAAAAGTTAAAAAAAAA AAACTGAAAAAAAAAAAAATTTAAAAAAAAAAAAATCTAGAC CACACTTCTTACTGAGGTCCC | 17 |
| 300PA sequence of an exemplary poly-A tail comprising 24 interrupting sequences separating 13 repeats of 12 consecutive adenosines | AAAAAAAAAAAATGGAAAAAAAAAAAACGGAAAAAAAAA AAGGTAAAAAAAAAAAATATAAAAAAAAAAAAACATAAAA AAAAAACGAAAAAAAAAAAACGTAAAAAAAAAAAAACTCA AAAAAAAAAAAGATAAAAAAAAAAAAACCTAAAAAAAAA ATGTAAAAAAAAAAAAAGGGAAAAAAAAAAAACGCAAAAAA AAAAACACAAAAAAAAAAAATGCAAAAAAAAAAAAATCGA AAAAAAAAAAAATCTAAAAAAAAAAAAACGAAAAAAAAAAA CCCAAAAAAAAAAAAGACAAAAAAAAAAAATAGAAAAAAA AAAAAGTTAAAAAAAAAAAACTGAAAAAAAAAAAAATTTAA AAAAAAAA | 18 |
| 100PA-sequence of an exemplary poly-A tail comprising 97 adenine nucleotide homopolymer | AAAAAAAAAA AAAAAAAAAA AAAAAAAAA AAAAAAAAAA AAAAAAAAAA AAAAAAAAA AAAAAAAAAA AAAAAAAAAA AAAAAAAAAA AAAAAA | 19 |
| pUC-M seq2 forward primer | GGGTTATTGTCTCATGAGCG | 20 |
| pUC-M seq reverse primer | TTTTGTGATGCTCGTCAGGG | 21 |
| RN-Ball1a for | TCTTCCTTCAGTCTGTAAACCTCAG | 22 |
| RN-Bo11la rev | GGGACCTCAGTAAGAAGTGTGG | 23 |
| Liv-Udepleted: Cas9 mRNA with a poly-A tail consisting of 98 consecutive adenosines | TCCCGCAGTCGGCGTCCAGCGGCTCTGCTTGTTCGTGTGT GTGTCGTTGCAGGCCTTATTCGGATCCGCCACCATGGACA AGAAGTACAGCATCGGACTGGACATCGGAACAAACAGCGT CGGATGGGCAGTCATCACAGACGAATACAAGGTCCCGAGC AAGAAGTTCAAGGTCCTGGGAAACACAGACAGACACAGCA TCAAGAAGAACCTGATCGGAGCACTGCTGTTCGACAGCGG AGAAACAGCAGAAGCAACAAGACTGAAGAGAACGAAGA AGAAGATACACAAGAAGAAAGAACAGAATCTGCTACCTGC AGGGAAATCTTCAGCAACGAAATGGCAAAGGTCGACGACAG CTTCTTCCACAGACTGGAAGAAAGCTTCCTGGTCGAAGAA GACAAGAAGCACGAAAGACACCCGATCTTCGGAAACATCG TCGACGAAGTCGCATACCACGAAAAGTACCCGACAATCTA | 24 |

TABLE 1-continued

| Description | Sequence | SEQ ID No |
|---|---|---|
| | CCACCTGAGAAAGAAGCTGGTCGACAGCACAGACAAGGCA | |
| | GACCTGAGACTGATCTACCTGGCACTGGCACACATGATCA | |
| | AGTTCAGAGGACACTTCCTGATCGAAGGAGACCTGAACCC | |
| | GGACAACAGCGACGTCGACAAGCTGTTCATCCAGCTGGTC | |
| | CAGACATACAACCAGCTGTTCGAAGAAAACCCGATCAACG | |
| | CAAGCGGAGTCGACGCAAAGGCAATCCTGAGCGCAAGACT | |
| | GAGCAAGAGCAGAAGACTGGAAAACCTGATCGCACAGCTG | |
| | CCGGGAGAAAAGAAGAACGGACTGTTCGGAAACCTGATCG | |
| | CACTGAGCCTGGGACTGACACCGAACTTCAAGAGCAACTT | |
| | CGACCTGGCAGAAGACGCAAAGCTGCAGCTGAGCAAGGAC | |
| | ACATACGACGACGACCTGGACAACCTGCTGGCACAGATCG | |
| | GAGACCAGTACGCAGACCTGTTCCTGCCAGCAAAGAACCT | |
| | GAGCGACGCAATCCTGCTGAGCGACATCCTGAGAGTCAAC | |
| | ACAGAAATCACAAAGGCACCGCTGAGCGCAAGCATGATCA | |
| | AGAGATACGACGAACACCACCAGGACCTGACACTGCTGAA | |
| | GGCACTGGTCAGACAGCAGCTGCCGGAAAAGTACAAGGAA | |
| | ATCTTCTTCGACCAGAGCAAGAACGGATACGCAGGATACA | |
| | TCGACGGAGGAGCAAGCCAGGAAGAATTCTACAAGTTCAT | |
| | CAAGCCGATCCTGGAAAAGATGGACGGAACAGAAGAACTG | |
| | CTGGTCAAGCTGAACAGAGAAGACCTGCTGAGAAAGCAGA | |
| | GAACATTCGACAACGGAAGCATCCCGCACCAGATCCACCT | |
| | GGGAGAACTGCACGCAATCCTGAGAAGACAGGAAGACTTC | |
| | TACCCGTTCCTGAAGGACAACAGAGAAAAGATCGAAAAGA | |
| | TCCTGACATTCAGAATCCCGTACTACGTCGGACCGCTGGC | |
| | AAGAGGAAACAGCAGATTCGCATGGATGACAAGAAAGAGC | |
| | GAAGAAACAATCACACCGTGGAACTTCGAAGAAGTCGTCG | |
| | ACAAGGGAGCAAGCGCACAGAGCTTCATCGAAAGAATGAC | |
| | AAACTTCGACAAGAACCTGCCGAACGAAAAGGTCCTGCCG | |
| | AAGCACAGCCTGCTGTACGAATACTTCACAGTCTACAACG | |
| | AACTGACAAAGGTCAAGTACGTCACAGAAGGAATGAGAAA | |
| | GCCGGCATTCCTGAGCGGAGAACAGAAGAAGGCAATCGTC | |
| | GACCTGCTGTTCAAGACAAACAGAAAGGTCACAGTCAAGC | |
| | AGCTGAAGGAAGACTACTTCAAGAAGATCGAATGCTTCGA | |
| | CAGCGTCGAAATCAGCGGAGTCGAAGACAGATTCAACGCA | |
| | AGCCTGGAACATACCACGACCTGCTGAAGATCATCAAGG | |
| | ACAAGGACTTCCTGGACAACGAAGAAAACGAAGACATCCT | |
| | GGAAGACATCGTCCTGACACTGACACTGTTCGAAGACAGA | |
| | GAAATGATCGAAGAAAGACTGAAGACATACGCACACCTGT | |
| | TCGACGACAAGGTCATGAAGCAGCTGAAGAGAAGAAGATA | |
| | CACAGGATGGGGAAGACTGAGCAGAAAGCTGATCAACGGA | |
| | ATCAGAGACAAGCAGAGCGGAAAGACAATCCTGGACTTCC | |
| | TGAAGAGCGACGGATTCGCAAACAGAAACTTCATGCAGCT | |
| | GATCCACGACGCAGCCTGACATTCAAGGAAGACATCCAG | |
| | AAGGCACAGGTCAGCGGACAGGGAGACAGCCTGCACGAAC | |
| | ACATCGCAAACCTGGCAGGAAGCCCGGCAATCAAGAAGGG | |
| | AATCCTGCAGACAGTCAAGGTCGTCGACGAACTGGTCAAG | |
| | GTCATGGGAAGACACAAGCCGGAAAACATCGTCATCGAAA | |
| | TCGCAAGAGAAAACCACACAACACAGAAGGGACAGAAGAA | |
| | CAGCAGAGAAAGAATGAAGAGAATCGAAGAAGGAATCAAG | |
| | GAACTGGGAAGCCAGATCCTGAAGGAACACCCGGTCGAAA | |
| | ACACACAGCTGCAGAACGAAAAGCTGTACCTGTACTACCT | |
| | GCAGAACGGAAGAGACATGTACGTCGACCAGGAACTGGAC | |
| | ATCAACAGACTGAGCGACTACGACGTCGACCACATCGTCC | |
| | CGCAGAGCTTCCTGAAGGACGACAGCATCGACAACAAGGT | |
| | CCTGACAAGAAGCGACAAGAACAGAGGAAAGAGCGACAAC | |
| | GTCCCGAGCGAAGAAGTCGTCAAGAAGATGAAGAACTACT | |
| | GGAGACAGCTGCTGAACGCAAAGCTGATCACACAGAGAAA | |
| | GTTCGACAACCTGACAAAGGCAGAGAGAGGAGGACTGAGC | |
| | GAACTGGACAAGGCAGGATTCATCAAGAGACAGCTGGTCG | |
| | AAACAAGACAGATCACAAAGCACGTCGCACAGATCCTGGA | |
| | CAGCAGAATGAACACAAAGTACGACGAAAACGACAAGCTG | |
| | ATCAGAGAAGTCAAGGTCATCACACTGAAGAGCAAGCTGG | |
| | TCAGCGACTTCAGAAAGGACTTCCAGTTCTACAAGGTCAG | |
| | AGAAATCAACAACTACCACCACGCACACGACGCATACCTG | |
| | AACGCAGTCGTCGGAACAGCACTGATCAAGAAGTACCCGA | |
| | AGCTGGAAAGCGAATTCGTCTACGGAGACTACAAGGTCTA | |
| | CGACGTCAGAAAGATGATCGCAAAGAGCGAACAGGAAATC | |
| | GGAAAGGCAACAGCAAAGTACTTCTTCTACAGCAACATCA | |
| | TGAACTTCTTCAAGACAGAAATCACACTGGCAAACGGAGA | |
| | AATCAGAAAGAGACCGCTGATCGAAACAAACGGAGAAACA | |
| | GGAGAAATCGTCTGGGACAAGGGAAGAGACTTCGCAACAG | |
| | TCAGAAAGGTCCTGAGCATGCCGCAGGTCAACATCGTCAA | |
| | GAAGACAGAAGTCCAGACAGGAGGATTCAGCAAGGAAAGC | |
| | ATCCTGCCGAAGAGAAACAGCGACAAGCTGATCGCAAGAA | |
| | AGAAGGACTGGGACCCGAAGAAGTACGGAGGATTCGACAG | |
| | CCCGACAGTCGCATACAGCGTCCTGGTCGTCGCAAAGGTC | |

TABLE 1-continued

| Description | Sequence | SEQ ID No |
|---|---|---|
| | GAAAAGGGAAAGAGCAAGAAGCTGAAGAGCGTCAAGGAAC TGCTGGGAATCACAATCATGGAAAGAAGCAGCTTCGAAAA GAACCCGATCGACTTCCTGGAAGCAAAGGGATACAAGGAA GTCAAGAAGGACCTGATCATCAAGCTGCCGAAGTACAGCC TGTTCGAACTGGAAAACGGAAGAAAGAGAATGCTGGCAAG CGCAGGAGAACTGCAGAAGGGAAACGAACTGGCACTGCCG AGCAAGTACGTCAACTTCCTGTACCTGGCAAGCCACTACG AAAAGCTGAAGGGAAGCCCGGAAGACAACGAACAGAAGCA GCTGTTCGTCGAACAGCACAAGCACTACCTGGACGAAATC ATCGAACAGATCAGCGAATTCAGCAAGAGAGTCATCCTGG CAGACGCAAACCTGGACAAGGTCCTGAGCGCATACAACAA GCACAGAGACAAGCCGATCAGAGAACAGGCAGAAAACATC ATCCACCTGTTCACACTGACAAACCTGGGAGCACCGGCAG CATTCAAGTACTTCGACACAACAATCGACAGAAAGAGATA CACAAGCACAAAGGAAGTCCTGGACGCAACACTGATCCAC CAGAGCATACAGGACTGTACGAAACAAGAATCGACCTGA GCCAGCTGGGAGGAGACGGAGGAGGAAGCCCGAAGAAGAA GAGAAAGGTCTAGCTAGCCATCACATTTAAAAGCATCTCA GCCTACCATGAGAATAAGAGAAAGAAAATGAAGATCAATA GCTTATTCATCTCTTTTTCTTTTTCGTTGGTGTAAAGCCA ACACCCTGTCTAAAAAACATAAATTTCTTTAATCATTTTG CCTCTTTTCTCTGTGCTTCAATTAATAAAAAATGGAAAGA ACCTCGAGAAAAAAAAAAAAAAAAAAAAAAAAAAAAAAAA AAAAAAAAAAAAAAAAAAAAAAAAAAAAAAAAAAAAAAAA AAAAAAAAAAAAAAAAAAAAAAAA | |
| Cas9 mRNA with a poly-A tail comprising SEQ ID NO: 3 | TCCCGCAGTCGGCGTCCAGCGGCTCTGCTTGTTCGTGTGT GTGTCGTTGCAGGCCTTATTCGGATCCGCCACCATGGACA AGAAGTACAGCATCGGACTGGACATCGGAACAAACAGCGT CGGATGGGCAGTCATCACAGACGAATACAAGGTCCCGAGC AAGAAGTTCAAGGTCCTGGGAAACACAGACAGACACAGCA TCAAGAAGAACCTGATCGGAGCACTGCTGTTCGACAGCGG AGAAACAGCAGAAGCAACAAGACTGAAGAGAACAGCAAGA AGAAGATACACAAGAAGAAAGAACAGAATCTGCTACCTGC AGGAAATCTTCAGCAACGAAATGGCAAAGGTCGACGACAG CTTCTTCCACAGACTGGAAGAAAGCTTCCTGGTCGAAGAA GACAAGAAGCACGAAAGACACCCGATCTTCGGAAACATCG TCGACGAAGTCGCATACCACGAAAAGTACCCGACAATCTA CCACCTGAGAAAGAAGCTGGTCGACAGCACAGACAAGGCA GACCTGAGACTGATCTACCTGGCACTGGCACACATGATCA AGTTCAGAGGACACTTCCTGATCGAAGGAGACCTGAACCC GGACAACAGCGACGTCGACAAGCTGTTCATCCAGCTGGTC CAGACATACAACCAGCTGTTCGAAGAAAACCCGATCAACG CAAGCGGAGTCGACGCAAAGGCAATCCTGAGCGCAAGACT GAGCAAGAGCAGAAGACTGGAAAACCTGATCGCACAGCTG CCGGGAGAAAAGAAGAACGGACTGTTCGGAAACCTGATCG CACTGAGCCTGGGACTGACACCGAACTTCAAGAGCAACTT CGACCTGGCAGAAGACGCAAAGCTGCAGCTGAGCAAGGAC ACATACGACGACGACCTGGACAACCTGCTGGCACAGATCG GAGACCAGTACGCAGACCTGTTCCTGGCAGCAAAGAACCT GAGCGACGCAATCCTGCTGAGCGACATCCTGAGAGTCAAC ACAGAAATCACAAAGGCACCGCTGAGCGCAAGCATGATCA AGAGATACGACGAACACCACCAGGACCTGACACTCTGAA GGCACTGGTCAGACAGCAGCTGCCGGAAAAGTACAAGGAA ATCTTCTTCGACCAGAGCAAGAACGGATACGCAGGATACA TCGACGGAGGAGCAAGCCAGGAAGAATTCTACAAGTTCAT CAAGCCGATCCTGGAAAAGATGGACGGAACAGAAGAACTG CTGGTCAAGCTGAACAGAGAAGACCTGCTGAGAAAGCAGA GAACATTCCACAACGGAAGCATCCCGCACCAGATCCACCT GGGAGAACTGCACGCAATCCTGAGAAGACAGGAAGACTTC TACCCGTTCCTGAAGGACAACAGAGAAAAGATCGAAAAGA TCCTGACATTCAGAATCCCGTACTACGTCGGACCGCTGGC AAGAGGAAACAGCAGATTCGCATGGATGACAAGAAAGAGC GAAGAAACAATCACACCGTGGAACTTCGAAGAAGTCGTCG ACAAGGGAGCAAGCGCACAGAGCTTCATCGAAAGAATGAC AAACTTCGACAAGAACCTGCCGAACGAAAAGGTCCTGCCG AAGCACAGCCTGCTGTACGAATACTTCACAGTCTACAACG AACTGACAAAGGTCAAGTACGTCACAGAAGGAATGAGAAA GCCGGCATTCCTGAGCGGAGAACAGAAGAAGGCAATCGTC GACCTGCTGTTCAAGACAAACAGAAAGGTCACAGTCAAGC AGCTGAAGGAAGACTACTTCAAGGAGATCGAATGCTTCGA CAGCGTCGAAATCAGCGGAGTCGAAGACAGATTCAACGCA AGCCTGGGAACATACCACGACCTGCTGAAGATCATCAAGG ACAAGGACTTCCTGGACAACGAAGAAAACGAAGACATCCT GGAAGACATCGTCCTGACACTGACACTGTTCGAAGACAGA GAAATGATCGAAGAAAGACTGAAGACATACGCACACCTGT | 25 |

TABLE 1-continued

| Description | Sequence | SEQ ID No |
|---|---|---|
| | TCGACGACAAGGTCATGAAGCAGCTGAAGAGAAGAAGATA<br>CACAGGATGGGGAAGACTGAGCAGAAAGCTGATCAACGGA<br>ATCAGAGACAAGCAGAGCGGAAAGACAATCCTGGACTTCC<br>TGAAGAGCGACGGATTCGCAAACAGAAACTTCATCCAGCT<br>GATCCACGACGACAGCCTGACATTCAAGGAAGACATCCAG<br>AAGGCACAGGTCAGCGGACAGGGAGACAGCCTGCACGAAC<br>ACATCGCAAACCTGGCAGGAAGCCCGGCAATCAAGAAGGG<br>AATCCTGCAGACAGTCAAGGTCGTCGACGAACTGGTCAAG<br>GTCATGGGAAGACACAAGCCGGAAAACATCGTCATCGAAA<br>TGGCAAGAGAAAACCAGACAACACAGAAGGGACAGAAGAA<br>CAGCAGAGAAAGAATGAAGAGAATCGAAGAAGGAATCAAG<br>GAACTGGAAGCCAGATCCTGAAGGAACACCCGGTCGAAA<br>ACACACAGCTGCAGAACGAAAAGCTGTACCTGTACTACCT<br>GCAGAACGGAAGAGACATGTACGTCGACCAGGAACTGGAC<br>ATCAACAGACTGAGCGACTACGACGTCGACCACATCGTCC<br>CGCAGAGCTTCCTGAAGGACGACAGCATCGACAACAAGGT<br>CCTGACAAGAAGCGACAAGAACAGAGGAAAGAGCGACAAC<br>GTCCCGAGCGAAGAAGTCGTCAAGAAGATGAAGAACTACT<br>GGAGACAGCTGCTGAACGCAAAGCTGATCACACAGAGAAA<br>GTTCGACAACCTGACAAAGGCAGAGAGAGGAGGACTGAGC<br>GAACTGGACAAGGCAGGATTCATCAAGAGACAGCTGGTCG<br>AAACAAGACAGATCACAAAGCACGTCGCACAGATCCTGGA<br>CAGCAGAATGAACACAAAGTACGACGAAAACGACAAGCTG<br>ATCAGAGAAGTCAAGGTCATCACACTGAAGAGCAAGCTGG<br>TCAGCGACTTCAGAAAGGACTTCCAGTTCTACAAGGTCAG<br>AGAAATCAACAACTACCACCACGCACACGACGCATACCTG<br>AACGCAGTCGTCGGAACAGCACTGATCAAGAAGTACCCGA<br>AGCTGGAAAGCGAATTCGTCTACGGAGACTACAAGGTCTA<br>CGACGTCAGAAAGATGATCGCAAAGAGCGAACAGGAAATC<br>GGAAAGGCAACAGCAAAGTACTTCTTCTACAGCAACATCA<br>TGAACTTCTTCAAGACAGAAATCACACTGGCAAACGGAGA<br>AATCAGAAAGAGACCGCTGATCGAAACAAACGGAGAAACA<br>GGAGAAATCGTCTGGGACAAGGGAAGAGACTTCGCAACAG<br>TCAGAAAGGTCCTGAGCATGCCGCAGTCAACATCGTCAA<br>GAAGACAGAAGTCCAGACAGGAGGATTCAGCAAGGAAAGC<br>ATCCTGCCGAAGAGAAACAGCGACAAGCTGATCGCAAGAA<br>AGAAGGACTGGGACCCGAAGAAGTACGGAGGATTCGACAG<br>CCCGACAGTCGCATACAGCGTCCTGGTCGTCGCAAAGGTC<br>GAAAAGGGAAAGAGCAAGAAGCTGAAGAGCGTCAAGGAAC<br>TGCTGGGAATCACAATCATGGAAAGAAGCAGCTTCGAAAA<br>GAACCCGATCGACTTCCTGGAAGCAAAGGGATACAAGGAA<br>GTCAAGAAGGACCTGATCATCAAGCTGCCGAAGTACAGCC<br>TCTTCGAACTGGAAAACGGAAGAAAGAGAATGCTGGCAAG<br>CGCAGGAGAACTGCAGAAGGGAAACGAACTGGCACTGCCG<br>AGCAAGTACGTCAACTTCCTGTACCTGGCAAGCCACTACG<br>AAAAGCTGAAGGGAAGCCCGGAAGACAACGAACAGAAGCA<br>GCTGTTCGTCGAACAGCACAAGCACTACCTGGACGAAATC<br>ATCGAACAGATCAGCGAATTCAGCAAGAGAGTCATCCTGG<br>CAGACGCAAACCTGGACAAGGTCCTGAGCGCATACAACAA<br>GCACAGAGACAAGCCGATCAGAGAACAGGCAGAAAACATC<br>ATCCACCTETTCACACTGACAAACCTGGGAGCACCGGCAG<br>CATTCAAGTACTTCGACACAACAATCGACAGAAAGAGATA<br>CACAAGCACAAAGGAAGTCCTGGACGCAACACTGATCCAC<br>CAGAGCATCACAGGACTGTACGAAACAAGAATCGACCTGA<br>GCCAGCTGGGAGGAGACGGAGGAGGAAGCCCGAAGAAGAA<br>GAGAAAGGTCTAGCTAGCCATCACATTTAAAAGCATCTCA<br>GCCTACCATGAGAATAAGAGAAAGAAAATGAAGATCAATA<br>GCTTATTCATCTCTTTTTCTTTTTCGTTGGTGTAAAGCCA<br>ACACCCTGTCTAAAAAACATAAATTTCTTTAATCATTTTG<br>CCTCTTTTCTCTGTGCTTCAATTAATAAAAAATGGAAAGA<br>ACCAAAAAAAAAAAAAAAAAAAAAAAGCGAAAAAAAAA<br>AAAAAAAAAAAAAAACCGAAAAAAAAAAAAAAAAAAAA<br>AAAGTGAAAAAAAAAAAAAAAAAAAAAAAA | |
| Cas9 mRNA with a poly-A tail comprising SEQ ID NO: 4 | TCCCGCAGTCGGCGTCCAGCGGCTCTGCTTGTTCGTGTGT<br>GTGTCGTTECAGGCCTTATTCGGATCCGCCACCATGGACA<br>AGAAGTACAGCATCGGACTGGACATCGGAACAAACAGCGT<br>CGGATGGGCAGTCATCACAGACGAATACAAGGTCCCGAGC<br>AAGAAGTTCAAGGTCCTGGGAAACACAGACAGACACAGCA<br>TCAAGAAGAACCTGATCGGAGCACTGCTGTTCGACAGCGG<br>AGAAACGCAGAAGCAACAAGACTGAAGAGAACGACAAGA<br>AGAAGATACACAAGAAGAAAGAACAGAATCTGCTACCTGC<br>AGGAAATCTTCAGCAACGAAATGGCAAAGGTCGACGACAG<br>CTTCTTCCACAGACTGGAAGAAAGCTTCCTGGTCGAAGAA<br>GACAAGAAGCACGAAAGACACCCGATCTTCGGAAACATCG<br>TCGACGAAGTCGCATACCACGAAAAGTACCCGACAATCTA | 26 |

TABLE 1-continued

| Description | Sequence | SEQ ID No |
|---|---|---|
| | CCACCTGAGAAAGAAGCTGGTCGACAGCACAGACAAGGCA | |
| | GACCTGAGACTGATCTACCTGGCACTGGCACACATGATCA | |
| | AGTTCAGAGGACACTTCCTGATCGAAGGAGACCTGAACCC | |
| | GGACAACAGCGACGTCGACAAGCTGTTCATCCAGCTGGTC | |
| | CAGACATACAACCAGCTGTTCGAAGAAAACCCGATCAACG | |
| | CAAGCGGAGTCGACGCAAAGGCAATCCTGAGCGCAAGACT | |
| | GAGCAAGAGCAGAAGACTGGAAAACCTGATCGCACAGCTG | |
| | CCGGGAGAAAAGAAGAACGGACTGTTCGGAAACCTGATCG | |
| | CACTGAGCCTGGGACTGACACCGAACTTCAAGAGCAACTT | |
| | CGACCTGGCAGAAGACGCAAAGCTGCAGCTGAGCAAGGAC | |
| | ACATACGACGACGACCTGGACAACCTGCTGGCACAGATCG | |
| | GAGACCAGTACGCAGACCTGTTCCTEGCAGCAAAGAACCT | |
| | GAGCGACGCAATCCTGCTGAGCGACATCCTGAGAGTCAAC | |
| | ACAGAAATCACAAAGGCACCGCTGAGCGCAAGCATGATCA | |
| | AGAGATACGACGAACACCACCAGGACCTGACACTECTGAA | |
| | GGCACTGGTCAGACAGCAGCTGCCGGAAAAGTACAAGGAA | |
| | ATCTTCTTCGACCAGAGCAAGAACGGATACGCAGGATACA | |
| | TCGACGGAGGAGCAAGCCAGGAAGAATTCTACAAGTTCAT | |
| | CAAGCCGATCCTGGAAAAGATGGACGGAACAGAAGAACTG | |
| | CTGGTCAAGCTGAACAGAGAAGACCTGCTGAGAAAGCAGA | |
| | GAACATTCGACAACGGAAGCATCCCCCACCAGATCCACCT | |
| | GGGAGAACTGCACGCAATCCTGAGAAGACAGGAAGACTTC | |
| | TACCCGTTCCTGAAGGACAACAGAGAAAAGATCGAAAAGA | |
| | TCCTGACATTCAGAATCCCGTACTACGTCGGACCGCTGGC | |
| | AAGAGGAAACAGCAGATTCGCATGGATGACAAGAAAGAGC | |
| | GAAGAAACAATCACACCGTGGAACTTCGAAGAAGTCGTCG | |
| | ACAAGGGAGCAAGCGCACAGAGCTTCATCGAAAGAATGAC | |
| | AAACTTCGACAAGAACCTGCCGAACGAAAAGGTCCTGCCG | |
| | AAGCACAGCCTGCTGTACGAATACTTCACAGTCTACAACG | |
| | AACTGACAAAGGTCAAGTACGTCACAGAAGGAATGAGAAA | |
| | GCCGGCATTCCTGAGCGGAGAACAGAAGAAGGCAATCGTC | |
| | GACCTGCTGTTCAAGACAAACAGAAAGGTCACAGTCAAGC | |
| | AGCTGAAGGAAGACTACTTCAAGAAGATCGAATGCTTCGA | |
| | CAGCGTCGAAATCAGCGGAGTCGAAGACAGATTCAACGCA | |
| | AGCCTGGAACATACCACGACCTGCTGAAGATCATCAAGG | |
| | ACAAGGACTTCCTGGACAACGAAGAAAACGAAGACATCCT | |
| | GGAAGACATCGTCCTGACACTGACACTGTTCGAAGACAGA | |
| | GAAATGATCGAAGAAAGACTGAAGACATACGCACACCTGT | |
| | TCGACGACAAGGTCATGAAGCAGCTGAAGAGAAGAAGATA | |
| | CACAGGATGGGGAAGACTGAGCAGAAAGCTGATCAACGGA | |
| | ATCAGAGACAAGCAGAGCGGAAAGACAATCCTGGACTTCC | |
| | TGAAGAGCGACGGATTCGCAAACAGAAACTTCATGCAGCT | |
| | GATCCACGACGCAGCCTGACATTCAAGGAAGACATCCAG | |
| | AAGGCACAGGTCAGCGGACAGGGAGACAGCCTGCACGAAC | |
| | ACATCGCAAACCTGGCAGGAAGCCCGGCAATCAAGAAGGG | |
| | AATCCTGCAGACAGTCAAGGTCGTCGACGAACTGGTCAAG | |
| | GTCATGGGAAGACACAAGCCGGAAAACATCGTCATCGAAA | |
| | TGGCAAGAGAAAACCAGACAACACAGAAGGGACAGAAGAA | |
| | CAGCAGAGAAAGAATGAAGAGAATCGAAGAAGGAATCAAG | |
| | GAACTGGGAAGCCAGATCCTGAAGGAACACCCGGTCGAAA | |
| | ACACACAGCTGCAGAACGAAAAGCTGTACCTGTACTACCT | |
| | GCAGAACGGAAGAGACATGTACGTCGACCAGGAACTGGAC | |
| | ATCAACAGACTGAGCGACTACGACGTCGACCACATCGTCC | |
| | CCCAGAGCTTCCTGAAGGACGACAGCATCGACAACAAGGT | |
| | CCTGACAAGAAGCGACAAGAACAGAGGAAAGAGCGACAAC | |
| | GTCCCGAGCGAAGAAGTCGTCAAGAAGATGAAGAACTACT | |
| | GGAGACAGCTGCTGAACGCAAAGCTGATCACACAGAGAAA | |
| | GTTCGACAACCTGACAAAGGCAGAGAGAGGAGGACTGAGC | |
| | GAACTGGACAAGGCAGGATTCATCAAGAGACAGCTGGTCG | |
| | AAACAAGACAGATCACAAAGCACGTCGCACAGATCCTGGA | |
| | CAGCAGAATGAACACAAAGTACGACGAAAACGACAAGCTG | |
| | ATCAGAGAAGTCAAGGTCATCACACTGAAGAGCAAGCTGG | |
| | TCAGCGACTTCAGAAAGGACTTCCAGTTCTACAAGGTCAG | |
| | AGAAATCAACAACTACCACCACGCACACGACGCATACCTG | |
| | AACGCAGTCGTCGGAACAGCACTGATCAAGAAGTACCCGA | |
| | AGCTGGAAAGCGAATTCGTCTACGGAGACTACAAGGTCTA | |
| | CGACGTCAGAAAGATGATCGCAAAGAGCGAACAGGAAATC | |
| | GGAAAGGCAACAGCAAAGTACTTCTTCTACAGCAACATCA | |
| | TGAACTTCTTCAAGACAGAAATCACACTGGCAAACGGAGA | |
| | AATCAGAAAGAGACCGCTGATCGAAACAAACGGAGAAACA | |
| | GGAGAAATCGTCTGGGACAAGGGAAGAGACTTCGCAACAG | |
| | TCAGAAAGGTCCTGAGCATGCCGCAGGTCAACATCGTCAA | |
| | GAAGACAGAAGTCCAGACAGGAGGATTCAGCAAGGAAAGC | |
| | ATCCTGCCGAAGAGAAACAGCGACAAGCTGATCGCAAGAA | |
| | AGAAGGACTGGGACCCGAAGAAGTACGGAGGATTCGACAG | |
| | CCCGACAGTCGCATACAGCGTCCTGGTCGTCGCAAAGGTC | |

TABLE 1-continued

| Description | Sequence | SEQ ID No |
|---|---|---|
| | GAAAAGGGAAAGAGCAAGAAGCTGAAGAGCGTCAAGGAAC<br>TGCTGGGAATCACAATCATGGAAAGAAGCAGCTTCGAAAA<br>GAACCCGATCGACTTCCTGGAAGCAAAGGGATACAAGGAA<br>GTCAAGAAGGACCTGATCATCAAGCTGCCGAAGTACAGCC<br>TGTTCGAACTGGAAAACGGAAGAAAGAGAATGCTGGCAAG<br>CGCAGGAGAACTGCAGAAGGGAAACGAACTGGCACTGCCG<br>AGCAAGTACETCAACTTCCTGTACCTGGCAAGCCACTACG<br>AAAAGCTGAAGGGAAGCCCGGAAGACAACGAACAGAAGCA<br>GCTGTTCGTCGAACAGCACAAGCACTACCTGGACGAAATC<br>ATCGAACAGATCAGCGAATTCAGCAAGAGAGTCATCCTGG<br>CAGACGCAAACCTGGACAAGGTCCTGAGCGCATACAACAA<br>GCACAGAGACAAGCCGATCAGAGAACAGGCAGAAAACATC<br>ATCCACCTGTTCACACTGACAAACCTGGGAGCACCGGCAG<br>CATTCAAGTACTTCGACACAACAATCGACAGAAAGAGATA<br>CACAAGCACAAAGGAAGTCCTGGACGCAACACTGATCCAC<br>CAGAGCATCACAGGACTGTACGAAACAAGAATCGACCTGA<br>GCCAGCTGGGAGGAGACGGAGGAGGAAGCCCGAAGAAGAA<br>GAGAAAGGTCTAGCTAGCCATCACATTTAAAAGCATCTCA<br>GCCTACCATGAGAATAAGAGAAAGAAAATGAAGATCAATA<br>GCTTATTCATCTCTTTTTCTTTTTCETTGGTGTAAAGCCA<br>ACACCCTGTCTAAAAAACATAAATTTCTTTAATCATTTTG<br>CCTCTTTTCTCTGTGCTTCAATTAATAAAAAATGGAAAGA<br>ACCAAAAAAAAAAAAAAGAAAAAAAAAAAAAAAACAAA<br>AAAAAAAAAAAATAAAAAAAAAAAAAAATAAAAAAAAA<br>AAAAAACAAAAAAAAAAAAAAAA | |
| Cas9 mRNA with a poly-A tail comprising SEQ ID NO: 5 | TCCCGCAGTCGGCGTCCAGCGGCTCTGCTTGTTCGTGTGT<br>GTGTCGTTGCAGGCCTTATTCGGATCCGCCACCATGGACA<br>AGAAGTACAGCATCGGACTGGACATCGGAACAAACAGCGT<br>CGGATGGGCAGTCATCACAGACGAATACAAGGTCCCGAGC<br>AAGAAGTTCAAGGTCCTGGGAAACACAGACAGACACAGCA<br>TCAAGAAGAACCTGATCGGAGCACTGCTGTTCGACAGCGG<br>AGAAACAGCAGAAGCAACAAGACTGAAGAGAACAGCAAGA<br>AGAAGATACACAAGAAGAAAGAACAGAATCTGCTACCTGC<br>AGGAAATCTTCAGCAACGAAATGGCAAAGGTCGACGACAG<br>CTTCTTCCACAGACTGGAAGAAAGCTTCCTGGTCGAAGAA<br>GACAAGAAGCACGAAAGACACCCGATCTTCGGAAACATCG<br>TCGACGAAGTCGCATACCACGAAAAGTACCCGACAATCTA<br>CCACCTGAGAAAGAAGCTGGTCGACAGCACAGACAAGGCA<br>GACCTGAGACTGATCTACCTGGCACTGGCACACATGATCA<br>AGTTCAGAGGACACTTCCTGATCGAAGGAGACCTGAACCC<br>GGACAACAGCGACGTCGACAAGCTGTTCATCCAGCTGGTC<br>CAGACATACAACCAGCTGTTCGAAGAAAACCCGATCAACG<br>CAAGCGGAGTCGACGCAAAGGCAATCCTGAGCGCAAGACT<br>GAGCAAGAGCAGAAGACTGGAAAACCTGATCGCACAGCTG<br>CCGGGAGAAAAGAAGAACGGACTGTTCGGAAACCTGATCG<br>CACTGAGCCTGGGACTGACACCGAACTTCAAGAGCAACTT<br>CGACCTGGCAGAAGACGCAAAGCTGCAGCTGAGCAAGGAC<br>ACATACGACGACGACCTGGACAACCTGCTGGCACAGATCG<br>GAGACCAGTACGCAGACCTGTTCCTGGCAGCAAAGAACCT<br>GAGCGACGCAATCCTGCTGAGCGACATCCTGAGAGTCAAC<br>ACAGAAATCACAAAGGCACCGCTGAGCGCAAGCATGATCA<br>AGAGATACGACGAACACCACCAGGACCTGACACTGCTGAA<br>GGCACTGGTCAGACAGCAGCTGCCGGAAAAGTACAAGGAA<br>ATCTTCTTCGACCAGAGCAAGAACGGATACGCAGGATACA<br>TCGACGGAGGAGCAAGCCAGGAAGAATTCTACAAGTTCAT<br>CAAGCCGATCCTGGAAAAGATGGACGGAACAGAAGAACTG<br>CTGGTCAAGCTGAACAGAGAAGACCTGCTGAGAAAGCAGA<br>GAACATTCGACAACGGAAGCATCCCGCACCAGATCCACCT<br>GGGAGAACTGCACGCAATCCTGAGAAGACAGGAAGACTTC<br>TACCCGTTCCTGAAGGACAACAGAGAAAAGATCGAAAAGA<br>TCCTGACATTCAGAATCCCGTACTACGTCGGACCGCTGGC<br>AAGAGGAAACAGCAGATTCCCATGGATGACAAGAAAGAGC<br>GAAGAAACAATCACACCGTGGAACTTCGAAGAAGTCGTCG<br>ACAAGGGAGCAAGCGCACAGAGCTTCATCGAAAGAATGAC<br>AAACTTCGACAAGAACCTGCCGAACGAAAAGGTCCTGCCG<br>AAGCACAGCCTGCTGTACGAATACTTCACAGTCTACAACG<br>AACTGACAAAGGTCAAGTACGTCACAGAAGGAATGAGAAA<br>GCCGGCATTCCTGAGCGGAGAACAGAAGAAGGCAATCGTC<br>GACCTGCTGTTCAAGACAAACAGAAAGGTCACAGTCAAGC<br>AGCTGAAGGAAGACTACTTCAAGAAGATCGAATGCTTCGA<br>CAGCGTCGAAATCAGCGGAGTCGAAGACAGATTCAACGCA<br>AGCCTGGGAACATACCACGACCTGCTGAAGATCATCAAGG<br>ACAAGGACTTCCTGGACAACGAAGAAAACGAAGACATCCT<br>GGAAGACATCGTCCTGACACTGACACTGTTCGAAGACAGA<br>GAAATGATCGAAGAAAGACTGAAGACATACGCACACCTGT | 27 |

TABLE 1-continued

| Description | Sequence | SEQ ID No |
|---|---|---|
| | TCGACGACAAGGTCATGAAGCAGCTGAAGAGAAGAAGATA<br>CACAGGATGGGGAAGACTGAGCAGAAAGCTGATCAACGGA<br>ATCAGAGACAAGCAGAGCGGAAAGACAATCCTGGACTTCC<br>TGAAGAGCGACGGATTCGCAAACAGAAACTTCATGCAGCT<br>GATCCACGACGACAGCCTGACATTCAAGGAAGACATCCAG<br>AAGGCACAGGTCAGCGGACAGGGAGACAGCCTGCACGAAC<br>ACATCGCAAACCTGGCAGGAAGCCCGGCAATCAAGAAGGG<br>AATCCTGCAGACAGTCAAGGTCGTCGACGAACTGGTCAAG<br>GTCATGGGAAGACACAAGCCGGAAAACATCGTCATCGAAA<br>TGGCAAGAGAAAACCAGACAACACAGAAGGGACAGAAGAA<br>CAGCAGAGAAAGAATGAAGAGAATCGAAGAAGGAATCAAG<br>GAACTGGAAGCCAGATCCTGAAGGAACACCCGGTCGAAA<br>ACACACAGCTGCAGAACGAAAAGCTGTACCTGTACTACCT<br>GCAGAACGGAAGAGACATGTACGTCGACCAGGAACTGGAC<br>ATCAACAGACTGAGCGACTACGACGTCGACCACATCGTCC<br>CCCAGAGCTTCCTGAAGGACGACAGCATCGACAACAAGGT<br>CCTGACAAGAAGCGACAAGAACAGAGGAAAGAGCGACAAC<br>GTCCCGAGCGAAGAAGTCGTCAAGAAGATGAAGAACTACT<br>GGAGACAGCTGCTGAACGCAAAGCTGATCACACAGAGAAA<br>GTTCGACAACCTGACAAAGGCAGAGAGAGGAGGACTGAGC<br>GAACTGGACAAGGCAGGATTCATCAAGAGACAGCTGGTCG<br>AAACAAGACAGATCACAAAGCACGTCGCACAGATCCTGGA<br>CAGCAGAATGAACACAAAGTACGACGAAAACGACAAGCTG<br>ATCAGAGAAGTCAAGGTCATCACACTGAAGAGCAAGCTGG<br>TCAGCGACTTCAGAAAGGACTTCCAGTTCTACAAGGTCAG<br>AGAAATCAACAACTACCACCACGCACACGACGCATACCTG<br>AACGCAGTCGTCGGAACAGCACTGATCAAGAAGTACCCGA<br>AGCTGGAAAGCGAATTCGTCTACGGAGACTACAAGGTCTA<br>CGACGTCAGAAAGATGATCGCAAAGAGCGAACAGGAAATC<br>GGAAAGGCAACAGCAAAGTACTTCTTCTACAGCAACATCA<br>TGAACTTCTTCAAGACAGAAATCACACTGGCAAACGGAGA<br>AATCAGAAAGAGACCGCTGATCGAAACAAACGGAGAAACA<br>GGAGAAATCTCTGGGACAAGGGAAGAGACTTCGCAACAG<br>TCAGAAAGGTCCTGAGCATGCCGCAGGTCAACATCTCTCAA<br>GAAGACAGAAGTCCAGACAGGAGGATTCAGCAAGGAAAGC<br>ATCCTGCCGAAGAGAAACAGCGACAAGCTGATCGCAAGAA<br>AGAAGGACTGGGACCCGAAGAAGTACGGAGGATTCGACAG<br>CCCGACAGTCGCATACAGCGTCCTGGTCGTCGCAAAGGTC<br>GAAAAGGGAAAGAGCAAGAAGCTGAAGAGCGTCAAGGAAC<br>TGCTGGGAATCACAATCATGGAAAGAAGCAGCTTCGAAAA<br>GAACCCGATCGACTTCCTGGAAGCAAAGGGATACAAGGAA<br>GTCAAGAAGGACCTGATCATCAAGCTGCCGAAGTACAGCC<br>TGTTCGAACTGGAAAACGGAAGAAAGAGAATGCTGGCAAG<br>CGCAGGAGAACTGCAGAAGGGAAACGAACTGGCACTGCCG<br>AGCAAGTACGTCAACTTCCTGTACCTGGCAAGCCACTACG<br>AAAAGCTGAAGGGAAGCCCGGAAGACAACGAACAGAAGCA<br>GCTGTTCGTCGAACAGCACAAGCACTACCTGGACGAAATC<br>ATCGAACAGATCAGCGAATTCAGCAAGAGAGTCATCCTGG<br>CAGACGCAAACCTGGACAAGGTCCTGAGCGCATACAACAA<br>GCACAGAGACAAGCCGATCAGAGAACAGGCAGAAAACATC<br>ATCCACCTGTTCACACTGACAAACCTGGGAGCACCGGCAG<br>CATTCAAGTACTTCGACACAACAATCGACAGAAAGAGATA<br>CACAAGCACAAAGGAAGTCCTGGACGCAACACTGATCCAC<br>CAGAGCATCACAGGACTGTACGAAACAAGAATCGACCTGA<br>GCCAGCTGGGAGGAGACGGAGGAGGAAGCCCGAAGAAGAA<br>GAGAAAGGTCTAGCTAGCCATCACATTTAAAAGCATCTCA<br>GCCTACCATGAGAATAAGAGAAAGAAAATGAAGATCAATA<br>GCTTATTCATCTCTTTTTCTTTTTCGTTGGTGTAAAGCCA<br>ACACCCTGTCTAAAAAACATAAATTTCTTTAATCATTTTG<br>CCTCTTTTCTCTGTGCTTCAATTAATAAAAAATGGAAAGA<br>ACCAAAAAAAAAAAAAAGAAAAAAAAAAAAAAAACAAA<br>AAAAAAAAAAAATAAAAAAAAAAAAAAATAAAAAAAAA<br>AAAAAACAAAAAAAAAAAAAAAACAAAAAAAAAAAAA<br>AAAAAAAAAAAAAAAAAAAAAAAAAAAAAAAAAAAAAAAA<br>AAAAAAAA | |
| Cas9 mRNA with a poly-A tail comprising SEQ ID NO: 10 | TCCCGCAGTCGGCGTCCAGCGGCTCTGCTTGTTCGTGTGT<br>GTGTCGTTGCAGGCCTTATTCGGATCCGCCACCATGGACA<br>AGAAGTACAGCATCGGACTGGACATCGGAACAAACAGCGT<br>CGGATGGGCAGTCATCACAGACGAATACAAGGTCCCGAGC<br>AAGAAGTTCAAGGTCCTGGGAAACACAGACAGACACAGCA<br>TCAAGAAGAACCTGATCGGAGCACTGCTGTTCGACAGCGG<br>AGAAACAGCAGAAGCAACAAGACTGAAGAGAACAGCAAGA<br>AGAAGATACACAAGAAGAAAGAACAGAATCTGCTACCTGC<br>AGGAAATCTTCAGCAACGAAATGGCAAAGGTCGACGACAG<br>CTTCTTCCACAGACTGGAAGAAAGCTTCCTGGTCGAAGAA | 28 |

TABLE 1-continued

| Description | Sequence | SEQ ID No |
|---|---|---|
| | GACAAGAAGCACGAAAGACACCCGATCTTCGGAAACATCG | |
| | TCGACGAAGTCGCATACCACGAAAAGTACCCGACAATCTA | |
| | CCACCTGAGAAAGAAGCTGGTCGACAGCACAGACAAGGCA | |
| | GACCTGAGACTGATCTACCTGGCACTGGCACACATGATCA | |
| | AGTTCAGAGGACACTTCCTGATCGAAGGAGACCTGAACCC | |
| | GGACAACAGCGACGTCGACAAGCTGTTCATCCAGCTGGTC | |
| | CAGACATACAACCAGCTGTTCGAAGAAAACCCGATCAACG | |
| | CAAGCGGAGTCGACGCAAAGGCAATCCTGAGCGCAAGACT | |
| | GAGCAAGAGCAGAAGACTGGAAAACCTGATCGCACAGCTG | |
| | CCGGGAGAAAAGAAGAACGGACTGTTCGGAAACCTGATCG | |
| | CACTGAGCCTGGGACTGACACCGAACTTCAAGAGCAACTT | |
| | CGACCTGGCAGAAGACGCAAAGCTGCAGCTGAGCAAGGAC | |
| | ACATACGACGACGACCTGGACAACCTECTGGCACAGATCG | |
| | GAGACCAGTACGCAGACCTGTTCCTGGCAGCAAAGAACCT | |
| | GAGCGACGCAATCCTGCTGAGCGACATCCTGAGAGTCAAC | |
| | ACAGAAATCACAAAGGCACCGCTGAGCGCAAGCATGATCA | |
| | AGAGATACGACGAACACCACCAGGACCTGACACTGCTGAA | |
| | GGCACTGGTCAGACAGCAGCTGCCGGAAAAGTACAAGGAA | |
| | ATCTTCTTCGACCAGAGCAAGAACGGATACGCAGGATACA | |
| | TCGACGGAGGAGCAAGCCAGGAAGAATTCTACAAGTTCAT | |
| | CAAGCCGATCCTGGAAAAGATGGACGGAACAGAAGAACTG | |
| | CTGGTCAAGCTGAACAGAGAAGACCTGCTGAGAAAGCAGA | |
| | GAACATTCGACAACGGAAGCATCCCGCACCAGATCCACCT | |
| | GGGAGAACTGCACGCAATCCTGAGAAGACAGGAAGACTTC | |
| | TACCCGTTCCTGAAGGACAACAGAGAAAAGATCGAAAAGA | |
| | TCCTGACATTCAGAATCCCGTACTACGTCGGACCGCTGGC | |
| | AAGAGGAAACAGCAGATTCGCATGGATGACAAGAAAGAGC | |
| | GAAGAAACAATCACACCGTGGAACTTCGAAGAAGTCGTCG | |
| | ACAAGGGAGCAAGCGCACAGAGCTTCATCGAAAGAATGAC | |
| | AAAACTTCGACAAGAACCTGCCGAACGAAAAGGTCCTGCCG | |
| | AAGCACAGCCTGCTGTACGAATACTTCACAGTCTACAACG | |
| | AACTGACAAAGGTCAAGTACGTCACAGAAGGAATGAGAAA | |
| | GCCGGACATTCCTGAGCGGAGAACAGAAGAAGGCAATCGTC | |
| | GACCTGCTGTTCAAGACAAACAGAAAGGTCACAGTCAAGC | |
| | AGCTGAAGGAAGACTACTTCAAGAAGATCGAATGCTTCGA | |
| | CAGCGTCGAAATCAGCGGAGTCGAAGACAGATTCAACGCA | |
| | AGCCTGGGAACATACCACGACCTGCTGAAGATCATCAAGG | |
| | ACAAGGACTTCCTGGACAACGAAGAAAACGAAGACATCCT | |
| | GGAAGACATCGTCCTGACACTGACACTGTTCGAAGACAGA | |
| | GAAATGATCGAAGAAAGACTGAAGACATACGCACACCTGT | |
| | TCGACGACAAGGTCATGAAGCAGCTGAAGAGAAGAAGATA | |
| | CACAGGATGGGGAAGACTGAGCAGAAAGCTGATCAACGGA | |
| | ATCAGAGACAAGCAGAGCGGAAAGACAATCCTGGACTTCC | |
| | TGAAGAGCGACGGATTCGCAAACAGAAACTTCATCCAGCT | |
| | GATCCACGACGACAGCCTGACATTCAAGGAAGACATCCAG | |
| | AAGGCACAGGTCAGCGGACAGGGAGACAGCCTGCACGAAC | |
| | ACATCGCAAACCTGGCAGGAAGCCCGGCAATCAAGAAGGG | |
| | AATCCTGCAGACAGTCAAGGTCGTCGACGAACTGGTCAAG | |
| | GTCATGGGAAGACACAAGCCGGAAAACATCGTCATCGAAA | |
| | TCGCAAGAGAAAACCAGACAACACAGAAGGGACAGAAGAA | |
| | CAGCAGAGAAAGAATGAAGAGAATCGAAGAAGGAATCAAG | |
| | GAACTGGGAAGCCAGATCCTGAAGGAACACCCGGTCGAAA | |
| | ACACACAGCTGCAGAACGAAAAGCTGTACCTGTACTACCT | |
| | GCAGAACGGAAGAGACATGTACGTCGACCAGGAACTGGAC | |
| | ATCAACAGACTGAGCGACTACGACGTCGACCACATCGTCC | |
| | CGCAGAGCTTCCTGAAGGACGACAGCATCGACAACAAGGT | |
| | CCTGACAAGAAGCGACAAGAACAGAGGAAAGAGCGACAAC | |
| | GTCCCGAGCGAAGAAGTCGTCAAGAAGATGAAGAACTACT | |
| | GGAGACAGCTGCTGAACGCAAAGCTGATCACACAGAGAAA | |
| | GTTCGACAACCTGACAAAGGCAGAGAGGAGGACTGAGC | |
| | GAACTGGACAAGGCAGGATTCATCAAGAGACAGCTGGTCG | |
| | AAACAAGACAGATCACAAAGCACGTCGCACAGATCCTGGA | |
| | CAGCAGAATGAACACAAAGTACGACGAAAACGACAAGCTG | |
| | ATCAGAGAAGTCAAGGTCATCACACTGAAGAGCAAGCTGG | |
| | TCAGCGACTTCAGAAAGGACTTCCAGTTCTACAAGGTCAG | |
| | AGAAATCAACAACTACCACCACGCACACGACGCATACCTG | |
| | AACGCAGTCGTCGGAACAGCACTGATCAAGAAGTACCCGA | |
| | AGCTGGAAAGCGAATTCGTCTACGGAGACTACAAGGTCTA | |
| | CGACGTCAGAAAGATGATCGCAAAGAGCGAACAGGAAATC | |
| | GGAAAGGCAACAGCAAAGTACTTCTTCTACAGCAACATCA | |
| | TGAACTTCTTCAAGACAGAAATCACACTGGCAAACGGAGA | |
| | AATCAGAAAGAGACCGCTGATCGAAACAAACGGAGAAACA | |
| | GGAGAAATCGTCTGGGACAAGGGAAGAGACTTCGCAACAG | |
| | TCAGAAAGGTCCTGAGCATGCCGCAGGTCAACATCGTCAA | |
| | GAAGACAGAAGTCCAGACAGGAGGATTCAGCAAGGAAAGC | |
| | ATCCTGCCGAAGAGAAACAGCGACAAGCTGATCGCAAGAA | |

TABLE 1-continued

| Description | Sequence | SEQ ID No |
|---|---|---|
| | AGAAGGACTGGGACCCGAAGAAGTACGGAGGATTCGACAG<br>CCCGACAGTCGCATACAGCGTCCTGGTCGTCGCAAAGGTC<br>GAAAAGGGAAAGAGCAAGAAGCTGAAGAGCGTCAAGGAAC<br>TGCTGGGAATCACAATCATGGAAAGAAGCAGCTTCGAAAA<br>GAACCCGATCGACTTCCTGGAAGCAAAGGGATACAAGGAA<br>GTCAAGAAGGACCTGATCATCAAGCTGCCGAAGTACAGCC<br>TGTTCGAACTGGAAAACGGAAGAAAGAGAATGCTGGCAAG<br>CGCAGGAGAACTGCAGAAGGGAAACGAACTGGCACTGCCG<br>AGCAAGTACGTCAACTTCCTGTACCTGGCAAGCCACTACG<br>AAAAGCTGAAGGGAAGCCCGGAAGACAACGAACAGAAGCA<br>GCTGTTCGTCGAACAGCACAAGCACTACCTGGACGAAATC<br>ATCGAACAGATCAGCGAATTCAGCAAGAGAGTCATCCTGG<br>CAGACGCAAACCTGGACAAGGTCCTGAGCGCATACAACAA<br>GCACAGAGACAAGCCGATCAGAGAACAGGCAGAAAACATC<br>ATCCACCTGTTCACACTGACAAACCTGGGAGCACCGGCAG<br>CATTCAAGTACTTCGACACAACAATCGACAGAAAGAGATA<br>CACAAGCACAAAGGAAGTCCTGGACGCAACACTGATCCAC<br>CAGAGCATCACAGGACTGTACGAAACAAGAATCGACCTGA<br>GCCAGCTGGGAGGAGACGGAGGAGGAAGCCCGAAGAAGAA<br>GAGAAAGGTCTAGCTAGCCATCACATTTAAAAGCATCTCA<br>GCCTACCATGAGAATAAGAGAAAGAAAATGAAGATCAATA<br>GCTTATTCATCTCTTTTTCTTTTTCGTTGGTGTAAAGCCA<br>ACACCCTGTCTAAAAAACATAAATTTCTTTAATCATTTTG<br>CCTCTTTTCTCTGTGCTTCAATTAATAAAAAATGGAAAGA<br>ACCAAAAAAAAAAAATAAAAAAAAAAATAAAAAAAAAA<br>ACAAAAAAAAAAATAAAAAAAAAAACAAAAAAAAAAA<br>GAAAAAAAAAAACAAAAAAAAAAATAAAAAAAAAA | |
| Cas9 mRNA with a poly-A tail comprising SEQ ID NO: 11 | TCCCGCAGTCGGCGTCCAGCGGCTCTGCTTGTTCGTGTGT<br>GTGTCGTTGCAGGCCTTATTCGGATCCGCCACCATGGACA<br>AGAAGTACAGCATCGGACTGGACATCGGAACAAACAGCGT<br>CGGATGGGCAGTCATCACAGACGAATACAAGGTCCCGAGC<br>AAGAAGTTCAAGGTCCTGGGAAACACAGACAGACACAGCA<br>TCAAGAAGAACCTGATCGGAGCACTGCTGTTCGACAGCGG<br>AGAAACAGCAGAAGCAACAAGACTGAAGAGAACASCAAGA<br>AGAAGATACACAAGAAGAAAGAACAGAATCTGCTACCTGC<br>AGGAAATCTTCAGCAACGAAATGGCAAAGGTCGACGACAG<br>CTTCTTCCACAGACTGGAAGAAAGCTTCCTGGTCGAAGAA<br>GACAAGAAGCACGAAAGACACCCGATCTTCGGAAACATCG<br>TCGACGAAGTCGCATACCACGAAAAGTACCCGACAATCTA<br>CCACCTGAGAAAGAAGCTGGTCGACAGCACAGACAAGGCA<br>GACCTGAGACTGATCTACCTGGCACTGGCACACATGATCA<br>AGTTCAGAGGACACTTCCTGATCGAAGGAGACCTGAACCC<br>GGACAACAGCGACGTCGACAAGCTGTTCATCCAGCTGGTC<br>CAGACATACAACCAGCTGTTCGAAGAAAACCCGATCAACG<br>CAAGCGGAGTCGACGCAAAGGCAATCCTGAGCGCAAGACT<br>GAGCAAGAGCAGAAGACTGGAAAAACCTGATCGCACAGCTG<br>CCGGGAGAAAAGAAGAACGGACTGTTCGGAAACCTGATCG<br>CACTGAGCCTGGGACTGACACCGAACTTCAAGAGCAACTT<br>CGACCTGGCAGAAGACGCAAAGCTGCAGCTGAGCAAGGAC<br>ACATACGACGACGACCTGGACAACCTGCTGGCACAGATCG<br>GAGACCAGTACGCAGACCTGTTCCTGGCAGCAAAGAACCT<br>GAGCGACGCAATCCTGCTGAGCGACATCCTGAGAGTCAAC<br>ACAGAAATCACAAAGGCACCGCTGAGCGCAAGCATGATCA<br>AGAGATACGACGAACACCACCAGGACCTGACACTECTGAA<br>GGCACTGGTCAGACAGCAGCTGCCGGAAAAGTACAAGGAA<br>ATCTTCTTCGACCAGAGCAAGAACGGATACGCAGGATACA<br>TCGACGGAGGAGCAAGCCAGGAAGAATTCTACAAGTTCAT<br>CAAGCCGATCCTGGAAAAGATGGACGGAACAGAAGAACTG<br>CTGGTCAAGCTGAACAGAGAAGACCTGCTGAGAAAGCAGA<br>GAACATTCGACAACGGAAGCATCCCGCACCAGATCCACCT<br>GGGAGAACTGCACGCAATCCTGAGAAGACAGGAAGACTTC<br>TACCCGTTCCTGAAGGACAACAGAGAAAAGATCGAAAAGA<br>TCCTGACATTCAGAATCCCGTACTACGTCGGACCGCTGGC<br>AAGAGGAAACAGCAGATTCGCATGGATGACAAGAAAGAGC<br>GAAGAAACAATCACACCGTGGAACTTCGAAGAAGTCGTCG<br>ACAAGGGAGCAAGCGCACAGAGCTTCATCGAAAGAATGAC<br>AAACTTCGACAAGAACCTGCCGAACGAAAAGGTCCTGCCG<br>AAGCACAGCCTGCTGTACGAATACTTCACAGTCTACAACG<br>AACTGACAAAGGTCAAGTACGTCACAGAAGGAATGAGAAA<br>GCCGGCATTCCTGAGCGGAGAACAGAAGAAGGCAATCGTC<br>GACCTGCTGTTCAAGACAAACAGAAAGGTCACAGTCAAGC<br>AGCTGAAGGAAGACTACTTCAAGAAGATCGAATGCTTCGA<br>CAGCGTCGAAATCAGCGGAGTCGAAGACAGATTCAACGCA<br>ACAAGGACTTCCTGGACAACGAAGAAAACGAAGACATCCT<br>GGAAGACATCGTCCTGACACTGACACTGTTCGAAGACAGA | 29 |

TABLE 1-continued

| Description | Sequence | SEQ ID No |
|---|---|---|
| | GAAATGATCGAAGAAAGACTGAAGACATACGCACACCTGT<br>TCGACGACAAGGTCATGAAGCAGCTGAAGAGAAGAAGATA<br>CACAGGATGGGGAAGACTGAGCAGAAAGCTGATCAACGGA<br>ATCAGAGACAAGCAGAGCGGAAAGACAATCCTGGACTTCC<br>TGAAGAGCGACGGATTCGCAAACAGAAACTTCATCCAGCT<br>GATCCACGACGACAGCCTGACATTCAAGGAAGACATCCAG<br>AAGGCACAGGTCAGCGGACAGGGAGACAGCCTGCACGAAC<br>ACATCGCAAACCTGGCAGGAAGCCCGGCAATCAAGAAGGG<br>AATCCTGCAGACAGTCAAGGTCGTCGACGAACTGGTCAAG<br>GTCATGGGAAGACACAAGCCGGAAAACATCGTCATCGAAA<br>TGGCAAGAGAAAACCAGACAACACAGAAGGGACAGAAGAA<br>CAGCAGAGAAAGAATGAAGAGAATCGAAGAAGGAATCAAG<br>GAACTGGGAAGCCAGATCCTGAAGGAACACCCGGTCGAAA<br>ACACACAGCTGCAGAACGAAAAGCTGTACCTGTACTACCT<br>GCAGAACGGAAGAGACATGTACGTCGACCAGGAACTGGAC<br>ATCAACAGACTGAGCGACTACGACGTCGACCACATCGTCC<br>CGCAGAGCTTCCTGAAGGACGACAGCATCGACAACAAGGT<br>CCTGACAAGAAGCGACAAGAACAGAGGAAAGAGCGACAAC<br>GTCCCGAGCGAAGAAGTCGTCAAGAAGATGAAGAACTACT<br>GGAGACAGCTCCTGAACGCAAAGCTGATCACACAGAGAAA<br>GTTCGACAACCTGACAAAGGCAGAGAGAGGAGGACTGAGC<br>GAACTGGACAAGGCAGGATTCATCAAGAGACAGCTGGTCG<br>AAACAAGACAGATCACAAAGCACGTCGCACAGATCCTGGA<br>CAGCAGAATGAACACAAAGTACGACGAAAACGACAAGCTG<br>ATCAGAGAAGTCAAGGTCATCACACTGAAGAGCAAGCTGG<br>TCAGCGACTTCAGAAAGGACTTCCAGTTCTACAAGGTCAG<br>AGAAATCAACAACTACCACCACGCACACGACGCATACCTG<br>AACGCAGTCGTCGGAACAGCACTGATCAAGAAGTACCCGA<br>AGCTGGAAAGCGAATTCGTCTACGGAGACTACAAGGTCTA<br>CCACGTCAGAAAGATGATCCCAAAGAGCGAACAGGAAATC<br>GGAAAGGCAACAGCAAAGTACTTCTTCTACAGCAACATCA<br>TGAACTTCTTCAAGACAGAAATCACACTGGCAAACGGAGA<br>AATCAGAAAGAGACCGCTGATCGAAACAAACGGAGAAACA<br>GGAGAAATCGTCTGGGACAAGGGAAGAGACTTCGCAACAG<br>TCAGAAAGGTCCTGAGCATGCCGCAGGTCAACATCGTCAA<br>GAAGACAGAAGTCCAGACAGGAGGATTCAGCAAGGAAAGC<br>ATCCTGCCGAAGAGAAACAGCGACAAGCTGATCGCAAGAA<br>AGAAGGACTGGGACCCGAAGAAGTACGGAGGATTCGACAG<br>CCCGACAGTCGCATACAGCGTCCTGGTCGTCGCAAAGGTC<br>GAAAAGGGAAAGAGCAAGAAGCTGAAGAGCGTCAAGGAAC<br>TGCTGGGAATCACAATCATGGAAAGAAGCAGCTTCGAAAA<br>GAACCCGATCGACTTCCTGGAAGCAAAGGGATACAAGGAA<br>GTCAAGAAGGACCTGATCATCAAGCTGCCGAAGTACAGCC<br>TGTTCGAACTGGAAAACGGAAGAAAGAGAATGCTGGCAAG<br>CGCAGGAGAACTGCAGAAGGGAAACGAACTGGCACTGCCG<br>AGCAAGTACGTCAACTTCCTGTACCTGGCAAGCCACTACG<br>AAAAGCTGAAGGGAAGCCCGGAAGACAACGAACAGAAGCA<br>GCTGTTCGTCGAACAGCACAAGCACTACCTGGACGAAATC<br>ATCGAACAGATCAGCGAATTCAGCAAGAGAGTCATCCTGG<br>CAGACGCAAACCTGGACAAGGTCCTGAGCGCATACAACAA<br>GCACAGAGACAAGCCGATCAGAGAACAGGCAGAAAACATC<br>ATCCACCTGTTCACACTGACAAACCTGGGAGCACCGGCAG<br>CATTCAAGTACTTCGACACAACAATCGACAGAAAGAGATA<br>CACAAGCACAAAGGAAGTCCTGGACGCAACACACTGATCCAC<br>CAGAGCATCACAGGACTGTACGAAACAAGAATCGACCTGA<br>GCCAGCTGGGAGGAGACGGAGGAGGAAGCCCGAAGAAGAA<br>GAGAAAGGTCTAGCTAGCCATCACATTTAAAAGCATCTCA<br>GCCTACCATGAGAATAAGAGAAAGAAAATGAAGATCAATA<br>GCTTATTCATCTCTTTTTCTTTTTCGTTGGTGTAAAGCCA<br>ACACCCTGTCTAAAAAACATAAATTTCTTTAATCATTTTG<br>CCTCTTTTCTCTGTGCTTCAATTAATAAAAAATGGAAGA<br>ACCAAAAAAAAAAAAAAAAAAAAAAAAAAAAAAAAAAA<br>GAGAAAGGTCTAGCTAGCCATCACATTTAAAAGCATCTCA<br>GCCTACCATGAGAATAAGAGAAAGAAAATGAAGATCAATA<br>AAAAAAGAAAAAAATAAAAAAACAAAAAAACAAAAAA<br>AATAAAAAAAGAAAAAAACAAAAAAATAAAAAAA | |
| Cas9 mRNA with a poly-A tail comprising SEQ ID NO: 19 | TCCCGCAGTCGGCGTCCAGCGGCTCTGCTTGTTCGTGTGT<br>GTGTCGTTGCAGGCCTTATTCGGATCCGCCACCATGGACA<br>AGAAGTACAGCATCGGACTGGACATCGGAACAAACAGCGT<br>CGGATGGGCAGTCATCACAGACGAATACAAGGTCCCGAGC<br>AAGAAGTTCAAGGTCCTGGGAAACACAGACAGACACAGCA<br>TCAAGAAGAACCTGATCGGAGCACTGCTGTTCGACAGCGG<br>AGAAACAGCAGAAGCAACAAGACTGAAGAGAACAGCAAGA<br>AGAAGATACACAAGAAGAAAGAACAGAATCTGCTACCTGC<br>AGGAAATCTTCAGCAACGAAATGGCAAAGGTCGACGACAG | 30 |

TABLE 1-continued

| Description | Sequence | SEQ ID No |
|---|---|---|
| | CTTCTTCCACAGACTGGAAGAAAGCTTCCTGGTCGAAGAA | |
| | GACAAGAAGCACGAAAGACACCCGATCTTCGGAAACATCG | |
| | TCGACGAAGTCGCATACCACGAAAAGTACCCGACAATCTA | |
| | CCACCTGAGAAAGAAGCTGGTCGACAGCACAGACAAGGCA | |
| | GACCTGAGACTGATCTACCTGGCACTGGCACACATGATCA | |
| | AGTTCAGAGGACACTTCCTGATCGAAGGAGACCTGAACCC | |
| | GGACAACAGCGACGTCGACAAGCTGTTCATCCAGCTGGTC | |
| | CAGACATACAACCAGCTGTTCGAAGAAAACCCGATCAACG | |
| | CAAGCGGAGTCGACGCAAAGGCAATCCTGAGCGCAAGACT | |
| | GAGCAAGAGCAGAAGACTGGAAAACCTGATCGCACAGCTG | |
| | CCGGGAGAAAAGAAGAACGGACTGTTCGGAAACCTGATCG | |
| | CACTGAGCCTGGGACTGACACCGAACTTCAAGAGCAACTT | |
| | CGACCTGGCAGAAGACGCAAAGCTGCAGCTGAGCAAGGAC | |
| | ACATACGACGACGACCTGGACAACCTGCTGGCACAGATCG | |
| | GAGACCAGTACGCAGACCTGTTCCTGGCAGCAAAGAACCT | |
| | GAGCGACGCAATCCTGCTGAGCGACATCCTGAGAGTCAAC | |
| | ACAGAAATCACAAAGGCACCGCTGAGCGCAAGCATGATCA | |
| | AGAGATACGACGAACACCACCAGGACCTGACACTGCTGAA | |
| | GGCACTGGTCAGACAGCAGCTGCCGGAAAAGTACAAGGAA | |
| | ATCTTCTTCGACCAGAGCAAGAACGGATACGCAGGATACA | |
| | TCGACGGAGGAGCAAGCCAGGAAGAATTCTACAAGTTCAT | |
| | CAAGCCGATCCTGGAAAAGATGGACGGAACAGAAGAACTG | |
| | CTGGTCAAGCTGAACAGAGAAGACCTGCTGAGAAAGCAGA | |
| | GAACATTCGACAACGGAAGCATCCCGCACCAGATCCACCT | |
| | GGGAGAACTGCACGCAATCCTGAGAAGACAGGAAGACTTC | |
| | TACCCGTTCCTGAAGGACAACAGAGAAAAGATCGAAAAGA | |
| | TCCTGACATTCAGAATCCCGTACTACGTCGGACCGCTGGC | |
| | AAGAGGAAACAGCAGATTCGCATGGATGACAAGAAAGAGC | |
| | GAAGAAACAATCACACCGTGGAACTTCGAAGAAGTCGTCG | |
| | ACAAGGGAGCAAGCGCACAGAGCTTCATCGAAAGAATGAC | |
| | AAACTTCGACAAGAACCTGCCGAACGAAAAGGTCCTGCCG | |
| | AAGCACAGCCTGCTGTACGAATACTTCACAGTCTACAACG | |
| | AACTGACAAAGGTCAAGTACGTCACAGAAGGAATGAGAAA | |
| | GCCGGCATTCCTGAGCGGAGAACAGAAGAAGGCAATCGTC | |
| | GACCTGCTGTTCAAGACAAACAGAAAGGTCACAGTCAAGC | |
| | AGCTGAAGGAAGACTACTTCAAGAAGATCGAATGCTTCGA | |
| | CAGCGTCGAAATCAGCGGAGTCGAAGACAGATTCAACGCA | |
| | AGCCTGGGAACATACCACGACCTGCTGAAGATCATCAAGG | |
| | ACAAGGACTTCCTGGACAACGAAGAAAACGAAGACATCCT | |
| | GGAAGACATCGTCCTGACACTGACACTGTTCGAAGACAGA | |
| | GAAATGATCGAAGAAAGACTGAAGACATACGCACACCTGT | |
| | TCGACGACAAGGTCATGAAGCAGCTGAAGAGAAGAAGATA | |
| | CACAGGATGGGGAAGACTGAGCAGAAAGCTGATCAACGGA | |
| | ATCAGAGACAAGCAGAGCGGAAAGACAATCCTGGACTTCC | |
| | TGAAGAGCGACGGATTCGCAAACAGAAACTTCATGCAGCT | |
| | GATCCACGACGACAGCCTGACATTCAAGGAAGACATCCAG | |
| | AAGGCACAGGTCAGCGGACAGGGAGACAGCCTGCACGAAC | |
| | ACATCGCAAACCTGGCAGGAAGCCCGGCAATCAAGAAGGG | |
| | AATCCTGCAGACAGTCAAGGTCGTCGACGAACTGGTCAAG | |
| | GTCATGGGAAGACACAAGCCGGAAAACATCGTCATCGAAA | |
| | TGGCAAGAGAAAACCAGACAACACAGAAGGGACAGAAGAA | |
| | CAGCAGAGAAAGAATGAAGAGAATCGAAGAAGGAATCAAG | |
| | GAACTGGGAAGCCAGATCCTGAAGGAACACCCGGTCGAAA | |
| | ACACACAGCTGCAGAACGAAAAAGCTGTACCTGTACTACCT | |
| | GCAGAACGGAAGAGACATGTACGTCGACCAGGAACTGGAC | |
| | ATCAACAGACTGAGCGACTACGACGTCGACCACATCGTCC | |
| | CGCAGAGCTTCCTGAAGGACGACAGCATCGACAACAAGGT | |
| | CCTGACAAGAAGCGACAAGAACAGAGGAAAGAGCGACAAC | |
| | GTCCCGAGCGAAGAAGTCGTCAAGAAGATGAAGAACTACT | |
| | GGAGACAGCTGCTGAACGCAAAGCTGATCACACAGAGAAA | |
| | GTTCGACAACCTGACAAAGGCAGAGAGGAGGACTGAGC | |
| | GAACTGGACAAGGCAGGATTCATCAAGAGACAGCTGGTCG | |
| | AAACAAGACAGATCACAAAGCACGTCGCACAGATCCTGGA | |
| | CAGCAGAATGAACACAAAGTACGACGAAAACGACAAGCTG | |
| | ATCAGAGAAGTCAAGGTCATCACACTGAAGAGCAAGCTGG | |
| | TCAGCGACTTCAGAAAGGACTTCCAGTTCTACAAGGTCAG | |
| | AGAAATCAACAACTACCACCACGCACACGACGCATACCTG | |
| | AACGCAGTCGTCGGAACAGCACTGATCAAGAAGTACCCGA | |
| | AGCTGGAAAGCGAATTCGTCTACGGAGACTACAAGGTCTA | |
| | CGACGTCAGAAAGATGATCGCAAAGAGCGAACAGGAAATC | |
| | GGAAAGGCAACAGCAAAGTACTTCTTCTACAGCAACATCA | |
| | TGAACTTCTTCAAGACAGAAATCACACTGGCAAACGGAGA | |
| | AATCAGAAAGAGACCGCTGATCGAAACAAACGGAGAAACA | |
| | GGAGAAATCGTCTGGGACAAGGGAAGAGACTTCGCAACAG | |
| | TCAGAAAGGTCCTGAGCATGCCGCAGGTCAACATCGTCAA | |
| | GAAGACAGAAGTCCAGACAGGAGGATTCAGCAAGGAAAGC | |

TABLE 1-continued

| Description | Sequence | SEQ ID No |
|---|---|---|
| | ATCCTGCCGAAGAGAAACAGCGACAAGCTGATCGCAAGAA AGAAGGACTGGGACCCGAAGAAGTACGGAGGATTCGACAG CCCGACAGTCGCATACAGCGTCCTGGTCGTCGCAAAGGTC GAAAAGGGAAAGAGCAAGAAGCTGAAGAGCGTCAAGGAAC TGCTGGGAATCACAATCATGGAAAGAAGCAGCTTCGAAAA GAACCCGATCGACTTCCTGGAAGCAAAGGGATACAAGGAA GTCAAGAAGGACCTGATCATCAAGCTGCCGAAGTACAGCC TGTTCGAACTGGAAAACGGAAGAAAGAGAATGCTGGCAAG CGCAGGAGAACTGCAGAAGGGAAACGAACTGGCACTGCCG AGCAAGTACGTCAACTTCCTGTACCTGGCAAGCCACTACG AAAAGCTGAAGGGAAGCCCGGAAGACAACGAACAGAAGCA GCTGTTCGTCGAACAGCACAAGCACTACCTGGACGAAATC ATCGAACAGATCAGCGAATTCAGCAAGAGAGTCATCCTGG CAGACGCAAACCTGGACAAGGTCCTGAGCGCATACAACAA GCACAGAGACAAGCCGATCAGAGAACAGGCAGAAAACATC ATCCACCTGTTCACACTGACAAACCTGGGAGCACCGGCAG CATTCAAGTACTTCGACACAACAATCGACAGAAAGAGATA CACAAGCACAAAGGAAGTCCTGGACGCAACACTGATCCAC CAGAGCATCACAGGACTGTACGAAACAAGAATCGACCTGA GCCAGCTGGGAGGAGACGGAGGAGGAAGCCCGAAGAAGAA GAGAAAGGTCTAGCTAGCCATCACATTTAAAAGCATCTCA GCCTACCATGAGAATAAGAGAAAGAAAATGAAGATCAATA GCTTATTCATCTCTTTTTCTTTTTCGTTGGTGTAAAGCCA ACACCCTGTCTAAAAAACATAAATTTCTTTAATCATTTTG CCTCTTTTCTCTGTGCTTCAATTAATAAAAAATGGAAAGA ACCAAAAAAAAAAAAAAAAAAAAAAAAAAAAAAAAAAAAA AAAAAAAAAAAAAAAAAAAAAAAAAAAAAAAAAAAAAAAA AATAAAAAAAAAAAAAAAAAAAAAAAAAAAAAAAAA | |
| Cas9 mRNA with a poly-A tail comprising SEQ ID NO: 2 | TCCCGCAGTCGGCGTCCAGCGGCTCTGCTTGTTCGTGTGT GTGTCGTTGCAGGCCTTATTCGGATCCGCCACCATGGACA AGAAGTACAGCATCGGACTGGACATCGGAACAAACAGCGT CGGATGGGCAGTCATCACAGACGAATACAAGGTCCCGAGC AAGAAGTTCAAGGTCCTGGGAAACACAGACAGACACAGCA TCAAGAAGAACCTGATCGGAGCACTGCTGTTCGACAGCGG AGAAACAGCAGAAGCAACAAGACTGAAGAGAACAGCAAGA AGAAGATACACAAGAAGAAAGAACAGAATCTGCTACCTGC AGGAAATCTTCAGCAACGAAATGGCAAAGGTCGACGACAG CTTCTTCCACAGACTGGAAGAAAGCTTCCTGGTCGAAGAA GACAAGAAGCACGAAAGACACCCGATCTTCGGAAACATCG TCGACGAAGTCGCATACCACGAAAAGTACCCGACAATCTA CCACCTGAGAAAGAAGCTGGTCGACAGCACAGACAAGGCA GACCTGAGACTGATCTACCTGGCACTGGCACACATGATCA AGTTCAGAGGACACTTCCTGATCGAAGGAGACCTGAACCC GGACAACAGCGACGTCGACAAGCTGTTCATCCAGCTGGTC CAGACATACAACCAGCTGTTCGAAGAAAACCCGATCAACG CAAGCGGAGTCGACGCAAAGGCAATCCTGAGCGCAAGACT GAGCAAGAGCAGAAGACTGGAAAACCTGATCGCACAGCTG CCGGGAGAAAAGAAGAACGGACTGTTCGGAAACCTGATCG CACTGAGCCTGGGACTGACACCGAACTTCAAGAGCAACTT CGACCTGGCAGAAGACGCAAAGCTGCAGCTGAGCAAGGAC ACATACGACGACGACCTGGACAACCTGCTGGCACAGATCG GAGACCAGTACGCAGACCTGTTCCTGGCAGCAAAGAACCT GAGCGACGCAATCCTGCTGAGCGACATCCTGAGAGTCAAC ACAGAAATCACAAAGGCACCGCTGAGCGCAAGCATGATCA AGAGATACGACGAACACCACCAGGACCTGACACTGCTGAA GGCACTGGTCAGACAGCAGCTGCCGGAAAAGTACAAGGAA ATCTTCTTCGACCAGAGCAAGAACGGATACGCAGGATACA TCGACGGAGGAGCAAGCCAGGAAGAATTCTACAAGTTCAT CAAGCCGATCCTGGAAAAGATGGACGGAACAGAAGAACTG CTGGTCAAGCTGAACAGAGAAGACCTGCTGAGAAAGCAGA GAACATTCGACAACGGAAGCATCCCGCACCAGATCCACCT GGGAGAACTGCACGCAATCCTGAGAAGACAGGAAGACTTC TACCCGTTCCTGAAGGACAACAGAGAAAAGATCGAAAAGA TCCTGACATTCAGAATCCCGTACTACGTCGGACCGCTGGC AAGAGGAAACAGCAGATTCGCATGGATGACAAGAAAGAGC GAAGAAACAATCACACCGTGGAACTTCGAAGAAGTCGTCG ACAAGGGAGCAAGCGCACAGAGCTTCATCGAAAGAATGAC AAACTTCGACAAGAACCTGCCGAACGAAAAGGTCCTGCCG AAGCACAGCCTGCTGTACGAATACTTCACAGTCTACAACG AACTGACAAAGGTCAAGTACGTCACAGAAGGAATGAGAAA GCCGGCATTCCTGAGCGGAGAACAGAAGAAGGCAATCGTC GACCTGCTGTTCAAGACAAACAGAAAGGTCACAGTCAAGC AGCTGAAGGAAGACTACTTCAAGAAGATCGAATGCTTCGA CAGCGTCGAAATCAGCGGAGTCGAAGACAGATTCAACGCA AGCCTGGGAACATACCACGACCTGCTGAAGATCATCAAGG | 31 |

TABLE 1-continued

| Description | Sequence | SEQ ID No |
|---|---|---|
| | ACAAGGACTTCCTGGACAACGAAGAAAACGAAGACATCCT | |
| | GGAAGACATCGTCCTGACACTGACACTGTTCGAAGACAGA | |
| | GAAATGATCGAAGAAAGACTGAAGACATACGCACACCTGT | |
| | TCGACGACAAGGTCATGAAGCAGCTGAAGAGAAGAAGATA | |
| | CACAGGATGGGGAAGACTGAGCAGAAAGCTGATCAACGGA | |
| | ATCAGAGACAAGCAGAGCGGAAAGACAATCCTGGACTTCC | |
| | TGAAGAGCGACGGATTCGCAAACAGAAACTTCATGCAGCT | |
| | GATCCACGACGACAGCCTGACATTCAAGGAAGACATCCAG | |
| | AAGGCACAGGTCAGCGGACAGGGAGACAGCCTGCACGAAC | |
| | ACATCGCAAACCTGGCAGGAAGCCCGGCAATCAAGAAGGG | |
| | AATCCTGCAGACAGTCAAGGTCGTCGACGAACTGGTCAAG | |
| | GTCATGGGAAGACACAAGCCGGAAAACATCGTCATCGAAA | |
| | TGGCAAGAGAAAACCAGACAACACAGAAGGGACAGAAGAA | |
| | CAGCAGAGAAAGAATGAAGAGAATCGAAGAAGGAATCAAG | |
| | GAACTGGGAAGCCAGATCCTGAAGGAACACCCGGTCGAAA | |
| | ACACACAGCTGCAGAACGAAAAGCTGTACCTGTACTACCT | |
| | GCAGAACGGAAGAGACATGTACGTCGACCAGGAACTGGAC | |
| | ATCAACAGACTGAGCGACTACGACGTCGACCACATCGTCC | |
| | CGCAGAGCTTCCTGAAGGACGACAGCATCGACAACAAGGT | |
| | CCTGACAAGAAGCGACAAGAACAGAGGGAAAGAGCGACAAC | |
| | GTCCCGAGCGAAGAAGTCGTCAAGAAGATGAAGAACTACT | |
| | GGAGACAGCTGCTGAACGCAAAGCTGATCACACAGAGAAA | |
| | GTTCGACAACCTGACAAAGGCAGAGAGAGGAGGACTGAGC | |
| | GAACTGGACAAGGCAGGATTCATCAAGAGACAGCTGGTCG | |
| | AAAACAAGACAGATCACAAAGCACGTCGCACAGATCCTGGA | |
| | CAGCAGAATGAACACAAAGTACGACGAAAACGACAAGCTG | |
| | ATCAGAGAAGTCAAGGTCATCACACTGAAGAGCAAGCTGG | |
| | TCAGCGACTTCAGAAAGGACTTCCAGTTCTACAAGGTCAG | |
| | AGAAATCAACAACTACCACCACGCACACGACGCATACCTG | |
| | AACGCAGTCGTCGGAACAGCACTGATCAAGAAGTACCCGA | |
| | AGCTGGAAAGCGAATTCGTCTACGGAGACTACAAGGTCTA | |
| | CGACGTCAGAAAGATGATCGCAAAGAGCGAACAGGAAATC | |
| | GGAAAGGCAACAGCAAAGTACTTCTTCTACAGCAACATCA | |
| | TGAACTTCTTCAAGACAGAAATCACACTGGCAAACGGAGA | |
| | AATCAGAAAGAGACCGCTGATCGAAACAAACGGAGAAACA | |
| | GGAGAAATCGTCTGGGACAAGGGAAGAGACTTCGCAACAG | |
| | TCAGAAAGGTCCTGAGCATGCCGCAGGTCAACATCGTCAA | |
| | GAAGACAGAAGTCCAGACAGGAGGATTCAGCAAGGAAAGC | |
| | ATCCTGCCGAAGAGAAACAGCGACAAGCTGATCGCAAGAA | |
| | AGAAGGACTGGGACCCGAAGAAGTACGGAGGATTCGACAG | |
| | CCCGACAGTCGCATACAGCGTCCTGGTCGTCGCAAAGGTC | |
| | GAAAAGGGAAAGAGCAAGAAGCTGAAGAGCGTCAAGGAAC | |
| | TGCTGGGAATCACAATCATGGAAAGAAGCAGCTTCGAAAA | |
| | GAACCCGATCGACTTCCTGGAAGCAAAGGGATACAAGGAA | |
| | GTCAAGAAGGACCTGATCATCAAGCTGCCGAAGTACAGCC | |
| | TGTTCGAACTGGAAAACGGAAGAAAGAGAATGCTGGCAAG | |
| | CGCAGGAGAACTGCAGAAGGGAAACGAACTGGCACTGCCG | |
| | AGCAAGTACGTCAACTTCCTGTACCTGGCAAGCCACTACG | |
| | AAAAGCTGAAGGGAAGCCCGGAAGACAACGAACAGAAGCA | |
| | GCTGTTCGTCGAACAGCACAAGCACTACCTGGACGAAATC | |
| | ATCGAACAGATCAGCGAATTCAGCAAGAGAGTCATCCTGG | |
| | CAGACGCAAACCTGGACAAGGTCCTGAGCGCATACAACAA | |
| | GCACAGAGACAAGCCGATCAGAGAACAGGCAGAAAACATC | |
| | ATCCACCTGTTCACACTGACAAACCTGGGAGCACCGGCAG | |
| | CATTCAAGTACTTCGACACAACAATCGACAGAAAGAGATA | |
| | CACAAGCACAAAGGAAGTCCTGGACGCAACACTGATCCAC | |
| | CAGAGCATCACAGGACTGTACGAAACAAGAATCGACCTGA | |
| | GCCAGCTGGGAGGAGACGGAGGAGGAAGCCCGAAGAAGAA | |
| | GAGAAAGGTCTAGCTAGCCATCACATTTAAAAGCATCTCA | |
| | GCCTACCATGAGAATAAGAGAAAGAAAATGAAGATCAATA | |
| | GCTTATTCATCTCTTTTTCTTTTTCGTTGGTGTAAAGCCA | |
| | ACACCCTGTCTAAAAAACATAAATTTCTTTAATCATTTTG | |
| | CCTCTTTTCTCTGTGCTTCAATTAATAAAAAATGGAAGA | |
| | ACCAAAAAAAAAAAAAAAAAAAAAAAAAAAAAAAAAAA | |
| | AAAAAAAAAAAAAAAAAAAAAAAAAAAAAAAAAAAAA | |
| | AAAAAAAAAAAAAAAAAA | |

Phosphorothioate (PS) linkage or bond refers to a bond where a sulfur is substituted for one nonbridging phosphate oxygen in a phosphodiester linkage, for example in the bonds between nucleotides bases. When phosphorothioates are used to generate oligonucleotides, the modified oligonucleotides may also be referred to as S-oligos.

A "*" may be used to depict a PS modification. In this application, the terms A*, C*, U*, or G* may be used to denote a nucleotide that is linked to the next (e.g., 3') nucleotide with a PS bond.

In this application, the terms "mA*," "mC*," "mU*," or "mG*" may be used to denote a nucleotide that has been substituted with 2'-O-Me and that is linked to the next (e.g., 3') nucleotide with a PS bond.

EXAMPLES

The following examples are provided to illustrate certain disclosed embodiments and are not to be construed as limiting the scope of this disclosure in any way.

Example 1—Design and Stability of Stable Plasmids for Poly-A Coding

Poly-A tails were designed that comprised non-adenine nucleotides. The stability of plasmids encoding these poly-A tails with consecutive adenine nucleotides and non-adenine nucleotides (e.g., interrupting sequences) were compared to poly-A tails composed solely of adenine nucleotides.

The issue of loss of the number of adenosines in an mRNA poly-A tail consisting of only adenosines is highlighted in Table 2. A sequence containing a poly-A tail of 96 adenosines was inserted into a pUC57 plasmid (Genscript) and transformed into E. coli. Cells were plated on LB-Amp plates, and incubated overnight at either 30° C. or 37° C. Eight colonies were picked and inoculated into 96-well plates with LB-Amp media and grown overnight at 30° C. or 37° C. (Day 1). Samples from the Day 1 cultures were added to fresh LB-Amp media and grown for two additional days at 30° C. or 37° C. (Day 2). DNA was purified from Day 1 and Day 2 cultures and sequenced to determine poly-A tail length in the plasmids. Exemplary results are shown in Table 2 below and in FIG. 1.

TABLE 2

Poly-A length after plasmid growth in E. Coli

| | 37° C. | | | 30° C. |
|---|---|---|---|---|
| Initial colony size | Day 1 poly-A length | Day 2 poly-A length | Initial colony size | Day 1 poly-A length |
| Sm | 95 | 18 | Reg | 80 |
| Reg | 95 | 68 | Sm | 95 |
| Reg | 95 | 94 | Reg | 39 |
| Sm | 95 | N/A | Reg | 48 |
| Reg | 96 | N/A | Sm | 95 |
| Sm | 36-95 mix | 18 | Sm | 95 |
| Sm | 62 | 61 | Reg | 47 |
| Reg | 69 | 68 | Sm | 95 |

For a number of the colonies each round of growth was associated with a decrease in the number of adenosines within the poly-A tail, with only one colony maintaining over 90 adenosines through two rounds of replication. In addition, the size of bacterial colonies correlated with loss of poly-A tail length from the plasmid (i.e., larger colonies corresponded with loss of poly-A length), suggesting that sequences encoding longer poly-A tails may inhibit bacterial growth during plasmid production. DNA purified from colonies of E. coli represent a population of DNAs from individual E. coli harboring plasmid DNA. Thus, the values provided in Table 2 (and similar values described herein) represent average poly-A length of the population. Further, during PCR and sequencing of long repeats such as poly-A, the polymerase may slip, resulting in the appearance that the sequence is slightly shorter than the actual sequence. Thus, for results showing 95 adenosines, it is not certain whether the plasmid has lost one adenosine, or whether it is a PCR artifact. However, significant loss is not an artifact of polymerase slippage during PCR amplification and sequencing.

Figure 2:
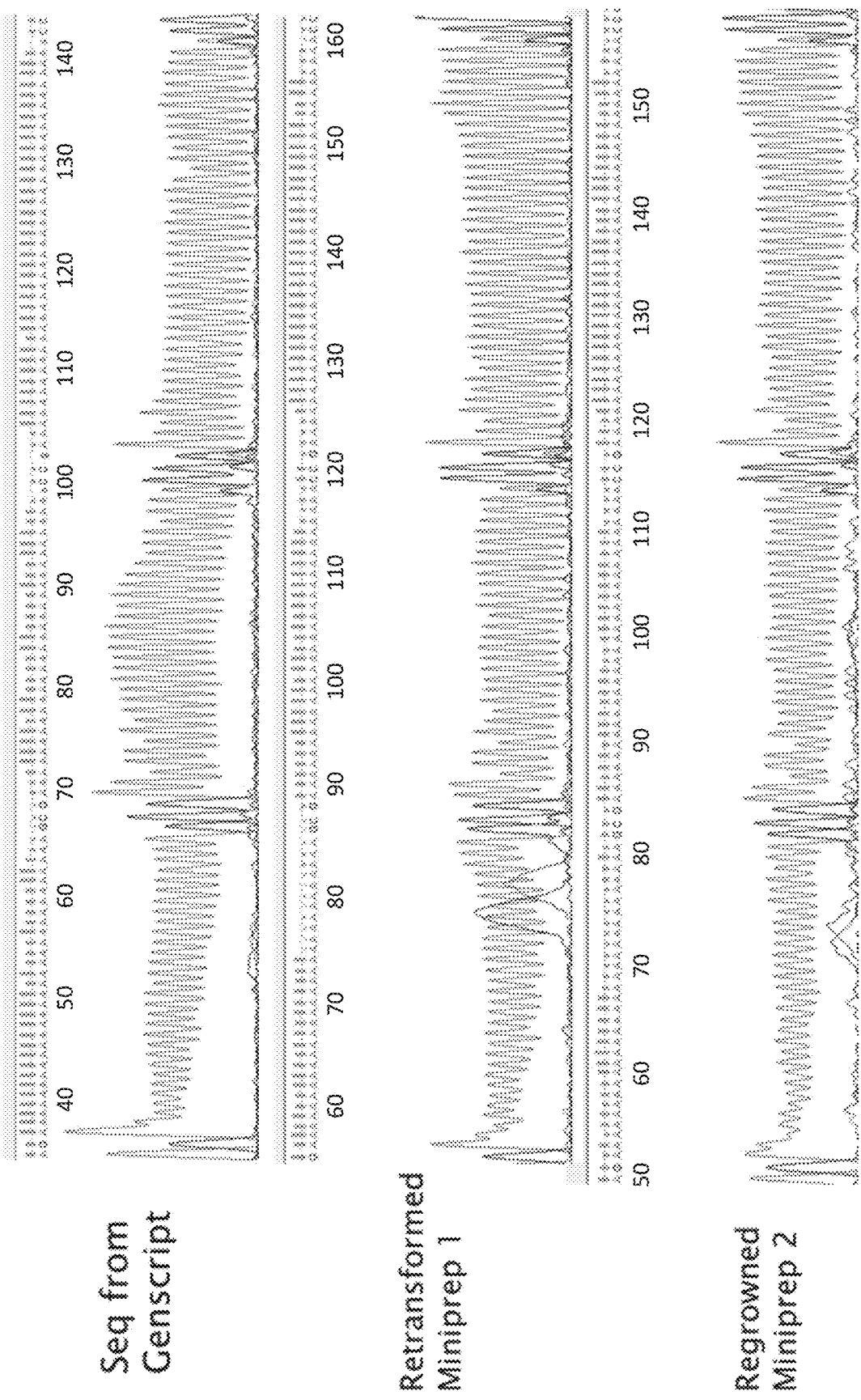
FIG. 2 shows retention of size of a poly-A tail comprising non-adenine nucleotides over 2 growth passages.

In a separate experiment, E. coli were transformed with a pUC57 plasmid containing a poly-A tail of SEQ ID NO: 1 and plated on LB-Amp plates. Eight clones were cultured through two rounds of growth and tested for maintenance of the sequence encoding the poly-A tail. Representative data on one clone is shown in FIG. 2, where no change in size of the tail was seen with the poly-A tail of SEQ ID NO: 1 over 2 rounds of growth of a plasmid encoding it. Miniprep 1 refers to the first round of growth, while Miniprep 2 refers to the second round of growth. Minipreps were performed using an Invitrogen Purelink Quick Plasmid Miniprep kit.

A plasmid encoding a poly-A tail with an additional non-adenosine pattern (SEQ ID NO: 3) was tested for its ability to withstand replication in E. coli. A sequence containing a poly-A tail of SEQ ID NO: 3 was inserted into a pUC19 plasmid (Genscript) and transformed into E. coli. Cells were plated on LB-Kan plates, and incubated overnight at either 30° C. or 37° C. Eight colonies were picked and inoculated into 96-well plates with LB-Kan media, and grown overnight at 30° C. or 37° C. (Day 1). Samples from the Day 1 cultures were added to fresh LB-Kan media and grown for two additional days at 30° C. or 37° C. (Day 2). DNA was purified from Day 1 and Day 2 cultures and sequenced to determine poly-A tail length in the plasmids. Of eight Day 1 cultures sequenced, six maintained stretches of 25, 24, 24, and 24 adenosines, and of twelve Day 2 cultures sequenced, nine maintained stretches of 25, 24, 24, and 24 adenosines, demonstrating an improvement of poly-A retention compared to adenosine-only sequences.

These data indicate that DNAs encoding poly-A tails comprising non-adenine nucleotides have improved stability over multiple rounds of plasmid growth and purification in comparison to DNAs encoding poly-A tails containing only adenosines.

Example 2—Activity of Constructs with Poly-A Tails Comprising Non-Adenine Nucleotides Experiments were performed to determine whether there was a difference in efficacy of mRNA with poly-A tails comprising non-adenine nucleotides (interrupting sequences) versus those with poly-A tails containing only adenosines. A model system was used where mRNA encoding Cas9 protein was transfected by electroporation into HEK-293 cells with a reporter plasmid encoding secreted embryonic alkaline phosphatase (SEAP), as well as a guide RNA targeting SEAP. Successful expression of Cas9 protein from the mRNA results in cleavage of the SEAP target sequence, leading to a color change reflecting decreased production of SEAP. The SEAP HEK-Blue reporter reagents were obtained from Invivogen. A sequence containing a T7 promoter and encoding a Cas9 mRNA with adenosine-only poly-A tail (designed to have 100 adenosine nucleotides, but shown as having 97 adenosine nucleotides by sequencing)

(SEQ ID NO: 6) or a sequence containing a T7 promoter and encoding a Cas9 mRNA with a poly-A tail of SEQ ID NO: 1 (SEQ ID NO: 7) were cloned into pUC57 plasmid (Genscript). mRNA was produced by in vitro transcription from the linearized plasmids encoding each mRNA.

Figure 3:
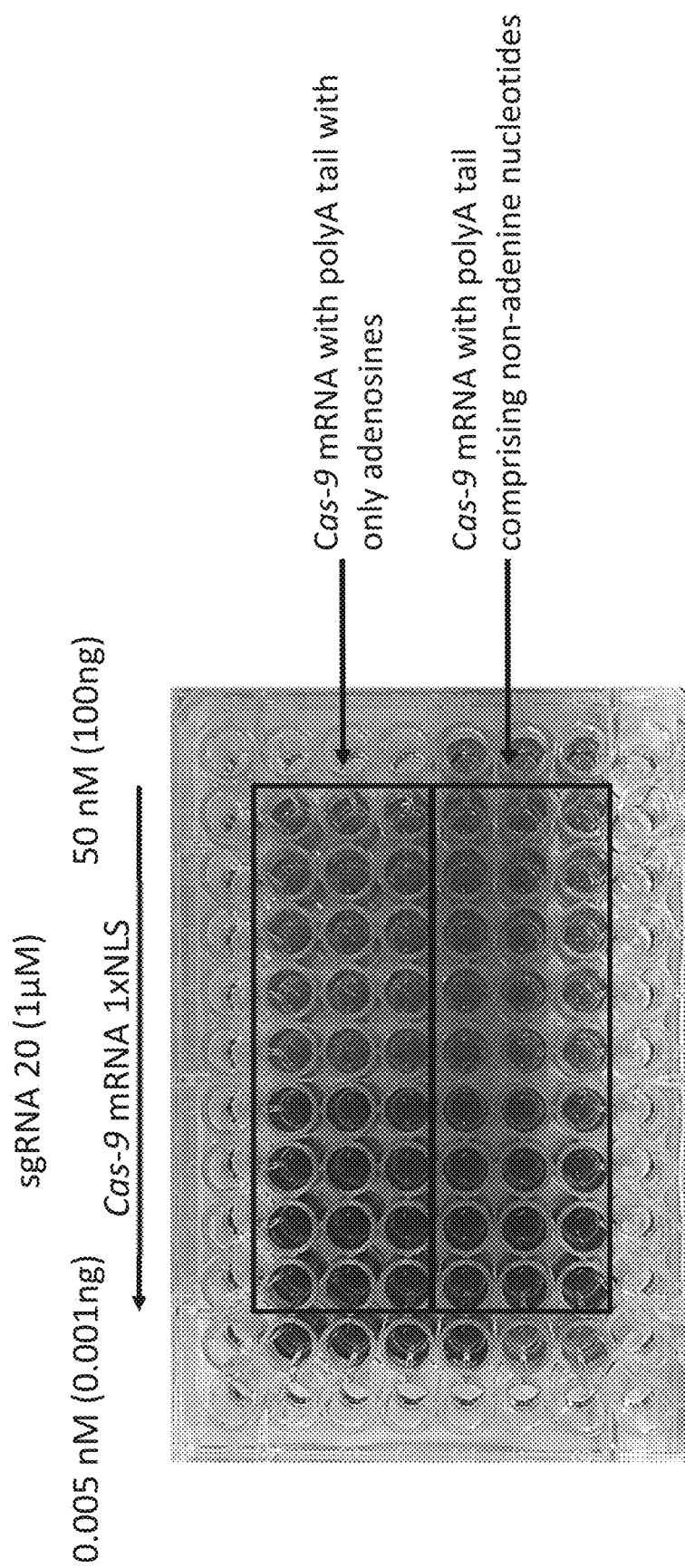
FIG. 3 shows secreted embryonic alkaline phosphatase (SEAP) levels measured in a Cas9 mRNA assay using Cas9 mRNA with a poly-A tail containing only adenosines or Cas9 mRNA with a poly-A tail comprising non-adenine nucleotides and single guide RNA targeting SEAP (SEQ ID NO: 8).

FIG. 3 shows titration of Cas9 mRNA with adenosine-only poly-A or the poly-A of SEQ ID NO: 1 in the HEK-Blue cell assay at concentrations from 0.005-50 nM, and 1 µM single guide RNA targeting SEAP (SEQ ID NO: 8).

The HEK-Blue results show that the effect of mRNA with either poly-A tail was similar across the dose-response curve. Higher concentrations of mRNA led to a decrease in SEAP reporter gene expression as evidenced by the color change to pink, as the baseline blue color indicates SEAP expression. Thus, the poly-A tail comprising non-adenine nucleotides did not change the efficacy of expression and function of a Cas9 construct compared to a poly-A tail containing only adenosines.

The efficacy of editing conferred by expression of a Cas 9 mRNA of SEQ ID NO: 6 was also compared to the Cas9 mRNA of SEQ ID NO: 7 (i.e., adenosine-only poly-A tail compared to poly-A tail of SEQ ID NO: 1). For these experiments, HEK-Blue cells were transfected with sgRNA (SEQ ID NO: 8) and the two different mRNAs by electroporation.

Figure 4:
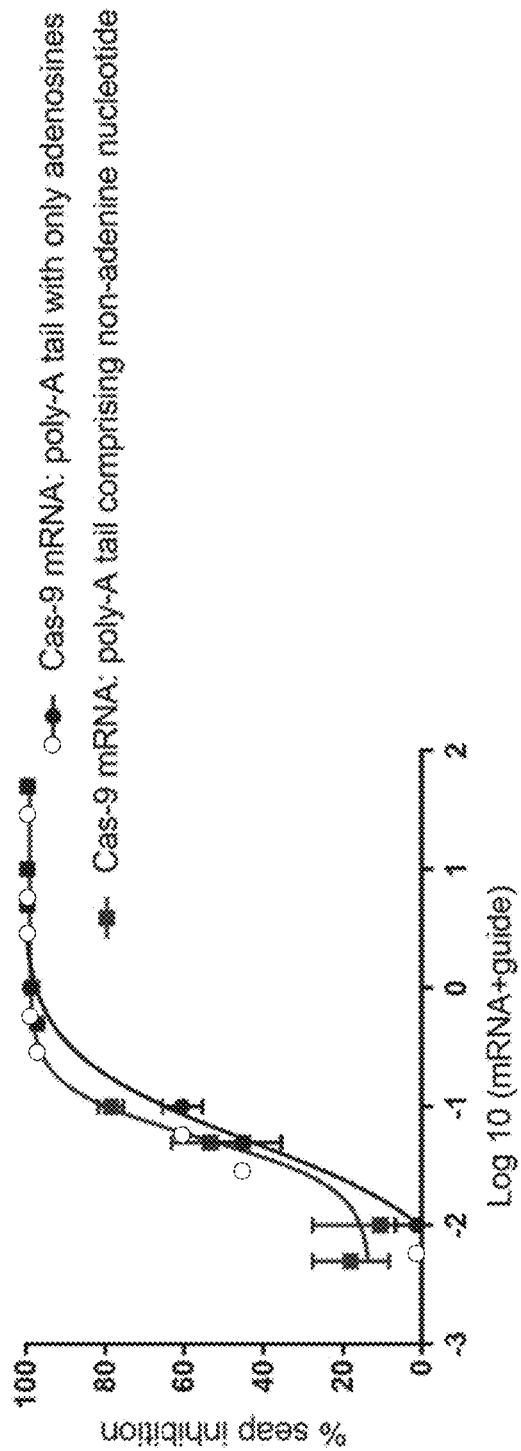
FIG. 4 shows percent SEAP inhibition measured in a Cas9 mRNA assay using Cas9 mRNA with a poly-A tail containing only adenosines or Cas9 mRNA with a poly-A tail comprising non-adenine nucleotides and single guide RNA targeting SEAP (SEQ ID NO: 8) with a 24-hour incubation.

FIG. 4 shows percent SEAP inhibition for both constructs after 24-hour incubation. The $EC_{50}$ for SEAP editing for mRNA with a poly-A tailing containing only adenosine and a poly-A tail comprising non-adenine nucleotides were similar at 0.050 and 0.054, respectively.

Figure 5:
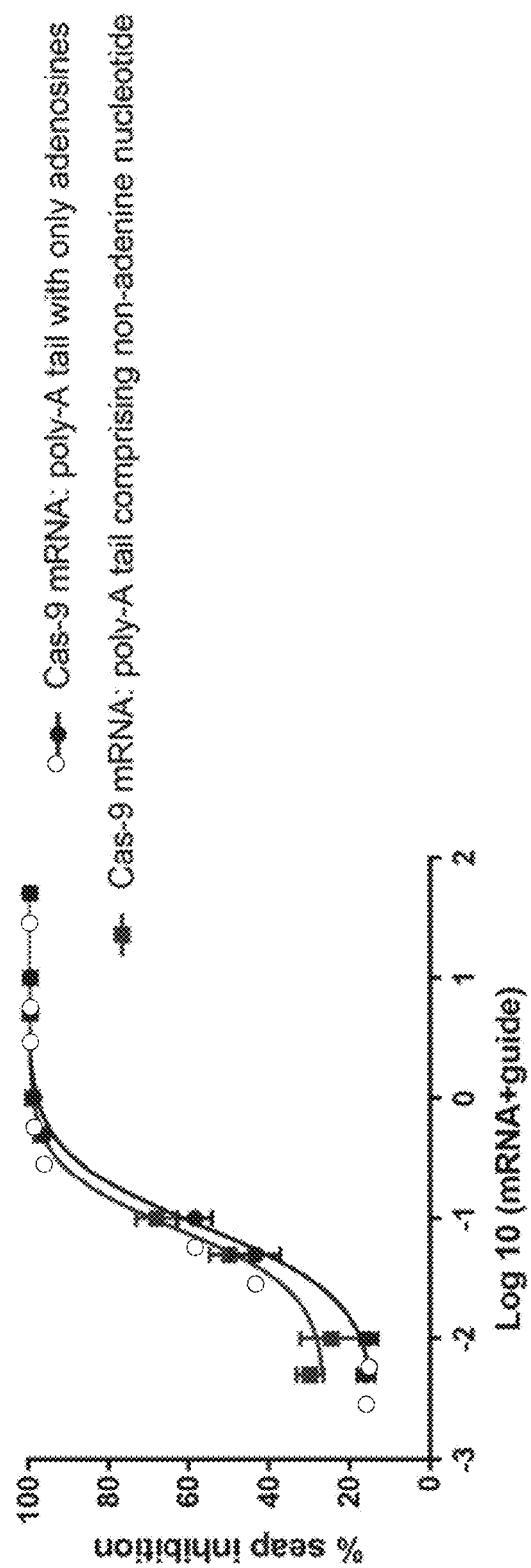
FIG. 5 shows percent SEAP inhibition measured in a Cas9 mRNA assay using Cas9 mRNA with a poly-A tail containing only adenosines or Cas9 mRNA with a poly-A tail comprising non-adenine nucleotides and single guide RNA targeting SEAP (SEQ ID NO: 8) with a 48-hour incubation.

FIG. 5 shows percent SEAP inhibition for both constructs after a 48-hour incubation. The $EC_{50}$ for SEAP editing for mRNA with a poly-A tailing containing only adenosine and a poly-A tail comprising non-adenine nucleotides were similar at 0.086 and 0.082, respectively.

mRNA expression and activity were also confirmed in vivo. The Cas9 mRNAs of SEQ ID NO: 6 (HiCas9 mRNA) and SEQ ID NO: 7 (Disrupted PolyA mRNA) were formulated with single guide RNA of SEQ ID NO: 9 (targeting mouse TTR gene) at a 1:1 weight ratio into lipid nanoparticles (LNPs) and administered to CD-1 female mice (n=5) by intravenous dosing at 1 or 0.5 mg/kg of total RNA. Blood was collected from the animals at 7 days post-dose, and serum levels of TTR protein were measured by ELISA. In short, total TTR serum levels were determined using a Mouse Prealbumin (Transthyretin) ELISA Kit (Aviva Systems Biology, Cat. OKIA00111). Kit reagents and standards were prepared according to the manufacture's protocol. The plate was read on a SpectraMax M5 plate reader at an absorbance of 450 nm. Serum TTR levels were calculated by SoftMax Pro software ver. 6.4.2 using a four parameter logistic curve fit off the standard curve. Final serum values were adjusted for the assay dilution.

Figure 6:
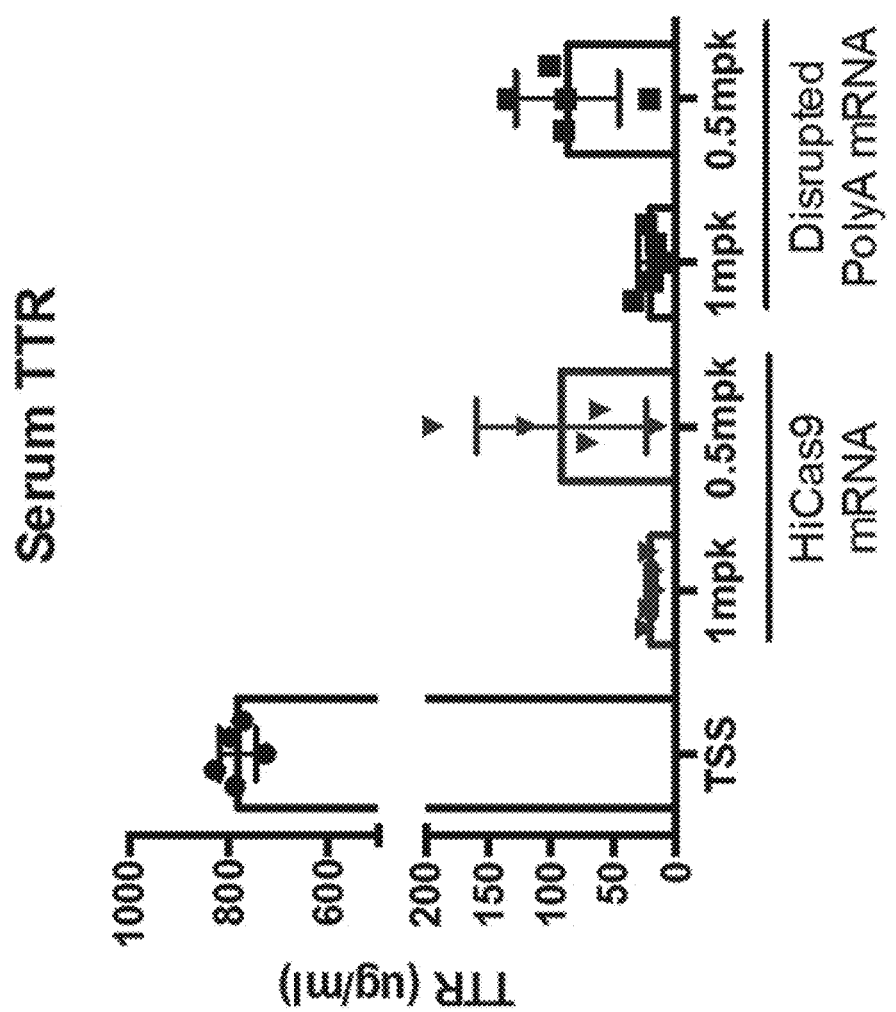
FIG. 6 shows serum transthyretin (TTR) levels in mice 7 days after dosing of a control transformation and storage solution (TSS) buffer or dosing of liquid nanoparticles (LNP) formulated with the single guide RNA of SEQ ID NO: 9 (targeting the mouse TTR gene) and either an mRNA encoded by SEQ ID NO: 6 (HiCas9 mRNA) or by SEQ ID NO: 7 (disrupted Poly-A mRNA).

FIG. 6 shows comparable levels of serum TTR knockdown (representative of percentage editing of the TTR gene) for both poly-A constructs at 7 days post-dose. Serum TTR knockdown results were confirmed by sequencing of the TTR locus in livers of the mice harvested at 7 days. Mice receiving the adenosine-only poly-A mRNA showed 61.74% and 69.84% editing at 0.5 and 1 mg/kg total RNA, respectively, while mice receiving the poly-A mRNA containing non-adenosine nucleotides showed 63.14% and 70.82% editing at 0.5 and 1 mg/kg total RNA.

Therefore, expression of a Cas9 mRNA with a poly-A tail comprising non-adenine nucleotides produced similar editing efficacy compared to a Cas9 mRNA with a poly-A tail containing only adenosines.

Example 3—Activity of Constructs with Poly-A Tails Comprising Additional Interrupting Sequences Experiments were performed to determine efficacy of mRNA with poly-A tails comprising non-adenine nucleotides versus those with poly-A tails containing only adenosine nucleotides as in Example 2. Sequences containing a T7 promoter and encoding a Cas9 mRNA with an interrupted poly-A tail comprising SEQ ID NO: 2, SEQ ID NO: 3, SEQ ID NO: 4, SEQ ID NO: 5, SEQ ID NO: 10, or SEQ ID NO: 11 were made by PCR amplification using primers to incorporate the poly-A sequences. mRNA was produced by in vitro transcription from these PCR products. mRNA for SEQ ID NO: 18 was produced by in vitro transcription from a linearized plasmid encoding the mRNA.

Figure 7:
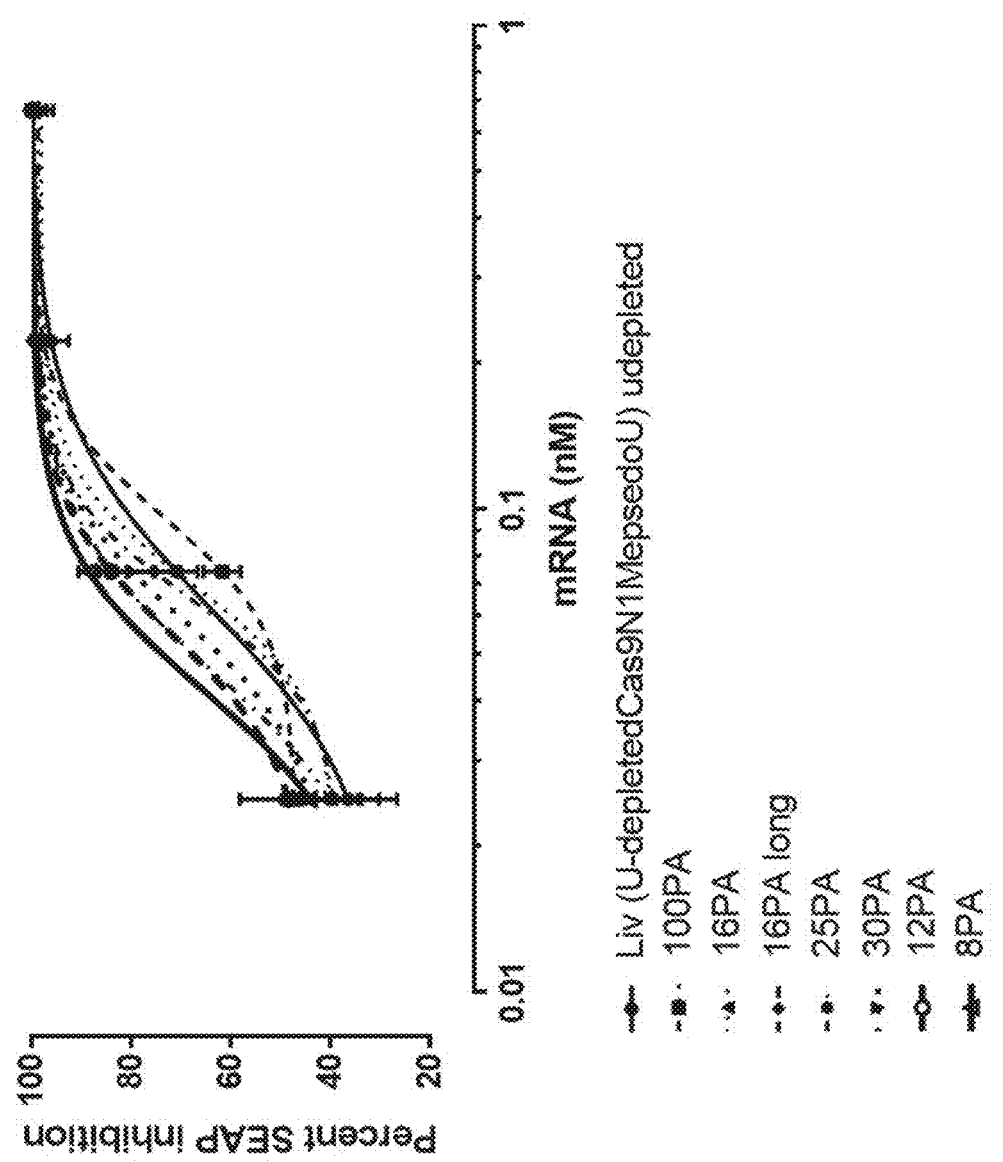
FIG. 7 shows percent SEAP inhibition measured in a Cas9 mRNA assay using Cas9 mRNA with a poly-A tails containing only adenosines or Cas9 mRNA with a poly-A tails comprising non-adenine nucleotides and single guide RNA targeting SEAP (SEQ ID NO: 8) with a 48-hour incubation.

FIG. 7 shows titration of Cas9 mRNA with adenosine-only poly-A [100PA] or the poly-A of SEQ ID NO: 2, SEQ ID NO: 3, SEQ ID NO: 4, SEQ ID NO: 5, SEQ ID NO: 10, or SEQ ID NO: 11 in the HEK-Blue cell assay at concentrations from 0.02-6 nM, and 1 µM single guide RNA targeting SEAP (SEQ ID NO: 8). Specifically, FIG. 7 shows percent SEAP inhibition for the constructs after a 48-hour incubation, and EC50 values are provided in Table 3, below. All constructs are active.

TABLE 3

EC50 values for SEAP inhibition

| PolyA | Cas9 mRNA Construct | EC50 | Standard Error |
|---|---|---|---|
| 98 consecutive adenosines | Liv (U- depleted Cas9 N1Me pseudo U) | 0.0627 | 0.0118 |
| 97 consecutive adenosines | 100 PA | 0.0956 | 0.0041 |
| SEQ ID NO: 4 | 16 PA | 0.0692 | 0.0087 |
| SEQ ID NO: 5 | 16 PA long | 0.0705 | 2.237 |
| SEQ ID NO: 3 | 25 PA | 0.0500 | 0.0213 |
| SEQ ID NO: 2 | 30 PA | 0.0591 | 0.0086 |
| SEQ ID NO: 10 | 12 PA | 0.0549 | 0.0296 |
| SEQ ID NO: 11 | 8 PA | 0.04233 | 0.0295 |

Example 4—Cloning of Long PolyA with Interrupting Sequences

A 300 nucleotide long polyA tail, SEQ ID NO:18 [300 pa], was designed comprising twelve interrupting sequences from Table 4 (below) and 13 repeats of 12 consecutive adenosines. Anchor Sequences of SEQ ID NOT: 18 were designed to minimize hybridization and self-annealing between trinucleotide interrupting sequences within the ~300 nt the poly-A tail. Table 4 below provides interrupting sequences that minimize annealing between interrupting sequences, and include the anchors used in this experiment.

To clone SEQ ID NO: 18, each of sequences PolyA-1 (SEQ ID NO: 12), PolyA-2 (SEQ ID NO: 13), PolyA-3 (SEQ ID NO: 14), and PolyA-4 (SEQ ID NO: 15) are created in the pUC57 mini vector (Genscript). The pA1-2 plasmid is created by amplifying SEQ ID NO:12 with Bcl11a primers, digesting the PCR product with restriction enzymes XhoI and AclI and ligating the restriction fragment into the pA2 plasmid comprising SEQ ID NO: 13 digested with XhoI and BstBI. The pA3-4 plasmid is created in the same manner amplifying SEQ ID NO: 14 and ligating it into the same restriction sites on plasmid pA4. The pA1-4 plasmid (comprising SEQ ID NO:18) is assembled by amplifying the SEQ ID NO: 17 sequence from pA3-4, digesting the PCR fragment with BbsI and XbaI restriction enzymes and cloning the restriction fragment into the polyA 1-2 (SEQ ID NO: 16) construct digested with BbsI and XbaI restriction enzymes. The inserts into pA1-2 and pA3-4 are assessed by Sanger sequencing from both directions using [pUC-M seq2 forward primer and pUC-M seq reverse primer] as primers (SEQ ID Nos: 20 and 21).

The resulting SEQ ID NO: 18 (300PA) polyA sequence is excised by digesting pA1-4 with XhoI and XbaI for cloning into the same sites in a protein encoding vector. All steps are carried out under standard conditions.

TABLE 4

| | | |
|---|---|---|
| CGG | CGT | CGC |
| CTG | CTT | CTC |

TABLE 4-continued

| | | |
|---|---|---|
| CAG | CAT | CAC |
| CCC | CCG | CCT |
| | | |
| GGG | GGT | GGC |
| GCG | GCT | GCC |
| GAG | GAT | GAC |
| GTG | GTT | GTC |
| | | |
| TGG | TGT | TGC |
| TTG | TTT | TTC |
| TAG | TAT | TAC |
| TCG | TTC | TCC |

I claim:

1. A DNA comprising nucleotides encoding a poly-adenylated (poly-A) tail located 3' to nucleotides encoding a protein of interest, wherein the poly-A tail comprises:
    (a) a plurality of homopolymer sequences of 8, 9, 10, 11, and/or 12 consecutive adenine (A) nucleotides; and
    (b) an interrupting sequence between each homopolymer sequence, wherein the interrupting sequence comprises:
        (i) a dinucleotide comprising two consecutive non-adenine nucleotides; or
        (ii) a trinucleotide that does not include a terminal adenine (A).

2. The DNA of claim 1, wherein the interrupting sequence prevents the loss of one or more adenine nucleotides during DNA replication as compared to the loss that occurs in a DNA comprising a 3' tail of a similar or same length that contains only adenine nucleotides.

3. The DNA of claim 1, wherein the interrupting sequence is positioned to interrupt the consecutive adenine nucleotides so that a poly (A) binding protein can bind to a stretch of consecutive adenine nucleotides.

4. The DNA of claim 1, wherein the poly-A tail comprises twenty-five homopolymer sequences of 11 or 12 consecutive adenine (A) nucleotides.

5. The DNA of claim 1, wherein the poly-A tail comprises at least 50 total adenine nucleotides.

6. The DNA of claim 1, wherein the poly-A tail comprises 40-1000, 40-900, 40-800, 40-700, 40-600, 40-500, 40-400, 40-300, 40-200, or 40-100 total adenine nucleotides.

7. The DNA of claim 1, wherein the poly-A tail comprises 300-310 total adenine nucleotides.

8. The DNA of claim 1, wherein the interrupting sequence is located after every 11 or 12 consecutive adenine nucleotides.

9. The DNA of claim 1, wherein the non-adenine nucleotide is guanine, cytosine, or thymine.

10. The DNA of claim 1, wherein the adenine nucleotides are adenosine monophosphate.

11. The DNA of claim 1, wherein the interrupting sequence comprises a trinucleotide chosen from TGG, CGG, GGT, TAT, CAT, CGT, CTC, GAT, CCT, TGT, CGC, CAC, TGC, TCG, TCT, CCC, GAC, TAG, GTT, CTG, and TTT.

12. The DNA of claim 1, wherein the interrupting sequence comprises a dinucleotide chosen from CG, GC, CC, GG, TT, CT, TC, GT, and TG.

13. The DNA of claim 1, wherein the dinucleotide interrupting sequence is CG.

14. The DNA of claim 1, wherein the interrupting sequence is chosen from TGG, CGG, GGT, TAT, CAT, CGT, CTC, GAT, CCT, TGT, CGC, CAC, TGC, TCG, TCT, CCC, GAC, TAG, GTT, CTG, TTT, and CG.

15. The DNA of claim 1, wherein the poly-A tail comprises a sequence of SEQ ID NO: 18.

16. The DNA of claim 1, wherein the protein is a therapeutic protein.

17. The DNA of claim 16, wherein the protein is a cytokine, chemokine, growth factor, RNA-guided nuclease, class 2 CRISPR-associated Cas endonuclease, chimeric Cas protein, Cas9, or modified Cas9.

18. An mRNA encoded by the DNA of claim 1.

19. An mRNA comprising a poly-adenylated (poly-A) tail located 3' to nucleotides encoding a protein of interest, wherein the poly-A tail comprises:
    (a) a plurality of homopolymer sequences of 11 or 12 consecutive adenine (A) nucleotides; and
    (b) an interrupting sequence between each homopolymer sequence, wherein the interrupting sequence comprises:
        (i) a dinucleotide comprising two consecutive non-adenine nucleotides; or
        (ii) a trinucleotide that does not include a terminal adenine (A).

20. A host cell comprising the DNA of claim 1.

21. The DNA of claim 1, wherein the DNA is within a vector.

22. The DNA of claim 21, wherein the interrupting sequence prevents loss of nucleotides encoding the poly-A tail within the vector during growth of the host cell as compared to the loss that occurs in a DNA comprising nucleotides encoding a poly-A tail of a similar or same length that contains only adenine nucleotides.

23. A method of producing mRNA from the DNA vector of claim 21, comprising:
    a. linearizing the vector downstream of the poly-A tail;
    b. denaturing the linearized vector; and
    c. contacting the denaturized DNA with an RNA polymerase in the presence of guanine, cytosine, uracil, and adenine nucleotides.

* * * * *